(12) United States Patent
Sumi

(10) Patent No.: US 7,690,838 B2
(45) Date of Patent: Apr. 6, 2010

(54) THERMAL PROPERTIES MEASUREMENT APPARATUS

(76) Inventor: Chikayoshi Sumi, Yourcourt Tokorozawa Kusunoki-dai 303, 3-18-6, Kusunoki-dai, Tokorozawa-shi, Saitama 359-0037 (JP)

( * ) Notice: Subject to any disclaimer, the term of this patent is extended or adjusted under 35 U.S.C. 154(b) by 0 days.

(21) Appl. No.: 11/110,701

(22) Filed: Apr. 21, 2005

(65) Prior Publication Data

US 2006/0239328 A1    Oct. 26, 2006

(51) Int. Cl.
*G01K 3/08* (2006.01)
*G01K 25/18* (2006.01)
*G06F 17/10* (2006.01)
*G06F 17/13* (2006.01)
*G01K 25/20* (2006.01)

(52) U.S. Cl. ............ 374/43; 374/44; 374/112; 374/166; 374/137; 703/2

(58) Field of Classification Search ............ 374/29–36, 374/43–45, 141, 100–104, 112, 137; 702/130, 702/133, 136
See application file for complete search history.

(56) References Cited

U.S. PATENT DOCUMENTS

| | | | |
|---|---|---|---|
| 3,789,654 A * | 2/1974 | Jones | 374/43 |
| 4,568,198 A * | 2/1986 | Szabo et al. | 374/43 |
| 4,630,938 A * | 12/1986 | Piorkowska-Palczewska et al. | 374/44 |
| 4,842,417 A * | 6/1989 | Asbjornsen | 374/139 |
| 4,933,887 A * | 6/1990 | Danko et al. | 702/136 |
| 4,978,229 A * | 12/1990 | Hughes | 374/30 |
| 5,112,136 A * | 5/1992 | Sakuma et al. | 374/44 |
| 5,179,407 A * | 1/1993 | Kusaka et al. | 396/93 |
| 5,297,868 A * | 3/1994 | Graebner | 374/44 |
| 5,667,300 A * | 9/1997 | Mandelis et al. | 374/43 |
| 5,667,301 A * | 9/1997 | Jurkowski et al. | 374/43 |
| 5,772,321 A * | 6/1998 | Rhodes | 374/44 |
| 5,940,784 A * | 8/1999 | El-Husayni | 702/130 |
| 6,142,662 A * | 11/2000 | Narh et al. | 374/44 |

(Continued)

FOREIGN PATENT DOCUMENTS

JP        2004205395 A  *  7/2004

OTHER PUBLICATIONS

Two dimensional reconstruction theory of thermal conductivity profiles based on the thermal wave technique. Zhou et al. 2002.*

(Continued)

*Primary Examiner*—Gail Verbitsky
(74) *Attorney, Agent, or Firm*—Sughrue Mion, PLLC

(57) ABSTRACT

A thermal property measurement apparatus capable of directly measuring thermal conductivity distribution in a ROI within a target only by measuring the temperature distribution that already exists in the ROI without generating other temperature fields artificially. The thermal property measurement apparatus includes a temperature detector for measuring temperatures at plural positions in the ROI, a distance controller for controlling a distance between the temperature detector and the target, a scanner for changing a relative position therebetween, a stage for putting the object thereon, a recorder for recording measured temperature data, position data and time data, a determination unit for determining whether at least one of thermal conductive phenomena and convection phenomena is dealt with or not, a processor for calculating thermal conductivity distribution in the ROI from the recorded data and temporal changeable references of the thermal conductivity in the ROI, and a controller.

5 Claims, 5 Drawing Sheets

U.S. PATENT DOCUMENTS

| | | | |
|---|---|---|---|
| 6,408,256 B1 * | 6/2002 | Hittle et al. | 702/130 |
| 6,422,743 B1 * | 7/2002 | Nirmalan et al. | 374/43 |
| 6,513,000 B1 * | 1/2003 | Toda | 703/13 |
| 6,679,626 B2 * | 1/2004 | Gramckow et al. | 374/43 |
| 6,701,774 B2 * | 3/2004 | Srinivasan et al. | 73/23.42 |
| 6,824,305 B1 * | 11/2004 | Boyd et al. | 374/29 |
| 7,029,172 B2 * | 4/2006 | Jones et al. | 374/137 |
| 7,113,888 B2 * | 9/2006 | Nagano et al. | 702/182 |
| 7,182,510 B2 * | 2/2007 | Cahill | 374/44 |
| 7,246,939 B1 * | 7/2007 | Gultekin | 374/44 |
| 2002/0110177 A1 * | 8/2002 | Nakayama et al. | 374/44 |
| 2002/0129741 A1 * | 9/2002 | Berube et al. | 106/486 |
| 2004/0111242 A1 * | 6/2004 | Vedula | 703/2 |
| 2004/0176680 A1 * | 9/2004 | Moonen et al. | 600/411 |

OTHER PUBLICATIONS

Meshless least-squares method for solving the steady state heat conduction equation. Liu et al. 2004.*
On the regularized algorithm of the inverse problem for diffusion equation. Anton Naumov, no date.*

* cited by examiner

THERMAL PROPERTIES MEASUREMENT APPARATUS

BACKGROUND OF THE INVENTION

1. Field of the Invention

The present invention relates to the method and apparatus for thermal property estimation (thermal properties measurement) particularly, using noncontactly measured temperatures for objects or living things.

2. Description of a Related Art

FIG. 5 shows the general thermal property estimation apparatus. In this apparatus, temperature distributions are generated in the object 4 by thermal source 13, and the generated temperatures at the plural positions are measured using the temperature detector 12 (thermocoupler etc). Then, by data processor 16, the generated heat fluxes are modeled using the finite difference method or finite element method, and the internal thermal conductivity distribution in an ROI (region of interest) is estimated using sensitivity theorem. Here, the ROI is the target region of unknown conductivity.

However, this apparatus requires the external thermal sources for realizing the temperature distributions. This causes the problem that disturbs the already existing temperature field.

Furthermore, this apparatus requires vast calculation amounts because the conductivity distribution is estimated by updating the estimate using the sensitivity theorem such that the measured temperature data equal to the calculated data using the estimate. Furthermore, for the calculation of the temperatures, the boundary conditions of the temperature and/or heat flux are required; then it was impossible to obtain the estimate of the conductivity distribution only from the internal temperature measurements in the ROI.

SUMMARY OF THE INVENTION

The purpose of the present invention is to provide apparatuses and methods for directly measuring thermal conductivity or heat transfer coefficient only from the measured temperatures (gradients of the temperatures, i.e., heat fluxes) without generating the other temperature distributions in the ROI when already the temperature distribution exists (under the condition or assumption that the heat sources/sinks exist outside the ROI).

To achieve the above-mentioned purposes, the present invention (i.e., the thermal property measurement apparatus) is equipped with:

(i) temperature detector for measuring temperatures in the three-dimensional (3D), 2D or 1D ROI in the target;

(ii) data recorder for recording the measured temperatures with the positions and times;

(iii) data processor for calculating the distributions of the temporally changeable thermal conductivity, diffusivity, transfer coefficient, ratio of the conductivity and density, ratio of the conductivity and specific heat, ratio transfer coefficient and density, ratio of the transfer coefficient and specific heat, density, specific heat, the temporal changes, frequency variances in the ROI from the recorded temperature data, position data, time data, the temporal changeable references in the ROI of the thermal conductivity, diffusivity, transfer coefficient, ratio of the conductivity and density, ratio of the conductivity and specific heat, ratio transfer coefficient and density, ratio of the transfer coefficient and specific heat, density, specific heat by carrying out the numerical solution that applies the finite difference method or finite element method to the distributions of the thermal conductivity, diffusivity, transfer coefficient, ratio of the conductivity and density, ratio of the conductivity and specific heat, ratio transfer coefficient and density, ratio of the transfer coefficient and specific heat, density, specific heat, their spatial partial derivatives, temporal partial derivative of the temperature, temperature gradient (i.e., heat flux), divergence of the gradient or temperature expressed in the prescribed first order partial differential equations; and (iv) controller for controlling the temperature detector, data recorder and data processor.

First, the thermal property measurement apparatus by the first viewpoint is equipped with:

temperature detector for measuring temperatures at plural positions in the 3D, 2D or 1D ROI in the target;

distance controller for controlling the distance between the temperature detector and object;

scanner for changing the lateral position relative between the temperature detector and object;

stage for putting the object on;

data recorder for recording the measured temperature data, the position data and time data;

determination procedure for determining at each local region or each point in the ROI whether both the thermal conductive and convection phenomena is dealt with or not (i.e., either phenomenon);

data processor for calculating the distribution of the thermal conductivity or transfer coefficient in the ROI from the recorded temperature data, position data, time data and the temporal changeable references in the ROI of the thermal conductivity and transfer coefficient by carrying out the numerical solution that applies the finite element approximation based on the calculus of variations or discrete approximation to the distribution of the thermal conductivity, transfer coefficient, temperature gradient or temperature expressed in the prescribed first order partial differential equations; and controller for controlling these.

The thermal property measurement apparatus by the second viewpoint is equipped with:

temperature detector for measuring temperatures at plural positions in the 1D ROI in the target;

distance controller for controlling the distance between the temperature detector and object;

scanner for changing the lateral position relative between the temperature detector and object;

stage for putting the object on;

data recorder for recording the measured temperature data, the position data and time data;

determination procedure for determining at each local region or each point in the ROI whether both the thermal conductive and convection phenomena is dealt with or not (i.e., either phenomenon);

data processor for calculating the distribution of the thermal conductivity or transfer coefficient in the ROI from the recorded temperature data, position data, time data and the temporal changeable references in the ROI of the thermal conductivity and transfer coefficient by carrying out the numerical solution that applies the finite element approximation based on the calculus of variations or discrete approximation to the 1D distribution of the first order partial derivative of the thermal conductivity or transfer coefficient expressed in the prescribed first order partial differential equations; and controller for controlling these.

The thermal property measurement apparatus by the third viewpoint is equipped with:

temperature detector for measuring temperatures at plural positions in the 3D, 2D or 1D ROI in the target;

distance controller for controlling the distance between the temperature detector and object;

scanner for changing the lateral position relative between the temperature detector and object;

stage for putting the object on;

data recorder for recording the measured temperature data, the position data and time data, determination procedure for determining at each local region or each point in the ROI whether both the thermal conductive and convection phenomena is dealt with or not (i.e., either phenomenon);

data processor for calculating the distributions of the thermal conductivity or transfer coefficient in the ROI from the recorded temperature data, position data, time data and the temporal changeable references in the ROI of the thermal conductivity and transfer coefficient by carrying out the numerical solution that applies the finite difference method, finite element approximation based on the Galerkin's method or discrete approximation to the distribution of the thermal conductivity, first order partial derivative of the conductivity, transfer coefficient, first order partial derivative of the transfer coefficient, temperature gradient or temperature expressed in the prescribed first order partial differential equations; and controller for controlling these.

The thermal property measurement apparatus by the fourth viewpoint is equipped with:

temperature detector for measuring temperatures at plural positions in the 3D, 2D or 1D ROI in the target, distance controller for controlling the distance between the temperature detector and object;

scanner for changing the lateral position relative between the temperature detector and object;

stage for putting the object on;

data recorder for recording the measured temperature data, the position data and time data;

determination procedure for determining at each local region or each point in the ROI whether both the thermal conductive and convection phenomena is dealt with or not (i.e., either phenomenon);

data processor for calculating the distributions of the temporally changeable thermal conductivity, diffusivity, transfer coefficient, ratio of the conductivity and density, ratio of the conductivity and specific heat, ratio of the transfer coefficient and density, ratio of the transfer coefficient and specific heat, density, specific heat, the temporal changes or frequency variances in the ROI from the recorded temperature data, position data, time data and the temporal changeable references in the ROI of the thermal conductivity, diffusivity, transfer coefficient, ratio of the conductivity and density, ratio of the conductivity and specific heat, ratio transfer coefficient and density, ratio of the transfer coefficient and specific heat, density or specific heat by carrying out the numerical solution that applies the finite element method based on the calculus of variations or discrete approximation to the distribution of the thermal conductivity, diffusivity, transfer coefficient, ratio of the conductivity and density, ratio of the conductivity and specific heat, ratio transfer coefficient and density, ratio of the transfer coefficient and specific heat, density, specific heat, temporal partial derivative of the temperature, temperature gradient (i.e., heat flux) or divergence of the gradient or temperature expressed in the prescribed first order partial differential equations; and controller for controlling the temperature detector, data recorder and data processor.

The thermal property measurement apparatus by the fifth viewpoint is equipped with:

temperature detector for measuring temperatures at plural positions in the 1D ROI in the target;

distance controller for controlling the distance between the temperature detector and object;

scanner for changing the lateral position relative between the temperature detector and object;

stage for putting the object on;

data recorder for recording the measured temperature data, the position data and time data;

determination procedure for determining at each local region or each point in the ROI whether both the thermal conductive and convection phenomena is dealt with or not (i.e., either phenomenon);

data processor for calculating the distributions of the temporally changeable thermal conductivity, diffusivity, ratio of the conductivity and density, ratio of the conductivity and specific heat, transfer coefficient, ratio of the transfer coefficient and density, ratio of the transfer coefficient and specific heat, the temporal change or the frequency variances in the ROI from the recorded temperature data, position data, time data and the temporal changeable references in the ROI of the thermal conductivity and transfer coefficient by carrying out the numerical solution that applies the finite element approximation based on the calculus of variations or discrete approximation to the 1D distribution of the first order partial derivative of the thermal conductivity, diffusivity, ratio of the conductivity and density, ratio of the conductivity and specific heat, transfer coefficient, ratio of the transfer coefficient and density or ratio of the transfer coefficient and specific heat expressed in the prescribed first partial differential equations; and controller for controlling these.

The thermal property measurement apparatus by the sixth viewpoint is equipped with:

temperature detector for measuring temperatures at plural positions in the 3D, 2D or 1D ROI in the target;

distance controller for controlling the distance between the temperature detector and object;

scanner for changing the lateral position relative between the temperature detector and object;

stage for putting the object on;

data recorder for recording the measured temperature data, the position data and time data;

determination procedure for determining at each local region or each point in the ROI whether both the thermal conductive and convection phenomena is dealt with or not (i.e., either phenomenon);

data processor for calculating the distributions of the temporally changeable thermal conductivity, diffusivity, transfer coefficient, ratio of the conductivity and density, ratio of the conductivity and specific heat, ratio of the transfer coefficient and density, ratio of the transfer coefficient and specific heat, density, specific heat, the temporal changes or frequency variances in the ROI from the recorded temperature data, position data, time data and the temporal changeable references in the ROI of the thermal conductivity, diffusivity, transfer coefficient, ratio of the conductivity and density, ratio of the conductivity and specific heat, ratio transfer coefficient and density, ratio of the transfer coefficient and specific heat, density or specific heat by carrying out the numerical solution that applies the finite difference method, finite element method based on the Galerkin's method or discrete approximation to the distribution of the thermal conductivity, diffusivity, transfer coefficient, ratio of the conductivity and density, ratio of the conductivity and specific heat, ratio transfer coefficient and density, ratio of the transfer coefficient and specific heat, density, specific heat, their first order spatial partial derivatives, temporal partial derivative of the temperature, temperature gradient (i.e., heat flux), divergence of the gradient or temperature expressed in the prescribed first order partial differential equations; and controller for controlling the temperature detector, data recorder and data processor.

The thermal property measurement apparatus can be realized for only either thermal conductive or convection phenomenon. In this case, the determination procedure (for determining whether both phenomena is dealt with or not) is not equipped.

By utilizing the present invention, the unknown conductivity or transfer coefficient distribution in the ROI in the target can be measured from the measured temperature distributions in the ROI. Particularly, when already a temperature distribution exists in the ROI, the thermal conductivity or transfer coefficient distribution can be simply measured by measuring the temperature distribution without disturbing the temperature field.

DESCRIPTION OF THE PREFERRED EMBODIMENTS

The following is explanation in detail of conduct forms of the present invention with referring to figures. The same component is referred to using the same reference number.

Figure 1:
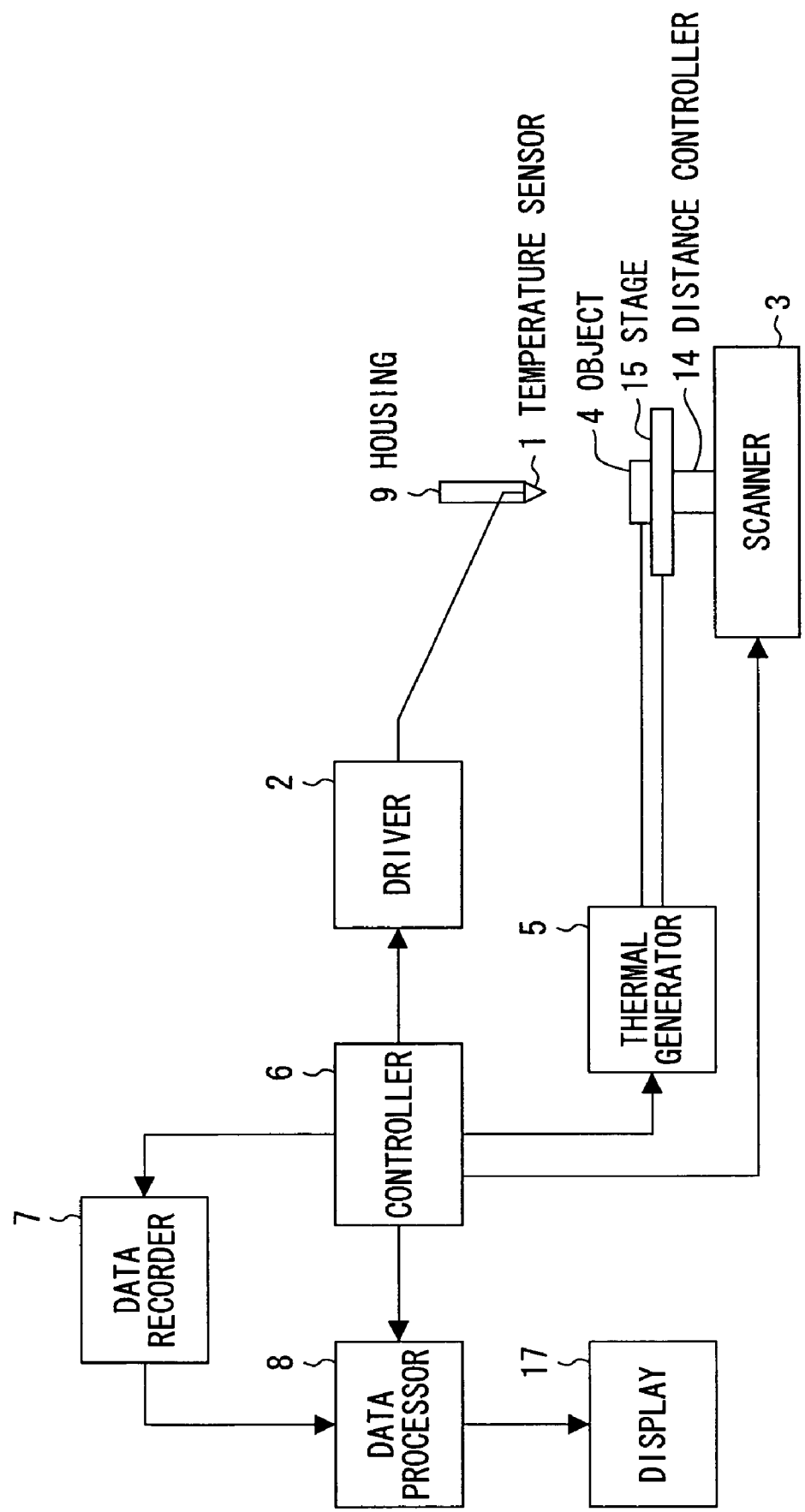
FIG. 1 shows the schematic representation of a global of thermal property measurement apparatus, related to the first conduct form of the present invention.

FIG. 1 shows the schematic representation of a global of thermal property measurement apparatus, related to the first conduct form of the present invention. For this conduct form, the object 4 is put on the stage 15. To measure the temperature in the object 4, the temperature sensor is positioned such that it faces to the object 4. The temperature sensor 1 is hold by the housing 9 and is driven by the driver 2. Thus, the temperature detector is composed of the temperature sensor and driver 2.

For this conduct form, to noncontactly and remotely measure the temperature of the target 4, an infrared temperature sensor is used as the sensor 1.

For the infrared temperature sensor, utilized is (a) simple infrared sensor using a various infrared element, (b) infrared sensor using infrared elements which enables to control the focus position by digital signal processing of the received energy, (c) infrared sensor using infrared elements which enables to control the spatial resolution by digital signal processing of the received energy, (d) infrared sensor using the sensor of (a)-(c) together with the infrared lens which enables to control the focus position and spatial resolution, (e) infrared sensor using the sensor of (a)-(d) together with the function of the active radiation of infrared whose focus position and spatial resolution can be controlled, among others.

Furthermore, to enable to control the distance between the sensor 1 and the object 4, the distance controller 14 is used. In addition, to measure the temperature distribution, the scanner 3 is used which enable to laterally shift the object 4 in two directions. These distance controller and scanner can be set to either stage or sensor. Alternatively, these can be set to both stage and sensor. These distance controller and scanner can also be set in reverse.

For this conduct form, if necessary, thermal generator 5 is used to generate the temperature distributions in the ROI in the object 4. The thermal generator is, for example, composed of thermal-electric module such as plural thermal-electric elements, the quantity of heat is injected or sucked directly or indirectly through the stage and/or reference material.

Furthermore, to reduce the effect of the convention, a vacuum chamber can be used such that it completely contains the object at least. The pressure can be kept low by using a vacuum pomp. In this case, the controller 6 can be set outside the vacuum chamber. When the sensor 1 is used outside the vacuum chamber, the temperature of an infrared window can be lowered by using a cooler.

To measure the temperatures of the target 4 put on the stage 15 using the sensor, the distance between the sensor and target is controlled by the distance controller 14, and the measurement position is changed by the scanner 3. The measured temperature data are recorded by the data recorder 7 together with the position data and time data of the temperature data. As the data recorder 7, the memory, hard disk, flexible disk, CD-ROM etc. can be utilized. After the recording, the data read out from the data recorder 7 and the reference values given in the reference regions set in the ROI are sent to the data processor 8. Here, the ROI and reference regions can be 3D, 2D or 1D.

The data processor 8 can be composed of digital circuits or CPU and program. After determining at each local region or each point in the ROI whether both the thermal conductive and convection phenomena is dealt with or not (i.e., either phenomenon), for instance, when dealing with conductive phenomenon only, by the data processor 8, the vector $L'_{In}$ or $L'$ expressing the thermal conductivity distribution in the ROI is calculated on the basis of the equations (18), (19), (20), (28), (39), (40), (116) to (124), or (134) to (136). When the absolute references (distributions) are set, if the reference value is constant, the reference value can also be set at 1.0. If the reference value is not constant, the reference values can also be set relative values with respect to 1.0. In these cases, after obtaining the relative conductivity distribution, the absolute distribution can be evaluated using the absolute reference values. The temporally changeable reference regions of the thermal conductivity, diffusivity, ratio of the conductivity and density, ratio of the conductivity and specific heat, density or specific heat can also be set in the ROI when evaluating the temporal change or frequency variances of the distributions of the thermal conductivity, diffusivity, ratio of the conductivity and density, ratio of the conductivity and specific heat, density or specific heat. Furthermore, by the data processor 8, the Laplacians and gradients can be evaluated for the respective measured distributions of the temperatures, thermal conductivity, diffusivity, ratio of the conductivity and density, ratio of the conductivity and specific heat, density or specific heat, and their frequency variances and temporal changes (absolute changes, i.e., subtraction, or relative changes, i.e., ratio) can also be evaluated.

In the case when the temperature data cannot be obtained at some position, for instance, due to the existence of the non-operable element, the calculation is performed after excluding the position at the time from the ROI. The values of the excluded positions can be interpolated or extrapolated using the calculated values in the neighbourhoods (thermal conductivity, diffusivity, ratio of the conductivity and density, ratio of the conductivity and specific heat, density, specific heat, their temporal changes or frequency variances).

If necessary, the measured results (distributions) are sent to the data recorder 7 and recorded there. Furthermore, at least one of the measured results (distributions) is displayed on the display 17 such as CRT, liquid crystal, LED, among others.

The controller 6 controls the above-described units (components) such that they work smoothly, i.e., such that the functions described in SPRY OF THE INVENTION is realized.

For this conduct form, using one of the three principles of thermal property measurement methods, the relative conductivity distribution with respect to the reference conductivities is estimated only from the measured temperature gradient vectors (obtained from temperatures distributions measured using the noncontact sensor such as an infrared sensor, etc.) and the reference conductivities (distributions) given in the reference regions.

When already the temperature gradient exists in the object, by properly setting the reference regions in the ROI, the conductivity distribution is estimated without disturbing the existing temperature field. Here, the proper reference regions mean that the reference regions properly position with respect to the thermal sources/sinks. That is, the reference regions should widely extend in the directions crossing with those of the temperature gradients. Alternatively, if the plural independent temperature fields can be measured using the thermal generator 5 (i.e., heat sources/sinks), the relative conductivity distribution can be estimated with respect to a reference conductivity given at least a reference point given in the ROI when at least three field measurements are performed for 3D estimation, at least two field measurements for 2D estimation and at least one field measurement for 1D estimation. However, we should keep in mind that, the measurement number of the temperature field should be fewer, and then, if the number becomes fewer than the dimension of the ROI, the reference regions are required to be properly set in the ROI as described above.

Furthermore, even if the measurements are noise-contaminated and the improper configurations occur (e.g., short reference regions, improper positioned reference regions), the low-pass filtering to the measurements and application of the regularization to the minimization of the functional on the basis of the calculus of variations yield the stable determination of the conductivity distribution.

In the present invention, the three principles of the thermal property measurement methods are described. In these principles, the simultaneous equations or normal equations (derived by the least-squares minimization) are solved for the unknown thermal conductivity distribution, where, in the plural measurements case, each equation derived from the measured each temperature distribution can be normalized by the magnitude of the temperature distribution, and the equations can be regularized. The first principle of the present invention involves the finite element approximation (based on the calculus of variations) or discrete approximation that is applied to the thermal conductivity distribution, temperature gradient vector distribution or temperature distribution. The second principle of the present invention involves the finite element approximation (based on the Galerkin's method) or discrete approximation, or finite difference approximation that is applied to the thermal conductivity distribution, temperature gradient vector distribution or temperature distribution. The third principle of the present invention involves the first or second principle (i.e., finite element approximation based on the calculus of variations or Galerkin's method, discrete approximation or finite difference approximation) that is used for measuring, in the nonsteady temperature distribution case, the temporally changeable distributions of the thermal conductivity, density, specific heat, product of the density and specific heat (capacity), diffusivity, ratio of the conductivity and density or ratio of the conductivity and specific heat.

Figure 2:
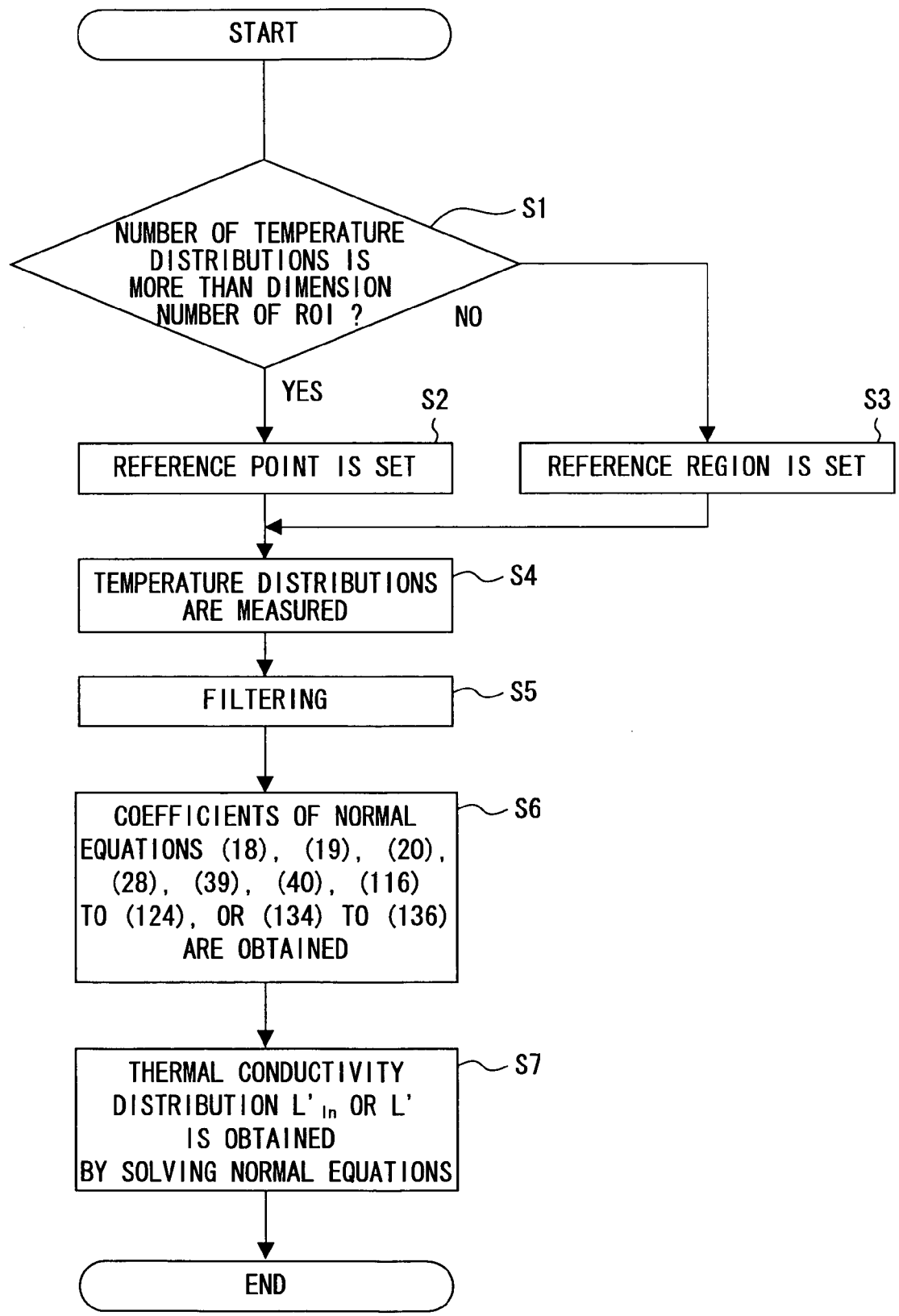
FIG. 2 shows flowchart of method of thermal property measurement, related to the first conduct form of the present invention.

Next, the thermal property measurement method related to the first conduct form of the present invention is explained, referring to the flowchart in FIG. 2.

First, at step S1, whether the measurement number of temperature distributions (or sequences of temperature distributions) is more than the dimension number of the ROI of the target 4 or not is judged. If the number is more than the dimension, at step S2 at least a reference point is set in the ROI. If the number is less than the dimension, at step S3 at least a reference region that crosses the directions of the temperature gradients is set in the ROI.

Next, at step S4 the temperature distributions (or sequences of temperature distributions) are measured in the ROI.

In the case when measuring independent plural temperature distributions (sequences of temperature distributions), the thermal generator 5 shown in FIG. 1 is used to generate the first temperature field in the ROI, which is measured. Subsequently, using the thermal generator 5, by changing the positions of the heat sources/sinks, the second temperature field is generated, which is measured. In the similar way, the generated independent temperature fields are measured.

In the case when already the temperature field exists in the ROI, without using the thermal generator 5, only the temperature field may be measured and then the reference regions may be used.

The temperature data measured by scanning the object 4 with using the distance controller 14 and scanner 3 is input to the recorder 7 together with the position and time data.

Next, at step S5 the data processor 8 shown in FIG. 1 spatially smooth the data read out from the recorder 7 by low-pass filter to mollify the measurement noise. Moreover, at step S6 the coefficients of the normal equations (18), (19), (20), (28), (39), (40), (116) to (124), or (134) to (136) are obtained. Finally, at step S7, by solving the normal equations, the thermal conductivity distribution $L'_{ln}$ or $L'$ can be obtained.

Next, the three principles of the thermal property measurement methods (i.e., data processing at steps S6 and S7) are specifically explained.

According to the first principle, after the first order partial differential equations described by the temperature gradient vectors for thermal conductivity distribution are derived, the finite element approximation (based on the calculus of variations) or discrete approximation is applied to the distribution of the thermal conductivity or temperature gradient vector (or temperature) for 3D, 2D or 1D ROI, or to the first order partial derivative of the 1D thermal conductivity distribution.

For Cartesian coordinate system (x,y,z), when the temperature can be measured in the 3D ROI, by measuring the three independent temperature fields $T_1$, $T_2$ and $T_3$, the following simultaneous partial differential equations hold, i.e., $$\begin{pmatrix} D_{1x} & D_{1y} & D_{1z} \\ D_{2x} & D_{2y} & D_{2z} \\ D_{3x} & D_{3y} & D_{3z} \end{pmatrix} \begin{pmatrix} \frac{\partial}{\partial x}(\ln k) \\ \frac{\partial}{\partial y}(\ln k) \\ \frac{\partial}{\partial z}(\ln k) \end{pmatrix} = -\begin{pmatrix} \frac{\partial D_{1x}}{\partial x} + \frac{\partial D_{1y}}{\partial y} + \frac{\partial D_{1z}}{\partial z} \\ \frac{\partial D_{2x}}{\partial x} + \frac{\partial D_{2y}}{\partial y} + \frac{\partial D_{2z}}{\partial z} \\ \frac{\partial D_{3x}}{\partial x} + \frac{\partial D_{3y}}{\partial y} + \frac{\partial D_{3z}}{\partial z} \end{pmatrix} \quad (1)$$

where the temperature gradient vectors $D_1 = -\nabla T_1$, $D_2 = -\nabla T_2$, $D_3 = -\nabla T_3$ are used.

When the temperature can be measured in the 2D ROI, by measuring the two independent temperature fields $T_1$ and $T_2$, the following simultaneous partial differential equations hold, i.e., $$\begin{pmatrix} D_{1x} & D_{1y} \\ D_{2x} & D_{2y} \end{pmatrix} \begin{pmatrix} \frac{\partial}{\partial x}(\ln k) \\ \frac{\partial}{\partial y}(\ln k) \end{pmatrix} = -\begin{pmatrix} \frac{\partial D_{1x}}{\partial x} + \frac{\partial D_{1y}}{\partial y} \\ \frac{\partial D_{2x}}{\partial x} + \frac{\partial D_{2y}}{\partial y} \end{pmatrix} \quad (2)$$

When the temperature can be measured in the 1D ROI, by measuring a temperature field $T_1$, the following simultaneous partial differential equation holds, i.e., $$D_{1x}\frac{d}{dx}(\ln k) = -\frac{d}{dx}D_{1x}. \quad (3)$$

If only a temperature field can be measured, one equation holds for respective equations (1), (2) and (3). If the plural temperature fields are measured, the simultaneous equations of the measurement number hold.

The equations (1) to (3) can hold, of which the sign of the right terms is changed, for unknown $\ln(1/k)$. Although below the determination of $\ln k$ is described, similarly $\ln(1/k)$ or $1/k$ can be determined, after that $\ln k$ or $k$ is obtained. It is often effective to deal with ink unknown when the ROI has remarkably low conductive regions such as a thermal insulator, whereas $\ln(1/k)$ unknown when the ROI has remarkably high conductive regions.

Otherwise, the equations (1) to (3) can respectively hold, of which both terms are multiplied to $k(x,y,z)$, $k(x,y)$ or $k(x)$, for $k$ itself. Otherwise, in the cases, the equations can hold, of which the sign of the terms except for ones having the first order partial derivative of $k$ is changed, for $(1/k)$. Although below the determination of $k$ is described, similarly $(1/k)$ or $\ln(1/k)$ can be determined, after that $k$ or $\ln k$ is obtained. It is often effective to deal with $k$ unknown when the ROI has remarkably low conductive regions such as a thermal insulator, whereas $(1/k)$ unknown when the ROI has remarkably high conductive regions.

In general, the initial condition can be given in the plural reference regions $w_m$ ($m=1, \ldots, N$) in the ROI in the following form, i.e., $$\ln k(x,y,z) = \ln k'(x,y,z) \quad (4)$$

or $$k(x,y,z) = k'(x,y,z)$$

where $$(x,y,z) \in w_m \ (m=1 \sim N).$$

However, when the measurement number equals to the dimension of the ROI, it is sufficient that at least a reference region is given in the ROI.

On the basis of the calculus of variations, the finite approximation is applied to the conductivity distribution or temperature gradient vector distributions (or temperature distributions) represented in the spatial partial differential equations like these.

Below, the functionals for 3D, 2D and 1D ROI are described using respective $L_{ln}$ and L as the vectors expressing the conductivity distribution $\ln k$ and $k$ in the ROI, and s as the vector expressing the temperature gradient vector distributions Di (or temperature distributions Ti), where i ($=1, \ldots, M$) denotes the measured temperature, and M is the number of the independent measured temperature fields ($\geq 1$).

For 3D ROI, the functional obtained by applying the calculus of variations to the conductivity distribution is $$I_i(L_{ln}) = \quad (5)$$

$$\iiint \left[ \frac{1}{4} D_{ix} \left\{ \frac{\partial}{\partial x}(\ln k)^2 \right\} + \frac{1}{4} D_{iy} \left\{ \frac{\partial}{\partial y}(\ln k)^2 \right\} + \frac{1}{4} D_{iz} \left\{ \frac{\partial}{\partial z}(\ln k)^2 \right\} + \left( \frac{\partial}{\partial x} D_{ix} + \frac{\partial}{\partial y} D_{iy} + \frac{\partial}{\partial z} D_{iz} \right)(\ln k) \right] dV.$$

For 3D ROI, the functional obtained by applying the calculus of variations to the temperature gradient vector distributions (or temperature distributions) is $$I_i(s) = \frac{1}{2} \iiint (kD_{ix}^2 + kD_{iy}^2 + kD_{iz}^2) dV \quad (6)$$

or $$I_i(s) = \frac{1}{2} \iiint \left\{ k\left(\frac{\partial}{\partial x}T_i\right)^2 + k\left(\frac{\partial}{\partial y}T_i\right)^2 + k\left(\frac{\partial}{\partial z}T_i\right)^2 \right\} dV.$$

For 2D ROI, the functional obtained by applying the calculus of variations to the conductivity distribution is $$I_i(L_{ln}) = \iint \left[ \frac{1}{4} D_{ix} \left\{ \frac{\partial}{\partial x}(\ln k)^2 \right\} + \frac{1}{4} D_{iy} \left\{ \frac{\partial}{\partial y}(\ln k)^2 \right\} + \left( \frac{\partial}{\partial x} D_{ix} + \frac{\partial}{\partial y} D_{iy} \right)(\ln k) \right] dA. \quad (7)$$

For 2D ROI, the functional obtained by applying the calculus of variations to the temperature gradient vector distributions (or temperature distributions) is $$I_i(s) = \frac{1}{2} \iint (kD_{ix}^2 + kD_{iy}^2) dA \quad (8)$$

or $$I_i(s) = \frac{1}{2} \iint \left\{ k\left(\frac{\partial}{\partial x}T_i\right)^2 + k\left(\frac{\partial}{\partial y}T_i\right)^2 \right\} dA.$$

For 1D ROI, the functional obtained by applying the calculus of variations to the conductivity distribution is $$I_i(L_{ln}) = \int \left[ \frac{1}{4} D_{ix} \left\{ \frac{d}{dx} (\ln k)^2 \right\} + \left( \frac{d}{dx} D_{ix} \right) (\ln k) \right] dx \quad (9)$$

or $$I_i(L_{ln}) = \int \left[ \frac{1}{2} D_{ix} \left\{ \frac{d}{dx} \ln k \right\}^2 + \left( \frac{d}{dx} D_{ix} \frac{d}{dx} \ln k \right) \right] dx.$$

For 1D ROI, the functional obtained by applying the calculus of variations to the temperature gradient vector distributions (or temperature distributions) is $$I_i(s) = \frac{1}{2} \int k D_{ix}^2 dx \quad (10)$$

or $$I_i(s) = \frac{1}{2} \int k \left( \frac{d}{dx} T_i \right)^2 dx.$$

The functionals (5) to (10) is finite-element-approximated with respect to the conductivity distribution $L_{ln}$, L or temperature gradient vector distributions s.

The temperature distribution measurement data used in (5) to (10) are low-pass filtered, and the temperature gradient vector distribution data are evaluated by applying a differential filter to the low-pass filtered temperature data, or applying a differential filter with a cutoff frequency to the raw temperature measurement data, or applying the partial derivatives to the temperature distribution data expressed using basis functions. Moreover, the distribution data of the divergence of the temperature gradient vector are also evaluated by applying such differential filters to the distributions of the temperature gradient vector, or applying the partial derivatives to the distributions of the temperature gradient vector expressed using basis functions.

When dealing with the functionals of (5), (7) and (9), in practical, one of the following functionals (i=1, . . . , M) can be used, $$II_i(L_{ln}) = \frac{1}{\sqrt{P_i}} I_i(L_{ln}) \quad (11)$$

or $$II(L_{ln}) = \sum_i^M \left\| \frac{1}{\sqrt{P_i}} \frac{\partial}{\partial L_{ln}} I_i(L_{ln}) \right\|^2$$

$$\left( \text{or } II(L_{ln}) = \sum_i^M \left\| \frac{\partial}{\partial L_{ln}} I_i(L_{ln}) \right\|^2 \right), \quad (12)$$

where Pi is a power of the temperature gradient vector distribution Di(x,y,z) in the ROI (if possible, Pi is multiplied to the standard deviation of the respective power).

These can be dealt with as functionals for $L_{ln}$. The equation (11) can be used only when only one temperature field is measured. The functional in the parenthesis in the equation (12) is normalized functional. For instance, when the ROI is 3D, these functionals are minimized with respect to the unknown conductivity distribution ln k(I,J,K) (i.e., vector $L'_{ln}$) after the functionals are finite-element-approximated using basis functions and further the low-pass filtered distributions of the temperature gradient vector Di(I,J,K) and divergence of the temperature gradient vector, and reference conductivities (distributions) ln k'(I,J,K) are substituted into the functionals. Otherwise, the functionals are minimized with respect to the conductivity distribution ln(I,J,K) (i.e., vector $L''_{ln}$) in the ROI, after which the low-pass-filtered distributions of the temperature gradient vector Di(I,J,K) and divergence of the temperature gradient vector, and reference conductivities (distributions) ln k'(I,J,K) are substituted.

As the result, from (11), the simultaneous equations for unknown conductivity ln k(I,J,K) (i.e., vector $L'_{ln}$) are derived in the case when one temperature field Ti is measured.

$$A_i L'_{ln} = a_i \quad (13)$$

Furthermore, from (12), the normal equations are derived for the unknown conductivity distribution ln k(I,J,K) (i.e., vector $L'_{ln}$) on the basis of the least-squares-minimization in the case when plural temperature distributions Ti (i=1, . . . , M) are measured.

$$A' L'_{ln} = a' \quad (14)$$

Here, A' and a' are respectively expressed as $\Sigma_i A'i$ and $\Sigma_i a'i$ using the matrix $A'i (= A i^T A i)$ and vector $a'i (= A i^T a i)$ which appear in the normal equations $A'i L'_{ln} = a'i$ obtained by minimizing the functional $II(L'_{ln})$ [eq. (12)] with respect to $L'_{ln}$ after the reference conductivities (distributions) are substituted into the functional (12) when only the temperature distribution Ti is measured.

By solving these, as the estimation result, ln k(x,y,z) is obtained. Here, Ai and ai in equation (13) and A'i and a'i in (14) are respectively matrixes and vectors composed of the basis functions, measured distributions of the temperature gradient vector Di(I,J,K) and divergence of the temperature gradient vector, and reference conductivities (distributions) ln k'(I,J,K). The same as in the case when the ROI is 2D or 1D.

Ai, ai, A' and a' are composed of the low-pass filtered distributions of the temperature gradient vector and divergence of the temperature gradient vector. Then, the inverse of the matrixes Ai and A' amplify the high frequency noise remained in the vectors ai and a'. Moreover, particularly when one temperature distribution is measured (M=1), the configurations of the thermal sources/sinks and reference regions possibly become improper ones. As the results, $L'_{ln}$ becomes unstable. Thus, occasionally the reconstruction (estimation) can be stabilized by the application of the so-called regularization.

That is, the following penalty terms are considered in a continuous coordinate system, where the regularization parameters $\alpha_{1i}$, $\alpha_{2i}$ and $\alpha_{3i}$ (positive values) being able to be set for each measured temperature distribution Ti is used.

For 3D ROI, $$\int\int\int \left[ \alpha_{1i} (\ln k)^2 + \alpha_{2i} \left\{ \left( \frac{\partial}{\partial x} (\ln k) \right)^2 + \left( \frac{\partial}{\partial y} (\ln k) \right)^2 + \left( \frac{\partial}{\partial z} (\ln k) \right)^2 \right\} + \alpha_{3i} \left\{ \frac{\partial^2}{\partial x^2} (\ln k) + \frac{\partial^2}{\partial y^2} (\ln k) + \frac{\partial^2}{\partial z^2} (\ln k) \right\}^2 \right] dV. \quad (15)$$

For 2D ROI, $$\int\int\left[\alpha_{1i}(\ln k)^2 + \alpha_{2i}\left\{\left(\frac{\partial}{\partial x}(\ln k)\right)^2 + \left(\frac{\partial}{\partial y}(\ln k)\right)^2\right\} + \alpha_{3i}\left\{\frac{\partial^2}{\partial x^2}(\ln k) + \frac{\partial^2}{\partial y^2}(\ln k)\right\}^2\right]dA. \quad (16)$$

For 1D ROI, $$\int\left[\alpha_{1i}(\ln k)^2 + \alpha_{2i}\left\{\frac{d}{dx}(\ln k)\right\}^2 + \alpha_{3i}\left\{\frac{d^2}{dx^2}(\ln k)\right\}^2\right]dx. \quad (17)$$

That is, when one temperature field Ti is measured and the functional (11) is dealt with, the respective penalty terms (15) to (17) are finite-element-approximated using the same basis functions as those used for the finite-element approximating equations (5), (7) and (9). For instance, when the ROI is 3D, the functional IIi(L'$_{In}$) [eq. (11)] added to the penalty terms is minimized with respect to L'$_{In}$ after the reference conductivities (distributions) ln k'(I,J,K) are substituted into ln(I,J,K). Otherwise, the respective penalty terms (15) to (17) are finite-difference-approximated. Similarly, the functional IIi(L'$_{In}$) [eq. (11)] added to the penalty terms is minimized with respect to L'$_{In}$ after the reference conductivities (distributions) ln k'(I,J,K) are substituted into ln k(I,J,K). As the result, for instance, when the ROI is 3D, the regularized simultaneous equations are derived for the unknown conductivity distribution ln k(I,J,K) (i.e., vector L'$_{In}$).

$$(A_i + \alpha_{1i}I + \alpha_{2i}G^TG + \alpha_{3i}G^TGG^TG)L'_{In} = a_i \quad (18)$$

By solving these equations, as the estimation result, ln k(I,J,K) is obtained. Here, respective $G^TG$ and $G^TGG^TG$ are the Laplacian and squared Laplacian operators approximated by the finite element or finite difference (discrete). The same as in the case when the ROI is 2D or 1D.

The regularization parameters $\alpha_{1i}$, $\alpha_{2i}$ and $\alpha_{3i}$ can also be set at negative values in eq. (18). The absolute values of $\alpha_{1i}$, $\alpha_{2i}$ and $\alpha_{3i}$ can be set large such that the matrix multiplied to the vector L'$_{In}$ becomes numerically stable. Alternatively, the absolute values can be set small and large respectively when the SNR (accuracy) of each measured temperature gradient distribution data is high and low (the SNR depends on the magnitude of the measured temperature gradient distribution). For instance, the values can be set proportional to the reciprocal of the square root of the SNR of the power of each measured temperature gradient distribution data. Here, the SNR of the temperature gradient distribution depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component distributions of the temperature gradient vector differ each other. Accordingly, $\alpha_{2i}$ and $\alpha_{3i}$ can also be set at different values for respective directions of the partial derivatives in eqs. (15) and (16). That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component distribution data. Furthermore, the absolute values of $\alpha_{2i}$ and $\alpha_{3i}$ can also be set small and large respectively when the data spatial interval is long and short (for instance, such that they becomes proportional to the reciprocal of the distance). Thus, these absolute values can also be set proportional to the product of the weighted absolute values determined by the respective factors determining the SNRs of each temperature gradient vector distribution and component distributions.

Here, the measurement of the SNR (accuracy) of the temperature measurement is performed to evaluate the accuracy of the measurement equipment. The SNR of the power can be estimated from the ratio of the squared mean and variance of the temperature distributions measured for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector distribution Di(x,y,z) over the ROI can be estimated from the temperature gradient vector data of the nodes (I,J,K) of each element.

The regularization parameters can also be set spatially varying in eqs (15) to (17). Thus, the regularization parameters $\alpha_{1i}$, $\alpha_{2i}$ and $\alpha_{3i}$ can also be set at negative values in eq. (18). The absolute values of $\alpha_{1i}$, $\alpha_{2i}$ and $\alpha_{3i}$ can be set large such that the local matrix multiplied to the thermal conductivity at each point of interest in vector L'$_{In}$ becomes numerically stable. Alternatively, the absolute values can be set small and large respectively when the SNR (accuracy) of each measured temperature gradient data of each point of interest is high and low (the SNR depends on the magnitude of the measured temperature gradient data). For instance, the values can be set proportional to the reciprocal of the square root of the SNR of the power of each measured temperature gradient data of each point. Here, the SNR of the temperature gradient data depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component data of the temperature gradient vector differ each other at each point. Accordingly, $\alpha_{2i}$ and $\alpha_{3i}$ can also be set at different values for respective directions of the partial derivatives in eqs. (15) and (16) as well as the positions. That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component data of each point. Furthermore, the absolute values of $\alpha_{2i}$ and $\alpha_{3i}$ can also be set small and large respectively when the data spatial interval is long and short (for instance, such that they becomes proportional to the reciprocal of the distance). Thus, these absolute values can also be set proportional to the product of the weighted absolute values determined by the respective factors determining the SNRs of each temperature gradient vector and components.

Here, the measurement of the SNR (accuracy) of the temperature measurement is performed to evaluate the accuracy of the measurement equipment. The SNR of the power can be estimated from the ratio of the squared mean and variance of the temperatures measured at each point for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector Di(x,y,z) can be estimated for each nodes (I,J,K) or each element.

Next, when more temperature fields Ti (i=1, . . . , M) than one field are measured and the functional (12) is dealt with, the respective penalty terms (15) to (17) are finite-element-approximated using the same basis functions as those used for the finite-element approximating equations (5), (7) and (9). For instance, when the ROI is 3D, the functional II(L'$_{In}$) [eq. (12)] added to the penalty terms is minimized with respect to L'$_{In}$ after the reference conductivities (distributions) ln k'(I,J,K) are substituted into ln k(I,J,K). Otherwise, the respective penalty terms (15) to (17) are finite-difference-approximated. Similarly, the functional II(L'$_{In}$) [eq. (12)] added to the penalty terms is minimized with respect to L'$_{In}$ after the reference conductivities (distributions) ln k'(I,J,K) are substituted into ln k(I,J,K). As the result, for instance, when the ROI is 3D, the regularized simultaneous equations are derived for the unknown conductivity distribution ln k(I,J,K) (vector L'$_{In}$).

$$(A'+\alpha_1 I+\alpha_2 G^T G+\alpha_3 G^T GG^T G)L'_{In}=a'$$

$$\alpha_1=\Sigma_i \alpha_{1i},\ \alpha_2=\Sigma_i \alpha_{2i},\ ,\ \alpha_3=\Sigma_i \alpha_{3i} \qquad (19)$$

By solving these equations, as the estimation result, ln k(I,J,K) is obtained. Here, respective $G^T G$ and $G^T GG^T G$ are the Laplacian and squared Laplacian operators approximated by the finite element or finite difference (discrete). The same as in the case when the ROI is 2D or 1D.

The regularization parameters $\alpha_1$, $\alpha_2$ and $\alpha_3$ in (19) can be set large such that the matrix multiplied to the vector L'$_{In}$ becomes numerically positive definite. Alternatively, the values $\alpha_{1i}$, $\alpha_{2i}$ and $\alpha_{3i}$ can be set small and large respectively when the SNR (accuracy) of each measured temperature gradient distribution data is high and low (the SNR depends on the magnitude of the measured temperature gradient distribution). For instance, the values can be set proportional to the reciprocal of the SNR of the power of each measured temperature gradient distribution data. Here, the SNR of the temperature gradient distribution depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component distributions of the temperature gradient vector differ each other. Accordingly, $\alpha_{2i}$ and $\alpha_{3i}$ can also be set at different values for respective directions of the partial derivatives in eqs. (15) and (16). That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the SNR of the power of the measured temperature gradient component distribution data. Furthermore, the absolute values of $\alpha_{2i}$ and $\alpha_{3i}$ can also be set small and large respectively when the data spatial interval is long and short (for instance, such that they becomes proportional to the reciprocal of the squared distance). Thus, these absolute values can also be set proportional to the product of the weighted absolute values determined by the respective factors determining the SNRs of each temperature gradient vector distribution and component distributions.

Here, the measurement of the SNR (accuracy) of the temperature measurement is performed to evaluate the accuracy of the measurement equipment. The SNR of the power can be estimated from the ratio of the squared mean and variance of the temperature distributions measured for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector distribution Di(x,y,z) over the ROI can be estimated from the temperature gradient vector data of the nodes (I,J,K) of each element.

The regularization parameters $\alpha_1$, $\alpha_2$ and $\alpha_3$ can also be set spatially varying in eqs (15) to (17). Thus, the values can be set large such that the local matrix multiplied to the thermal conductivity at each point of interest in vector L'$_{In}$ becomes numerically positive definite. Alternatively, the values can be set small and large respectively when the SNR (accuracy) of each measured temperature gradient data of each point of interest is high and low (the SNR depends on the magnitude of the measured temperature gradient data. For instance, the values $\alpha_{1i}$, $\alpha_{2i}$ and $\alpha_{3i}$ can be set proportional to the reciprocal of the SNR of the power of each measured temperature gradient data of each point. Here, the SNR of the temperature gradient data depends on the measured temperature distribution data itself and the spatial intervals of the data (i.e., the direction of the gradient of the temperature and magnitudes of the gradient vector components) In addition, the SNR also depends on the direction of the aperture. Thus, the SNRs of the component data of each temperature gradient vector differ each other at each point. Accordingly, $\alpha_{2i}$ and $\alpha_{3i}$ can also be set at different values for respective directions of the partial derivatives in eqs. (15) and (16) as well as the positions. That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the SNR of the power of the measured temperature gradient component data of each point. Furthermore, the absolute values of $\alpha_{2i}$ and $\alpha_{3i}$ canal so be set small and large respectively when the data spatial distance is long and short (for instance, such that they becomes proportional to the reciprocal of the squared distance). Thus, these absolute values can also be set proportional to the product of the weighted absolute values determined by the respective factors determining the SNRs of each temperature gradient vector and components.

Here, the measurement of the SNR (accuracy) of the temperature measurement is performed to evaluate the accuracy of the measurement equipment. The SNR of the power can be estimated from the ratio of the squared mean and variance of the temperatures measured at each point for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector Di(x,y,z) can be estimated for each nodes (I,J,K) or each element.

Alternatively, when temperature fields Ti (i=1, . . . , M) are measured and the functional (12) is dealt with, the respective penalty terms (15) to (17) are similarly finite-element-approximated using the same basis functions as those used for the finite-element approximating equations (5), (7) and (9). Furthermore, for instance, when the ROI is 3D, the functional Ii(L'$_{In}$) in the squared norm of functional II(L'$_{In}$) [eq. (12)] added to the penalty terms is minimized with respect to L'$_{In}$ after the reference conductivities (distributions) ln k'(I,J,K) are substituted into ln k(I,J,K). Finally, the summation of the squared norm is minimized with respect to $L'_{ln}$. Otherwise, the respective penalty terms (15) to (17) are finite-difference-approximated. Similarly, the functional $Ii(L'_{ln})$ in the squared norm of functional $II(L'_{ln})$ [eq. (12)] added to the penalty terms is similarly minimized with respect to $L'_{ln}$ after the reference conductivities (distributions) ln k'(I,J,K) are substituted into ln k(I,J,K). Finally, the summation of the squared norm is minimized with respect to $L'_{ln}$. As the result, for instance, when the ROI is 3D, the regularized simultaneous equations are derived for the unknown conductivity distribution ln k(I,J,K) (i.e., vector $L'_{ln}$).

$$\sum_i (A_i + \alpha_{1i}I + \alpha_{2i}G^TG + \alpha_{3i}G^TGG^TG)^T \quad (20)$$

$$(A_i + \alpha_{1i}I + \alpha_{2i}G^TG + \alpha_{3i}G^TGG^TG)L'_{ln} =$$

$$\sum_i (A_i + \alpha_{1i}I + \alpha_{2i}G^TG + \alpha_{3i}G^TGG^TG)^T a_i$$

By solving these equations, as the estimation result, ln k(I,J,K) is obtained. Here, respective $G^TG$ and $G^TGG^TG$ are the Laplacian and squared Laplacian operators approximated by the finite element or finite difference (discrete). The same as in the case when the ROI is 2D or 1D.

The regularization parameters $\alpha_{1i}$, $\alpha_{2i}$ and $\alpha_{3i}$ can also be set at negative values in eq. (20). The absolute values of $\alpha_{1i}$, $\alpha_{2i}$ and $\alpha_{3i}$ can be set large such that the matrix multiplied to the vector $L'_{ln}$ becomes numerically positive definite. Alternatively, the absolute values can be set small and large respectively when the SNR (accuracy) of each measured temperature gradient distribution data is high and low (the SNR depends on the magnitude of the measured temperature gradient distribution). For instance, the values can be set proportional to the reciprocal of the square root of the SNR of the power of each measured temperature gradient distribution data. Here, the SNR of the temperature gradient distribution depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component distributions of each temperature gradient vector differ each other. Accordingly, $\alpha_{2i}$ and $\alpha_{3i}$ can also be set at different values for respective directions of the partial derivatives in eqs. (15) and (16). That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component distribution data. Furthermore, the absolute values of $\alpha_{2i}$ and $\alpha_{3i}$ can also be set small and large respectively when the data spatial interval is long and short (for instance, such that they becomes proportional to the reciprocal of the distance). Thus, these absolute values can also be set proportional to the product of the weighted absolute values determined by the respective factors determining the SNRs of each temperature gradient vector distribution and component distributions.

Here, the measurement of the SNR (accuracy) of the temperature measurement is performed to evaluate the accuracy of the measurement equipment. The SNR of the power can be estimated from the ratio of the squared mean and variance of the temperature distributions measured for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector distribution Di(x,y,z) over the ROI can be estimated from the temperature gradient vector data of the nodes (I,J,K) of each element.

The regularization parameters can also be set spatially varying in eqs (15) to (17). Thus, the regularization parameters $\alpha_{1i}$, $\alpha_{2i}$ and $\alpha_{3i}$ can also be set at negative values in eq. (20). The absolute values of $\alpha_{1i}$, $\alpha_{2i}$ and $\alpha_{3i}$ can be set large such that the local matrix multiplied to the thermal conductivity at each point of interest in vector $L'_{ln}$ becomes numerically stable. Alternatively, the absolute values can be set small and large respectively when the SNR (accuracy) of each measured temperature gradient data of each point of interest is high and low (the SNR depends on the magnitude of the measured temperature gradient data). For instance, the values can be set proportional to the reciprocal of the square root of the SNR of the power of each measured temperature gradient data of each point. Here, the SNR of the temperature gradient data depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component data of each temperature gradient vector differ each other at each point. Accordingly, $\alpha_{2i}$ and $\alpha_{3i}$ can also be set at different values for respective directions of the partial derivatives in eqs. (15) and (16) as well as the positions. That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component data of each point. Furthermore, the absolute values of $\alpha_{2i}$ and $\alpha_{3i}$ can also be set small and large respectively when the data spatial interval is long and short (for instance, such that they becomes proportional to the reciprocal of the distance). Thus, these absolute values can also be set proportional to the product of the weighted absolute values determined by the respective factors determining the SNRs of each temperature gradient vector and components.

Here, the measurement of the SNR (accuracy) of the temperature measurement is performed to evaluate the accuracy of the measurement equipment. The SNR of the power can be estimated from the ratio of the squared mean and variance of the temperatures measured at each point for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector Di(x,y,z) can be estimated for each nodes (I,J,K) or each element.

When the calculus of variations is applied to the thermal conductivity distribution in the ROI after eqs. (1) to (3) are respectively multiplied by k(x,y,z), k(x,y) and k(x), the functionals are derived as follows (when the ROI is 1D, a functional is also derived by applying the calculus of variations to the first order partial derivative of the conductivity).

For 3D ROI, the functional is $$I_i(L) = \int\int\int \left[\frac{1}{4}D_{ix}\left\{\frac{\partial}{\partial x}(k)^2\right\} + \frac{1}{4}D_{iy}\left\{\frac{\partial}{\partial y}(k)^2\right\} + \frac{1}{4}D_{iz}\left\{\frac{\partial}{\partial z}(k)^2\right\} + \frac{1}{2}\left(\frac{\partial}{\partial x}D_{ix} + \frac{\partial}{\partial y}D_{iy} + \frac{\partial}{\partial z}D_{iz}\right)(k)^2\right]dV. \quad (5')$$

For 2D ROI, the functional is $$I_i(L) = \iint \left[ \frac{1}{4} D_{ix} \left\{ \frac{\partial}{\partial x}(k)^2 \right\} + \frac{1}{4} D_{iy} \left\{ \frac{\partial}{\partial y}(k)^2 \right\} + \frac{1}{2} \left( \frac{\partial}{\partial x} D_{ix} + \frac{\partial}{\partial y} D_{iy} \right)(k)^2 \right] dA. \quad (7')$$

For 1D ROI, the functional is $$I_i(L) = \int \left[ \frac{1}{4} D_{ix} \left\{ \frac{d}{dx}(k)^2 \right\} + \frac{1}{2} \left( \frac{d}{dx} D_{ix} \right)(k)^2 \right] dx \quad (9')$$

or $$I_i(L) = \int \left[ \frac{1}{2} D_{ix} \left\{ \frac{d}{dx} k \right\}^2 + \frac{1}{4} \left( \frac{d}{dx} D_{ix} \frac{d}{dx}(k)^2 \right) \right] dx.$$

Pi in functionals (11) and (12) is a summation of the power of the inner product distribution of the temperature gradient vector Di(x,y,z) and gradient operator for k(x,y,z) in the ROI (if possible, multiplied to the standard deviation of the respective power) and the power of the divergence distribution of Di(x,y,z) in the ROI (if possible, multiplied to the standard deviation of the respective power). The below described eqs. (25) to (27) are used as the penalty terms for regularization terms, and similarly, the regularized normal equations (18) to (20) can be derived for the unknown thermal conductivity distribution L'.

For eq. (18), the regularization parameters can be, for instance, set proportional to the reciprocal of the square root of the SNR of the power determined by the accuracy (SNR) of the products of the temperature gradient vector Di(x,y,z) components and partial derivative operator in the same direction and the accuracy (SNR) of the divergence components of Di(x,y,z). Otherwise, the parameters can also be set proportional to the reciprocal of the root square of the SNR of the power determined by the accuracy (SNR) of the differences of the inner product of Di(x,y,z) and gradient operator in the intervals $\Delta x$, $\Delta y$ and $\Delta z$ in I, J and K directions and the accuracy (SNR) of the differences of the divergence of Di(x,y,z) in the intervals $\Delta x$, $\Delta y$ and $\Delta z$ in I, J and K directions.

For eq. (19), the regularization parameters can be, for instance, set proportional to the reciprocal of the SNR of the power determined by the accuracy (SNR) of the products of the temperature gradient vector Di(x,y,z) components and partial derivative operator in the same direction and the accuracy (SNR) of the divergence components of Di(x,y,z). Otherwise, the parameters can also be set proportional to the reciprocal of the SNR of the power determined by the accuracy (SNR) of the differences of the inner product of Di(x,y,z) and gradient operator in the intervals $\Delta x$, $\Delta y$ and $\Delta z$ in I, J and K directions and the accuracy (SNR) of the differences of the divergence of Di(x,y,z) in the intervals $\Delta x$, $\Delta y$ and $\Delta z$ in I, J and K directions.

For eq. (20), the regularization parameters can be, for instance, set proportional to the reciprocal of the square root of the SNR of the power determined by the accuracy (SNR) of the products of the temperature gradient vector Di(x,y,z) components and partial derivative operator in the same direction and the accuracy (SNR) of the divergence components of Di(x,y,z). Otherwise, the parameters can also be set proportional to the reciprocal of the root square of the SNR of the power determined by the accuracy (SNR) of the differences of the inner product of Di(x,y,z) and gradient operator in the intervals $\Delta x$, $\Delta y$ and $\Delta z$ in I, J and K directions and the accuracy (SNR) of the differences of the divergence of Di(x,y,z) in the intervals $\Delta x$, $\Delta y$ and $\Delta z$ in I, J and K directions.

Next, for eqs. (6), (8) and (10), the following functionals (i=1, . . . , M) are used.

$$Ii(s) = \frac{1}{\sqrt{P_i}} I_i(s) \quad (21)$$

Here Pi is a power of the temperature gradient vector distribution Di(x,y,z) in the ROI (if possible, Pi is multiplied to the standard deviation of the respective power).

These are dealt with as functionals with respect to the temperature gradient vector distributions (or temperature distributions) s. Occasionally, Ii(s) is used instead of eq. (21). For instance, when the ROI is 3D, the functional is minimized with respect to the temperature gradient vector distribution Di(I,J,K) [or temperature distribution Ti(I,J,K)] (finite-element-approximated using the basis functions).

As the result, the simultaneous equations are derived for each temperature gradient vector distribution Di(I,J,K) [or temperature distribution Ti(I,J,K)]. By substituting the low-pass-filtered temperature gradient vector distributions data Di(I,J,K) [or temperature distributions data Ti(I,J,K)] and reference thermal conductivities (distributions) data k'(I,J,K) into the simultaneous equations for i=1, . . . , M, the following algebra equations are derived for the unknown thermal conductivity distribution k(I,J,K) (i.e., vector L').

$$BL' = b \quad (22)$$

Here, B and b are respectively matrix and vector composed of the used basis functions, measured temperature gradient vector distributions Di(I,J,K) (i=1, . . . , M) or temperature distribution data Ti(I,J,K) (i=1, . . . , M), and reference thermal conductivities (distributions) k'(I,J,K).

Next, using the algebra equations, the following functional is derived to be least-squares-minimized with respect to the unknown vector L' comprised of the unknown thermal conductivity distribution k(I,J,K).

$$II'(L') = \|b - BL'\|^2 \quad (23)$$

By minimizing this functional with respect to the unknown thermal conductivity distribution L'[k(I,J,K)], the following normal equations are derived.

$$B'L' = b' \quad (24)$$

where $B' = B^T B$, $b' = B^T b$.

By solving these, as the estimation result, k(x,y,z) is obtained. Here, the normal equations can also be derived by implementing the least-squares minimization with respect to the thermal conductivity distribution L" in the ROI to the algebra equations derived by minimizing the functional (21) with respect to the temperature gradient vector distribution Di(I,J,K) (or temperature distribution Ti(I,J,K)) in the ROI, after that the low-pass-filtered distributions of the temperature gradient vector Di(I,J,K) and divergence of the temperature gradient vector, and reference conductivities (distributions) ln k'(I,J,K) are substituted. The same as in the case when the ROI is 2D or 1D.

B and b in eqs. (24) are composed of the low-pass filtered distributions of the temperature gradient vector or temperature. Then, the inverse of the matrix B amplifies the high frequency noise remained in the vector b. Moreover, particularly when one temperature distribution is measured (M=1), the configurations of the thermal sources/sinks and reference regions possibly become improper ones. As the results, L' becomes unstable. Thus, occasionally the reconstruction (estimation) can be stabilized by the application of the regularization.

That is, the following penalty terms are considered in a continuous coordinate system, where the regularization parameters $\alpha_{1i}$, $\alpha_{2i}$ and $\alpha_{3i}$ (positive values) being able to be set for each measured temperature distribution Ti is used.

For 3D ROI, $$\int\int\int\left[\alpha_{1i}k^2 + \alpha_{2i}\left\{\left(\frac{\partial}{\partial x}k\right)^2 + \left(\frac{\partial}{\partial y}k\right)^2 + \left(\frac{\partial}{\partial z}k\right)^2\right\} + \alpha_{3i}\left\{\frac{\partial^2}{\partial x^2}k + \frac{\partial^2}{\partial y^2}k + \frac{\partial^2}{\partial z^2}k\right\}^2\right]dV. \quad (25)$$

For 2D ROI, $$\int\int\left[\alpha_{1i}k^2 + \alpha_{2i}\left\{\left(\frac{\partial}{\partial x}k\right)^2 + \left(\frac{\partial}{\partial y}k\right)^2\right\} + \alpha_{3i}\left\{\frac{\partial^2}{\partial x^2}k + \frac{\partial^2}{\partial y^2}k\right\}^2\right]dA. \quad (26)$$

For 1D ROI, $$\int\left[\alpha_{1i}k^2 + \alpha_{2i}\left\{\frac{\partial}{\partial x}k\right\}^2 + \alpha_{3i}\left\{\frac{\partial^2}{\partial x^2}k\right\}^2\right]dx. \quad (27)$$

That is, when the functionals (6), (8) and (10) are dealt with, the respective penalty terms (25) to (27) are finite-element-approximated using the same basis functions as those used for the finite-element approximating equations (6), (8) and (10). For instance, when the ROI is 3D, the functional II(L') [eq. (23)] added to the penalty terms is minimized with respect to L' after the reference conductivities (distributions) ln k'(I,J,K) are substituted into ln(I,J,K). Otherwise, the respective penalty terms (25) to (27) are finite-difference-approximated. Similarly, the functional II(L') [eq. (23)] added to the penalty terms is minimized with respect to L' after the reference conductivities (distributions) ln k'(I,J,K) are substituted into ln k(I,J,K).

As the result, for instance, when the ROI is 3D, the regularized simultaneous equations are derived for the unknown conductivity distribution k(I,J,K) (i.e., vector L').

$$(B' + \alpha_1 I + \alpha_2 G^T G + \alpha_3 G^T G G^T G)L' = b'$$

$$\alpha_1 = \Sigma_i \alpha_{1i}, \alpha_2 = \Sigma_i \alpha_{2i}, \, \alpha_3 = \Sigma_i \alpha_{3i} \quad (28)$$

By solving these equations, as the estimation result, k(I,J,K) is obtained. Here, respective $G^TG$ and $G^TGG^TG$ are the Laplacian and squared Laplacian operators approximated by the finite element or finite difference (discrete). The same as in the case when the ROI is 2D or 1D.

The regularization parameters $\alpha_1$, $\alpha_2$ and $\alpha_3$ in (28) can be set large such that the matrix multiplied to the vector L' becomes numerically positive definite. Alternatively, the values $\alpha_{1i}$, $\alpha_{2i}$ and $\alpha_{3i}$ can be set small and large respectively when the SNR (accuracy) of each measured temperature gradient distribution data is high and low (the SNR depends on the magnitude of the measured temperature gradient distribution). For instance, the values can be set proportional to the reciprocal of the SNR of the power of each measured temperature gradient distribution data. Here, the SNR of the temperature gradient distribution depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component distributions of each temperature gradient vector differ each other. Accordingly, $\alpha_{2i}$ and $\alpha_{3i}$ can also be set at different values for respective directions of the partial derivatives in eqs. (25) and (26). That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component distribution data. Furthermore, the absolute values of $\alpha_{2i}$ and $\alpha_{3i}$ can also be set small and large respectively when the data spatial distance is long and short (for instance, such that they becomes proportional to the reciprocal of the squared distance). Thus, these absolute values can also be set proportional to the product of the weighted absolute values determined by the respective factors determining the SNRs of each temperature gradient vector distribution and component distributions.

Here, the measurement of the SNR (accuracy) of the temperature measurement is performed to evaluate the accuracy of the measurement equipment. The SNR of the power can be estimated from the ratio of the squared mean and variance of the temperature distributions measured for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector distribution Di(x,y,z) over the ROI can be estimated from the temperature gradient vector data of the nodes (I,J,K) of each element.

The regularization parameters $\alpha_1$, $\alpha_2$ and $\alpha_3$ can also be set spatially varying in eqs (25) to (27). Thus, the values can be set large such that the local matrix multiplied to the thermal conductivity at each point of interest in vector L' becomes numerically positive definite. Alternatively, the values can be set small and large respectively when the SNR (accuracy) of each measured temperature gradient data of each point of interest is high and low (the SNR depends on the magnitude of the measured temperature gradient data. For instance, the values can be set proportional to the reciprocal of the SNR of the power of each measured temperature gradient data of each point. Here, the SNR of the temperature gradient data depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component data of each temperature gradient vector differ each other at each point. Accordingly, $\alpha_{2i}$ and $\alpha_{3i}$ can also be set at different values for respective directions of the partial derivatives in eqs. (25) and (26) as well as the positions. That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component data of each point. Furthermore, the absolute values of $\alpha_{2i}$ and $\alpha_{3i}$ can also be set small and large respectively when the data spatial distance is long and short (for instance, such that they becomes proportional to the reciprocal of the squared distance). Thus, these absolute values can also be set proportional to the product of the weighted absolute values determined by the respective factors determining the SNRs of each temperature gradient vector and components.

Here, the measurement of the SNR (accuracy) of the temperature measurement is performed to evaluate the accuracy of the measurement equipment. The SNR of the power can be estimated from the ratio of the squared mean and variance of the temperatures measured at each point for a flat black body having a constant temperature. Alternatively, to evaluate the accuracy of the measurement equipment and environment, by using the same environment or by realizing the same environment, the SNR can be estimated for the target itself or a black body. The SNR of the temperature gradient vector $Di(x,y,z)$ can be estimated for each nodes $(I,J,K)$ or each element.

The 3D ROI can be composed of 3D, 2D or 1D ROIs. The 2D ROI can be composed of 2D or 1D ROI. In such cases, the algebra equations can be derived for the low dimensional ROI and, however, the regularization can also be performed in the high dimensional ROI.

Next, the second principle is explained.

According to the second principle, the distribution of the thermal conductivity, the first order partial derivative of the thermal conductivity, or temperature gradient vector (or temperature or divergence of the temperature gradient vector) described in the first order partial differential equations (1) to (3) is finite-difference-approximated or finite-element-approximated (based on the Galerkin's method).

The distribution of the thermal conductivity $\ln k(x,y,z)$, the first order partial derivative of the thermal conductivity, or low-pass-filtered temperature gradient vector $Di(x,y,z)$ or low-pass-filtered temperature $Ti(x,y,z)$ described using the Cartesian coordinate system in the first order partial differential equations (1) to (3) is finite-difference-approximated or finite-element-approximated (based on the Galerkin's method) using the discrete coordinate system $(I,J,K) \sim (x/\Delta x, y/\Delta y, z/\Delta z)$ [i ($i=1, \ldots, M$) denotes the measured temperature Ti, where M is the number of the independent measured temperature distribution $(\geq 1)$].

When applying the finite difference (discrete) approximation to the first order partial differential equations (1) to (3), for instance, when the ROI is 3D, the finite difference approximation (forward or backward difference approximation etc.) is applied to the 3D thermal conductivity distribution $\ln k(x,y,z)$ in eqs. (1), the approximation of the temperature gradient vector distribution $Di(x,y,z)$ can be obtained by applying a differential filter to the low-pass filtered temperature data, or applying a differential filter with a cutoff frequency to the raw temperature measurement data, and the approximation of the divergence distribution of the temperature gradient vector can be obtained by applying such differential filters to the obtained distribution of the temperature gradient vector. The same as in the case when the ROI is 2D or 1D.

When applying the finite element approximation (based on Galerkin's method) to the first order partial differential equations (1) to (3), for instance, when the ROI is 3D, the 3D thermal conductivity distribution $\ln k(x,y,z)$, temperature gradient vector distribution $Di(x,y,z)$ or temperature distribution $Ti(x,y,z)$ is approximated using the basis functions. The same as in the case when the ROI is 2D or 1D.

The approximation of the temperature gradient vector distribution can be obtained by applying a differential filter to the low-pass filtered temperature data, or applying a differential filter with a cutoff frequency to the raw temperature measurement data, or applying the partial derivatives to the temperature distribution data expressed using basis functions, and the approximation of the divergence distribution of the temperature gradient vector can be obtained by applying such differential filters to the obtained distribution of the temperature gradient vector, or applying the partial derivatives to the obtained distribution of the temperature gradient vector expressed using basis functions.

When the temperature distributions Ti ($i=1, \ldots, M$) are measured and the finite difference (discrete) approximation is applied to the thermal conductivity distribution $L_{ln}$ and temperature gradient vector distributions expressed in the first order partial differential equations (1) to (3), for instance, when the ROI is 3D, by substituting into the approximated equations the low-pass-filtered distributions data of the temperature gradient vector $Di(I,J,K)$ [$i=1, \ldots, M$] and divergence of the temperature gradient vector, and reference thermal conductivities (distributions) data $\ln k'(I,J,K)$, the simultaneous equations are derived for the unknown thermal conductivity distribution $\ln k(I,J,K)$ (i.e., vector $L'_{ln}$).

$$C_i L'_{ln} = c_i \quad (29)$$

Here, Ci and ci are respectively matrix and vector composed of the coefficients of the used finite difference approximations of partial derivatives, measured temperature gradient vector distribution $Di(I,J,K)$, divergence distribution of the temperature gradient vector and reference thermal conductivities (distributions) $\ln k'(I,J,K)$ when temperature distribution Ti is measured.

Next, using the simultaneous equations, the following functional to be least-squares-minimized with respect to the unknown conductivity distribution $L'_{ln}$ is derived.

$$II(L'_{ln}) = \sum_i \frac{1}{P_i} \|c_i - C_i L'_{ln}\|^2 \quad (30)$$

$$\left( \text{or } II(L'_{ln}) = \sum_i \|c_i - C_i L'_{ln}\|^2 \right).$$

Here Pi is a power of the temperature gradient vector distribution $Di(x,y,z)$ in the ROI (if possible, Pi is multiplied to the standard deviation of the respective power).

By minimizing this functional with respect to the unknown conductivity distribution $L'_{ln}$, the following normal equations are derived.

$$C'L'_{ln} = c' \quad (31)$$

Here, $$C' = \sum_i \frac{1}{P_i} C_i^T C_i, \quad c' = \sum_i \frac{1}{P_i} C_i^T c_i.$$

By solving these, as the estimation result, $\ln k(I,J,K)$ is obtained. Here, the normal equations can also be derived by implementing the least-squares minimization with respect to the thermal conductivity distribution $L''_{ln}$ in the ROI to the simultaneous equations for $L''_{ln}$, after that the low-pass-filtered distributions of the temperature gradient vector $Di(I,J,K)$ and divergence of the temperature gradient vector, and reference conductivities (distributions) ln k'(I,J,K) are substituted. The same as in the case when the ROI is 2D or 1D.

When the temperature distributions Ti (i=1, ..., M) are measured and the finite element approximation is applied to the thermal conductivity distribution $L_{ln}$ or temperature gradient vector distribution s expressed in the first order partial differential equations (1) to (3), the functionals Ii(.) dealt with are shown for the case when the ROI is 3D, 2D and 1D.

For 3D ROI, $$I_i(\bullet) = \iiint \left[ D_{ix}\frac{\partial}{\partial x}(\ln k) + D_{iy}\frac{\partial}{\partial y}(\ln k) + D_{iz}\frac{\partial}{\partial z}(\ln k) + \frac{\partial}{\partial x}D_{ix} + \frac{\partial}{\partial y}D_{iy} + \frac{\partial}{\partial z}D_{iz} \right] v(x, y, z)dV, \quad (32)$$

where v(x,y,z) is arbitrary weight function satisfied with $|v(x,y,z)| \neq 0$.

For 2D ROI, $$I_i(\bullet) = \iint \left[ D_{ix}\frac{\partial}{\partial x}(\ln k) + D_{iy}\frac{\partial}{\partial y}(\ln k) + \frac{\partial}{\partial x}D_{ix} + \frac{\partial}{\partial y}D_{iy} \right] v(x, y)dA, \quad (33)$$

where v(x,y) is arbitrary weight function satisfied with $|v(x,y)| \neq 0$.

For 1D ROI, $$I_i(\bullet) = \int \left[ D_{ix}\frac{d}{dx}(\ln k) + \frac{d}{dx}D_{ix} \right] v(x)dx \quad (34)$$

where v(x) is arbitrary weight function satisfied with $|v(x)| \neq 0$.

When dealing with the functionals Ii(.) [(32) to (34)], the following functional is used (i=1, ..., M).

$$Ii(\bullet) = \frac{1}{\sqrt{P_i}} I_i(\bullet) \quad (35)$$

Here Pi is a power of the temperature gradient vector distribution Di(x,y,z) in the ROI (if possible, Pi is multiplied to the standard deviation of the respective power). Instead of eq. (35), Ii(s) can also be used.

As the weight function v in Ii(.) in IIi(.) [eq. (35)], the basis functions used for finite element approximating the thermal conductivity distribution $L_{ln}$, the first order partial derivative of the thermal conductivity, or temperature gradient vector distributions (or temperature distribution or divergence distribution of the temperature gradient vector) is used.

Furthermore, when temperature Ti is measured, the low-pass-filtered distributions of the temperature gradient vector Di(I,J,K) and divergence of the temperature gradient vector, and reference thermal conductivities (distributions) ln k'(I,J,K) are substituted into Iii(.) [eq. (35)], and by setting zero the substituted IIi(.), the following simultaneous equations are derived for the unknown thermal conductivity distribution $L'_{ln}$.

$$II_i(L'_{ln})=0,$$

i.e., $$D_i L'_{ln} = d_i \quad (36)$$

Here, when using the basis functions used for approximating the temperature gradient vector distribution s (or temperature distribution or divergence distribution of the temperature gradient vector) as the weight function and implementing the partial integration to the gradient of the thermal conductivity k(x,y,z), the basis functions for ink can be direct currents. Here, Di and di are respectively matrix and vector composed of the used basis functions, measured temperature gradient vector distribution data Di(I,J,K), divergence distribution data of the temperature gradient vector and reference thermal conductivities (distributions) data ln k'(I,J,K) when the temperature Ti is measured.

Next, the following functional is derived for least-squares minimizing the simultaneous equations (when one temperature distribution is measured) or algebra equations (when M temperature distributions are measured) with respect to the unknown thermal conductivity distribution ln k(I,J,K) (i.e., vector $L'_{ln}$).

$$II(L'_{ln}) = \Sigma_i \|d_i - D_i L'_{ln}\|^2 \quad (37)$$

By minimizing this functional with respect to the unknown conductivity distribution $L'_{ln}$, the following normal equations are derived.

$$D'L'_{ln} = d' \quad (38)$$

where $$D' = \Sigma_i D_i^T D_i, \ d' = \Sigma_i D_i^T d_i.$$

By solving these, as the estimation result, ln(x,y,z) is obtained. Here, the normal equations can also be derived by implementing the least-squares minimization with respect to the thermal conductivity distribution L" in the ROI to the simultaneous equations derived from the functional (35), after that the low-pass-filtered distributions of the temperature gradient vector Di(I,J,K) and divergence of the temperature gradient vector, and reference conductivities (distributions) ln k'(I,J,K) are substituted. The same as in the case when the ROI is 2D or 1D.

C' and c' in eqs. (31) [finite difference approximation] and D' and d' in eqs. (38) [finite element approximation] are composed of the low-pass filtered distributions of the temperature gradient vector or temperature. Then, the inverse of the matrixes C' and D' respectively amplify the high frequency noise remained in the vector c' and d'. Moreover, particularly when one temperature distribution is measured (M=1), the configurations of the thermal sources/sinks and reference regions possibly become improper ones. As the results, $L'_{ln}$ becomes unstable. Thus, occasionally the reconstruction (estimation) can be stabilized by the application of the regularization.

That is, the penalty terms (15) to (17) are considered in a continuous coordinate system, where the regularization parameters $\alpha_{1i}$, $\alpha_{2i}$ and $\alpha_{3i}$ (positive values) being able to be set for each measured temperature distribution Ti is used.

When applying the finite difference approximation, the respective penalty terms (15) to (17) are finite-difference-approximated (however, $\alpha_1=0$). For instance, when the ROI is 3D, the functional [eq. (30)] added to the penalty terms is minimized with respect to $L'_{ln}$ after the reference conductivities (distributions) ln k'(I,J,K) are substituted into ln k(I,J,K). As the result, the regularized simultaneous equations are derived for the unknown conductivity distribution ln k(I,J,K) (i.e., vector $L'_{ln}$).

$$(C'+\alpha_2 G^T G+\alpha_3 G^T G G^T G)L'_{ln}=c'$$

$$\alpha_2=\Sigma_i \alpha_{2i},\ \alpha_3=\Sigma_i \alpha_{3i} \quad (39)$$

By solving these, as the estimation result, ln k(x,y,z) is obtained. Here, respective $G^T G$ and $G^T G G^T G$ are the Laplacian and squared Laplacian operators approximated by the finite difference (discrete). The same as in the case when the ROI is 2D or 1D.

When applying the finite element approximation, the respective penalty terms (15) to (17) are finite-element-approximated using the same basis functions as those used for the finite-element approximating functional (35). For instance, when the ROI is 3D, the functional II($L'_{ln}$) [eq. (37)] added to the penalty terms is minimized with respect to $L'_{ln}$ after the reference conductivities (distributions) ln k'(I,J,K) are substituted into ln(I,J,K). Otherwise, the respective penalty terms (15) to (17) are finite-difference-approximated. Similarly, the functional II($L'_{ln}$) [eq. (37)] added to the penalty terms is minimized with respect to $L'_{ln}$ after the reference conductivities (distributions) ln k'(I,J,K) are substituted into ln k(I,J,K).

For both cases, the below regularized simultaneous equations are derived for the unknown conductivity distribution ln k(I,J,K) (vector $L'_{ln}$).

$$(D'+\alpha_1 I+\alpha_2 G^T G+\alpha_3 G^T G G^T G)L'_{ln}=d'$$

$$\alpha_1=\Sigma_i \alpha_{1i},\ \alpha_2=\Sigma_i \alpha_{2i},\ \alpha_3=\Sigma_i \alpha_{3i} \quad (40)$$

By solving these, as the estimation result, ln k(x,y,z) is obtained. Here, respective $G^T G$ and $G^T G G^T G$ are the Laplacian and squared Laplacian operators approximated by the finite element or finite difference (discrete). The same as in the case when the ROI is 2D or 1D.

The regularization parameters $\alpha_1$, $\alpha_2$ and $\alpha_3$ in (39) and (40) can be set large such that the matrix multiplied to the vector $L'_{ln}$ becomes numerically positive definite [here, $\alpha_1=0$ in (39)]. Alternatively, the values $\alpha_{1i}$, $\alpha_{2i}$ and $\alpha_{3i}$ can be set small and large respectively when the SNR (accuracy) of each measured temperature gradient distribution data is high and low (the SNR depends on the magnitude of the measured temperature gradient distribution). For instance, the values can be set proportional to the reciprocal of the SNR of the power of each measured temperature gradient distribution data. Here, the SNR of the temperature gradient distribution depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component distributions of each temperature gradient vector differ each other. Accordingly, $\alpha_{2i}$ and $\alpha_{3i}$ can also be set at different values for respective directions of the partial derivatives in eqs. (15) and (16). That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component distribution data. Furthermore, the absolute values of $\alpha_{2i}$ and $\alpha_{3i}$ can also be set small and large respectively when the data spatial distance is long and short (for instance, such that they becomes proportional to the reciprocal of the squared distance). Thus, these absolute values can also be set proportional to the product of the weighted absolute values determined by the respective factors determining the SNRs of each temperature gradient vector distribution and component distributions.

Here, the measurement of the SNR (accuracy) of the temperature measurement is performed to evaluate the accuracy of the measurement equipment. The SNR of the power can be estimated from the ratio of the squared mean and variance of the temperature distributions measured for a flat black body having a constant temperature. Alternatively, to evaluate the accuracy of the measurement equipment and environment, by using the same environment or by realizing the same environment, the SNR can be estimated for the target itself or a black body.

The SNR of the temperature gradient vector distribution Di(x,y,z) over the ROI can be estimated from the temperature gradient vector data of the discrete coordinates (I,J,K) for the finite difference approximation case and those of the nodes (I,J,K) of each element for the finite element approximation case.

The regularization parameters $\alpha_1$, $\alpha_2$ and $\alpha_3$ can also be set spatially varying in eqs (15) to (17). Thus, the values can be set large such that the local matrix multiplied to the thermal conductivity at each point of interest in vector $L'_{ln}$ becomes numerically positive definite [here, $\alpha_1=0$ in (39)]. Alternatively, the values can be set small and large respectively when the SNR (accuracy) of each measured temperature gradient data of each point of interest is high and low (the SNR depends on the magnitude of the measured temperature gradient data. For instance, the values can be set proportional to the reciprocal of the SNR of the power of each measured temperature gradient data of each point. Here, the SNR of the temperature gradient data depends on the measured temperature distribution data itself and the spatial intervals of the data (i.e., the direction of the gradient of the temperature and magnitudes of the gradient vector components). In addition, the SNR also depends on the direction of the aperture. Thus, the SNRs of the component data of each temperature gradient vector differ each other at each point. Accordingly, $\alpha_{2i}$ and $\alpha_{3i}$ can also be set at different values for respective directions of the partial derivatives in eqs. (15) and (16) as well as the positions. That is, the absolute values of $\alpha_{2i}$ and $\alpha_{3i}$ for the respective directions of the partial derivatives can be set small and large respectively when the SNR (accuracy) of the measured temperature gradient component distribution data is high and low. For instance, the values can be set proportional to the reciprocal of the square root of the SNR of the power of the measured temperature gradient component data of each point. Furthermore, the absolute values of $\alpha_{2i}$ and $\alpha_{3i}$ can also be set small and large respectively when the data spatial distance is long and short (for instance, such that they becomes proportional to the reciprocal of the squared distance). Thus, these absolute values can also be set proportional to the product of the weighted absolute values determined by the respective factors determining the SNRs of each temperature gradient vector and components.

Here, the measurement of the SNR (accuracy) of the temperature measurement is performed to evaluate the accuracy of the measurement equipment. The SNR of the power can be estimated from the ratio of the squared mean and variance of the temperatures measured at each point for a flat black body having a constant temperature. Alternatively, to evaluate the accuracy of the measurement equipment and environment, by using the same environment or by realizing the same environment, the SNR can be estimated for the target itself or a black body.

When using the finite difference approximation, the SNR of the temperature gradient vector Di(I,J,K) of each point (I,J,K) is required, whereas when finite element approximation, the SNR of the temperature gradient vector of each node (I,J,K) or each element is required.

When the Galerkin's method is applied after eqs. (1) to (3) are respectively multiplied by k(x,y,z), k(x,y) and k(x), the functionals are similarly finite-element-approximated using as the weight function the same basis functions as those used for approximating the thermal conductivity distribution, first order partial derivative distribution of the thermal conductivity or temperature gradient vector distribution (or temperature distribution or divergence distribution of the temperature gradient vector) together with the penalty terms (25) to (27) for regularization. As the result, the simultaneous equations (40) are derived for the unknown thermal conductivity distribution L'.

Here, Pi in functional (35) is a summation of the power of the inner product distribution of the temperature gradient vector Di(x,y,z) and gradient operator for k(x,y,z) in the ROI (if possible, multiplied to the standard deviation of the respective power) and the power of the divergence distribution of Di(x,y,z) in the ROI (if possible, multiplied to the standard deviation of the respective power). The regularization parameters can be, for instance, set proportional to the reciprocal of the SNR of the power determined by the accuracy (SNR) of the products of the temperature gradient vector Di(x,y,z) components and partial derivative operator in the same direction and the accuracy (SNR) of the divergence components of Di(x,y,z). Otherwise, the parameters can also be set proportional to the reciprocal of the SNR of the power determined by the accuracy (SNR) of the differences of the inner product of Di(x,y,z) and gradient operator in the intervals $\Delta x$, $\Delta y$ and $\Delta z$ in I, J and K directions and the accuracy (SNR) of the differences of the divergence of Di(x,y,z) in the intervals $\Delta x$, $\Delta y$ and $\Delta z$ in I, J and K directions.

The 3D ROI can be composed of 3D, 2D or 1D ROIs. The 2D ROI can be composed of 2D or 1D ROI. In such cases, the algebra equations can be derived for the low dimensional ROI and, however, the regularization can also be performed in the high dimensional ROI.

Next, the third principle is explained.

According to the first and second principles, the utilization of the measured in the ROI temperature distributions Ti [i (=1, ..., M) denotes the measured temperature distribution Ti, where M is the number of the independent measured temperature distribution data ($\geq 1$)] or temperature gradient vector distributions Di and reference thermal conductivities (distributions) given in the reference regions or points $w_m$ (m=1, ..., N) [i.e., eqs. (4)] and application of the specified numerical solutions [i.e., using the finite element method (calculus of variations or Galerkin's method) or finite difference method and regularization] to the first order partial differential equations (1) to (3) of the thermal conductivity distribution k in the 3D, 2D or 1D ROI [i.e., $\nabla(kD_i)=0$, where $D_i=-\nabla T_i$] yields the estimate of the unknown thermal conductivity distribution k.

In contrast, according to the third principle, in the case where the temperature distributions and the positions, magnitudes, conditions and numbers of the thermal sources/sinks or reference regions/points are temporally changeable in the 3D, 2D or 1D ROI, the temporally changeable distributions of the thermal conductivity, density, specific heat, product of the density and specific heat, diffusivity, ratio of the diffusivity and density, or ratio of the diffusivity and specific heat can be estimated.

(I) According to the first and second principles, for instance, when the ROI is 3D, by using the sequences of temperature distributions Ti(x,y,z,t), sequences of the temporal first order partial derivative distributions of the temperature $dT_i(x,y,z,t)/dt$ and sequences of the temperature gradient vector distributions Di(x,y,z,t), the following first order partial differential equations are dealt with.

$$\rho_i c_i \frac{\partial T_i}{\partial t} = -\nabla(k_i D_i) \tag{41}$$

where, $D_i(x,y,z,t)=-\nabla T_i(x,y,z,t)$.

Furthermore, the following initial conditions being possibly dependent of the sequence i and time t can be dealt with, $k_i(x,y,z,t)=k'_i(x,y,z,t)$ and/or $\rho_i c_i(x,y,z,t)=\rho'_i c'_i(x,y,z,t)$ $(x,y,z) \in w_{m(t)}$ $(m(t)=1 \sim N(t))$. (42)

Here, t denotes the time after starting the temperature distribution data acquisition, and i (=1, ..., M) denotes the independent measured sequence of the temperature distributions Ti(x,y,z,t), where M is the number of the independent measured sequences ($\geq 1$). ki denotes the sequence of the thermal conductivity distributions ki(x,y,z,t), thermal conductivity distribution ki(x,y,z) or k(x,y,z). $\rho_i$ denotes the sequence of the density distribution $\rho_i(x,y,z,t)$, density distribution $\rho_i(x,y,z)$ or $\rho(x,y,z)$. $c_i$ denotes the sequence of the specific heat distribution $c_i(x,y,z,t)$, specific heat distribution $c_i(x,y,z)$ or $c(x,y,z)$).

In eqs. (41), the measured data and typical data can be given in the ROI for the sequences of the thermal conductivity distributions $k_i(x,y,z,t)$, thermal conductivity distributions $k_i(x,y,z)$ or $k(x,y,z)$, sequences of the density distributions $\rho_i(x,y,z,t)$, density distributions $\rho_i(x,y,z)$ or $\rho(x,y,z)$, sequences of the specific heat distributions $c_i(x,y,z,t)$, specific heat distributions $c_i(x,y,z)$ or $c(x,y,z)$, sequences of the product distributions of the density and specific heat $\rho_i(x,y,z,t)c_i(x,y,z,t)$, $\rho_i(x,y,z,t)c_i(x,y,z)$, $\rho_i(x,y,z,t)c(x,y,z)$, $\rho_i(x,y,z)c_i(x,y,z,t)$ or $\rho(x,y,z)c_i(x,y,z,t)$ [hereafter, these are described as $\rho c_i(x,y,z,t)$], product distributions of the density and specific heat $\rho_i(x,y,z)c_i(x,y,z)$, $\rho_i(x,y,z)c(x,y,z)$, or $\rho(x,y,z)c_i(x,y,z)$ [hereafter, these are described as $\rho c_i(x,y,z)$] or $\rho(x,y,z)c(x,y,z)$ [hereafter, this is described as $\rho c(x,y,z)$]. Otherwise, these can be dealt with as unknown.

Therefore, the sequences of the thermal diffusivity distributions $h_0 i(x,y,z,t)$ [$k_i(x,y,z,t)/\rho c_i(x,y,z,t)$, $k_i(x,y,z,t)/\rho c_i(x,y,z)$, $k_i(x,y,z,t)/\rho c(x,y,z)$, $k_i(x,y,z)/\rho c_i(x,y,z,t)$, $k(x,y,z)/\rho c_i(x,y,z,t)$], thermal diffusivity distributions $h_0 i(x,y,z)$ [$k_i(x,y,z)/\rho c_i(x,y,z)$, $k_i(x,y,z)/\rho c(x,y,z)$, $k(x,y,z)/\rho c_i(x,y,z)$] or thermal diffusivity distribution $h_0(x,y,z)$ [$k(x,y,z)/\rho c(x,y,z)$] can be obtained. Here, occasionally the temporal first order partial derivative of temperature $dT_i(x,y,z,t)/dt$ in the left hand of eqs. (41) is approximately set to zero.

Otherwise, when in the ROI the sequences of the product distributions of the density and specific heat $\rho c_i(x,y,z,t)$, product distributions of the density and specific heat $\rho c_i(x,y,z)$ or $\rho c(x,y,z)$ are regarded as spatially homogeneous (though unknown), i.e., these are respectively expressed as $\rho c_i(t)$, $\rho c_i$ or $\rho c$, instead of eqs. (41), the following first order partial differential equations for the unknown thermal diffusivity $h_0$ in the ROI [sequences of the thermal diffusivity distributions $h_{0i}(x,y,z,t)$, thermal diffusivity distributions $h_{0i}(x,y,z)$ or $h_0(x,y,z)$] are dealt with, i.e., $$\frac{\partial T_i}{\partial t} = -\nabla(h_{0i}D_i) \tag{43}$$

together with the following initial conditions being possibly dependent of the sequences i and time t (occasionally, dealt with as constant with respect to i and t) instead of eqs. (42), i.e., $$h_{0i}(x,y,z,t)=h'_{0i}(x,y,z,t) \tag{44}$$

$$(x,y,z) \in w_{m(t)} \ (m(t)=1 \sim N(t)).$$

Here, occasionally the temporal first order partial derivative of temperature $dT_i(x,y,z,t)/dt$ in the left hand of eqs. (43) is approximately set to zero.

Otherwise, when in the ROI the sequences of the density distributions $\rho_i(x,y,z,t)$, density distributions $\rho_i(x,y,z)$ or $\rho(x,y,z)$ are regarded as spatially homogeneous (though unknown), instead of eqs. (41), the following first order partial differential equations for the unknown, ratio of the thermal conductivity and density $h_1$ in the ROI [sequences of the ratio distributions of the thermal conductivity and density $h_{1i}(x,y,z,t)$, ratio distributions of the thermal conductivity and density $h_{1i}(x,y,z)$ or $h_1(x,y,z)$] or specific heat [sequences of the specific heat distributions $c_i(x,y,z,t)$, specific heat distributions $c_i(x,y,z)$ or $c_i(x,y,z)$] are dealt with, i.e., $$c_i \frac{\partial T_i}{\partial t} = -\nabla(h_{1i}D_i) \tag{45}$$

together with the following initial conditions being possibly dependent of the sequences i and time t (occasionally, dealt with as constant with respect to i and t) instead of eqs. (42), i.e., $$h_{1i}(x,y,z,t)=h'_{1i}(x,y,z,t)$$

and/or $$c_i(x,y,z,t)=c'_i(x,y,z,t)$$

$$(x,y,z) \in w_{m(t)} \ (m(t)=1 \sim N(t)). \tag{46}$$

Here, occasionally the temporal first order partial derivative of temperature $dT_i(x,y,z,t)/dt$ in the left hand of eqs. (45) is approximately set to zero.

Otherwise, when in the ROI the sequences of the specific heat distributions $c_i(x,y,z,t)$, specific heat distributions $c_i(x,y,z)$ or $c(x,y,z)$ are regarded as spatially homogeneous (though unknown), instead of eqs. (41), the following first order partial differential equations for the unknown, ratio of the thermal conductivity and specific heat $h_2$ in the ROI [sequences of the ratio distributions of the thermal conductivity and specific heat $h_{2i}(x,y,z,t)$, ratio distributions of the thermal conductivity and specific heat $h_{2i}(x,y,z)$ or $h_2(x,y,z)$] or density [sequences of the density distributions $\rho_i(x,y,z,t)$, density distributions $\rho_i(x,y,z)$ or $\rho(x,y,z)$] are dealt with, i.e., $$\rho_i \frac{\partial T_i}{\partial t} = -\nabla(h_{2i}D_i) \tag{47}$$

together with the following initial conditions being possibly dependent of the sequences i and time t (occasionally, dealt with as constant with respect to i and t) instead of eqs. (42), i.e., $$h_{2i}(x,y,z,t)=h'_{2i}(x,y,z,t)$$

and/or $$\rho_i(x,y,z,t)=\rho_i(x,y,z,t)$$

$$(x,y,z) \in w_{m(t)} \ (m(t)=1 \sim N(t)). \tag{48}$$

Here, occasionally the temporal first order partial derivative of temperature $dT_i(x,y,z,t)/dt$ in the left hand of eqs. (47) is approximately set to zero.

The same as in the case when the ROI is 2D or 1D.

Thus, the 3D, 2D or 1D ROI is composed of the finite continuous regions of the below unknown thermal property distributions (hereafter, the continuous region is referred to as a composition region). That is, the measurement targets are at least one of the following distributions in the 3D, 2D or 1D composition regions, i.e., the thermal conductivity distributions $L_{ij}$ [$k_i(x,y,z,t)$ in 3D composition region, $k_i(x,y,t)$ in 2D composition region and $k_i(x,t)$ in 1D composition region], $L_i$ [$k_i(x,y,z)$, $k_i(x,y)$, $k_i(x)$] and L [$k(x,y,z)$, $k(x,y)$, $k(x)$], product distributions of density and specific heat $R_{ij}$ [$\rho c_i(x,y,z,t)$, $\rho c_i(x,y,t)$, $\rho c_i(x,t)$], $R_i$ [$\rho c_i(x,y,z)$, $\rho c_i(x,y)$, $\rho c_i(x)$] and R [$\rho c(x,y,z)$, $\rho c(x,y)$, $\rho c(x)$], density distributions $S_{ij}$ [$\rho_i(x,y,z,t)$, $\rho_i(x,y,t)$, $\rho_i(x,t)$], $S_i$ [$\rho_i(x,y,z)$, $\rho_i(x,y)$, $\rho_i(x)$] and S [$\rho(x,y,z)$, $\rho(x,y)$, $\rho(x)$], and specific heat distributions $S_{ij}$ [$c_i(x,y,z,t)$, $c_i(x,y,t)$, $c_i(x,t)$], $S_i$ [$c_i(x,y,z)$, $c_i(x,y)$, $c_i(x)$] and S [$c(x,y,z)$, $c(x,y)$, $c(x)$], thermal diffusivity distributions $H_{0ij}$ [$h_{0i}(x,y,z,t)$, $h_{0i}(x,y,t)$, $h_{0i}(x,t)$], $H_{0i}$ [$h_{0i}(x,y,z)$, $h_{0i}(x,y)$, $h_{0i}(x)$] and $H_0$ [$h_0(x,y,z)$, $h_0(x,y)$, $h_0(x)$], ratio distributions of the thermal conductivity and density $H_{1ij}$ [$h_{1i}(x,y,z,t)$, $h_{1i}(x,y,t)$, $h_{1i}(x,t)$], $H_{1i}$ [$h_{1i}(x,y,z)$, $h_{1i}(x,y)$, $h_{1i}(x)$] and $H_1$ [$h_1(x,y,z)$, $h_1(x,y)$, $h_1(x)$], ratio distributions of the thermal conductivity and specific heat $H_{2ij}$ [$h_{2i}(x,y,z,t)$, $h_{2i}(x,y,t)$, $h_{2i}(x,t)$], $H_{2i}$ [$h_{2i}(x,y,z)$, $h_{2i}(x,y)$, $h_{2i}(x)$] and $H_2$ [$h_2(x,y,z)$, $h_2(x,y)$, $h_2(x)$]. Thus, the composition regions include other composition regions each other. When there exists only one composition region, the composition region is the ROI itself.

Hereafter, the temporal coordinate t is approximated as $j \sim t/\Delta t$ ($j=0, \ldots, n$) using the discrete temporal coordinate j, and the spatial coordinate $(x,y,z,i,t)$ is approximated as $(I,J,K,i,j) \sim (x/\Delta x, y/\Delta y, z/\Delta z, i, t/\Delta t)$.

Accordingly, when the ROI is 3D and eqs. (41) and (42) are dealt with, the sequences of the 3D thermal conductivity distributions $ki(x,y,z,t)$, 3D thermal conductivity distributions $ki(x,y,z)$ or $k(x,y,z)$ are finite-element-approximated or finite-difference-approximated using the discrete coordinate system $(I,J,K,i,j) \sim (x/\Delta x, y/\Delta y, z/\Delta z, i, t/\Delta t)$.

When both 3D density distributions [sequences $\rho_i(x,y,z,t)$, distributions $\rho_i(x,y,z)$ or $\rho(x,y,z)$] and 3D specific heat distributions [sequences $c_i(x,y,z,t)$, distributions $c_i(x,y,z)$ or $c(x,y,z)$] are given or not, the sequences of the 3D product distributions of the density and specific heat or 3D product distributions of the density and specific heat are respectively finite-element-approximated or finite-difference-approximated as $\rho c_i(I,J,K,j)$ and $\rho c_i(I,J,K)$ or $\rho c(I,J,K)$.

When either 3D density distributions [sequences $\rho_i(x,y,z,t)$, distributions $\rho_i(x,y,z)$ or $\rho(x,y,z)$] or 3D specific heat distributions [sequences $c_i(x,y,z,t)$, distributions $c_i(x,y,z)$ or $c(x,y,z)$] is given, the sequences of the 3D density distributions $\rho_i(x,y,z,t)$, 3D density distributions $\rho_i(x,y,z)$ or $\rho(x,y,z)$, and the sequences of the 3D specific heat distributions $c_i(x,y,z,t)$, 3D specific heat distributions $c_i(x,y,z)$ or $c(x,y,z)$ are respectively finite-element-approximated or finite-difference-approximated as $\rho c_i(I,J,K,j)$ and $\rho c_i(I,J,K)$ or $\rho c(I,J,K)$.

When the ROI is 3D and eqs. (43) and (44) are dealt with, the sequences of the 3D thermal diffusivity distributions $h_{0i}(x,y,z,t)$, 3D thermal diffusivity distributions $h_{0i}(x,y,z)$ or $h_0(x,y,z)$ are finite-element-approximated or finite-difference-approximated.

When the ROI is 3D and eqs. (45) and (46) are dealt with, the sequences of the 3D ratio distributions of thermal conductivity and density $h_{1i}(x,y,z,t)$, 3D ratio distributions of the thermal conductivity and density $h_{1i}(x,y,z)$ or $h_1(x,y,z)$, and sequences of the 3D specific distributions $c_i(x,y,z,t)$, 3D specific distributions $c_i(x,y,z)$ or $c(x,y,z)$ are finite-element-approximated or finite-difference-approximated.

When the ROI is 3D and eqs. (47) and (48) are dealt with, the sequences of the 3D ratio distributions of thermal conductivity and specific heat $h_{2i}(x,y,z,t)$, 3D ratio distributions of the thermal conductivity and specific heat $h_{2i}(x,y,z)$ or $h_2(x,y,z)$, and sequences of the 3D density distributions $\rho_i(x,y,z,t)$, 3D density distributions $\rho_i(x,y,z)$ or $\rho_2(x,y,z)$ are finite-element-approximated or finite-difference-approximated.

When the distributions of the temporal first order partial derivative $dT_i(x,y,z,t)/dt$ and spatial derivatives of the measured temperature $T_i(x,y,z,t)$ [i (=1, ..., M) denotes the measured sequence of the temperature distributions $Ti(x,y,z,t)$, where M is the number of the independent measured sequences of the temperature distributions data ($\geq 1$)] are finite-element-approximated (calculus of variations or Galerkin's method) or finite-difference-approximated, the sequence of the 3D temperature distributions $Ti(x,y,z,t)$ can be evaluated as (a)~(c).

(a) approximated using the measured sequence of 3D nodal temperature distributions $T_i(I,J,K,j)$ and the 3D basis functions having the spatial coordinate as variables.

(b) approximated using the measured sequence of 3D nodal temperature distributions $T_i(I,J,K,j)$ and the 4D basis functions having the spatial and temporal coordinate as variables. Here, the basis functions are required to be differentiable with respect to t more than once.

(c) when the temporal first order partial derivative $dT_i(x,y,z,t)/dt$ and spatial derivatives of the sequence of the 3D temperature distributions $Ti(x,y,z,t)$ is finite-difference-approximated, $T_i(x,y,z,t)$ is approximated using the sequence of the 3D nodal temperature distributions $T_i(I,J,K,j)$ as $T_i(x,y,z,t) \sim T_i(I,J,K,j)$.

Thus, the sequence of the temporal first partial derivative distributions $dT_i(x,y,z,t)/dt$ of the sequence of the 3D temperature distributions $T_i(x,y,z,t)$ is evaluated as follows.

In case (a), the sequence of the temporal first partial derivative distributions $dT_i/dt(x,y,z,t)$ is approximated using the prespecified 3D basis functions and $dT_i/dt(I,J,K,j)$ obtained by applying the differential filter in j direction to the measured sequence of the 3D nodal temperature distributions $T_i(I,J,K,j)$, before which is low-pass-filtered in j direction or spatiotemporal I,J,K,j directions, or obtained by applying the differential filter in j direction to the sequence of the 3D nodal temperature distributions $T_i(I,J,K,j)$ with cutoff frequencies in j direction or spatiotemporal directions I,J,K,j.

In case (b), the sequence of the temporal first partial derivative distributions $dT_i/dt(x,y,z,t)$ is approximated by implementing the partial derivative with respect to t to $Ti(x,y,z,t)$ approximated using the prespecified 4D basis functions and $Ti(I,J,K,j)$, before which is low-pass-filtered in j direction or spatiotemporal I,J,K,j.

In case (c), the sequence of the temporal first partial derivative distributions $dT_i/dt(x,y,z,t)$ is approximated using $dT_i/dt(I,J,K,j)$ obtained by applying the differential filter in j direction to the measured sequence of the 3D nodal temperature distributions $T_i(I,J,K,j)$, before which is low-pass-filtered in j direction or spatiotemporal I,J,K,j directions, or obtained by applying the differential filter in j direction to the sequence of the 3D nodal temperature distributions $T_i(I,J,K,j)$ with cutoff frequencies in j direction or spatiotemporal directions I,J,K,j.

Furthermore, the sequence of the 3D temperature gradient vector distributions $Di(x,y,z,t)$ $(=[D_{ix}(x,y,z,t),D_{iy}(x,y,z,t),D_{iz}(x,y,z,t)]^T)$ is evaluated as follows.

In case (a), the sequence of the 3D temperature gradient vector distributions $Di(x,y,z,t)$ $(=[D_{ix}(x,y,z,t),D_{iy}(x,y,z,t),D_{iz}(x,y,z,t)]^T)$ is approximated using the prespecified 3D basis functions and $Di(I,J,K,j)$ obtained by applying the differential filter in respective I,J,K directions to the measured sequence of the 3D nodal temperature distributions $T_i(I,J,K,j)$, before which is low-pass-filtered in spatial I,J,K directions or spatiotemporal I,J,K,j directions, or obtained by applying the differential filter in respective spatial I,J,K directions to the sequence of the 3D nodal temperature distributions $T_i(I,J,K,j)$ with cutoff frequencies in spatial I,J,K directions or spatiotemporal directions I,J,K,j. Otherwise, the sequence of the 3D temperature gradient vector distributions $Di(x,y,z,t)$ $(=[D_{ix}(x,y,z,t),D_{iy}(x,y,z,t),D_{iz}(x,y,z,t)]^T)$ is approximated by implementing the partial derivatives in respective x,y,z directions the sequence of the 3D temperature distributions $Ti(x,y,z,t)$ approximated using the prespecified 3D basis functions and $Ti(I,J,K,j)$ low-pass-filtered in spatial I,J,K directions or spatiotemporal I,J,K,j directions.

In case (b), the sequence of the 3D temperature gradient vector distributions $Di(x,y,z,t)$ $(=[D_{ix}(x,y,z,t),D_{iy}(x,y,z,t),D_{iz}(x,y,z,t)]^T)$ is approximated using the prespecified 4D basis functions and $Di(I,J,K,j)$ obtained by applying the differential filter in respective I,J,K directions to the measured sequence of the 3D nodal temperature distributions $T_i(I,J,K,j)$, before which is low-pass-filtered in spatial I,J,K directions or spatiotemporal I,J,K,j directions, or obtained by applying the differential filter in respective spatial I,J,K directions to the sequence of the 3D nodal temperature distributions $T_i(I,J,K,j)$ with cutoff frequencies in spatial I,J,K directions or spatiotemporal directions I,J,K,j. Otherwise, the sequence of the 3D temperature gradient vector distributions $Di(x,y,z,t)$ $(=[D_{ix}(x,y,z,t),D_{iy}(x,y,z,t),D_{iz}(x,y,z,t)]^T)$ is approximated by implementing the partial derivatives in respective x,y,z directions the sequence of the 3D temperature distributions $Ti(x,y,z,t)$ approximated using the prespecified 4D basis functions and $Ti(I,J,K,j)$ low-pass-filtered in spatial I,J,K directions or spatiotemporal I,J,K,j directions.

In case (c), the sequence of the 3D temperature gradient vector distributions $Di(x,y,z,t)$ $(=[D_{ix}(x,y,z,t),D_{iy}(x,y,z,t),D_{iz}(x,y,z,t)]^T)$ is approximated using $Di(I,J,K,j)$ obtained by applying the differential filter in respective I,J,K directions to the measured sequence of the 3D nodal temperature distributions $T_i(I,J,K,j)$, before which is low-pass-filtered in spatial I,J,K directions or spatiotemporal I,J,K,j directions, or obtained by applying the differential filter in respective spatial I,J,K directions to the sequence of the 3D nodal temperature distributions $T_i(I,J,K,j)$ with cutoff frequencies in spatial I,J,K directions or spatiotemporal directions I,J,K,j.

Furthermore, the sequence of the divergence distributions of the 3D temperature gradient vector $D_i(x,y,z,t)$ ($=[D_{ix}(x,y,z,t),D_{iy}(x,y,z,t),D_{iz}(x,y,z,t)]^T$) is evaluated as follows.

In case (a), the sequence of the divergence distributions is approximated using the prespecified 3D basis functions and sequence of the nodal divergence distributions obtained by applying the differential filter in respective I,J,K directions to the measured sequence of the 3D nodal temperature gradient vector distributions $D_i(I,J,K,j)$, before which is low-pass-filtered in spatial I,J,K directions or spatiotemporal I,J,K,j directions, or obtained by applying the differential filter in respective spatial I,J,K directions to the sequence of the 3D nodal temperature gradient vector distributions $D_i(I,J,K,j)$ with cutoff frequencies in spatial I,J,K directions or spatiotemporal directions I,J,K,j. Otherwise, the sequence of the divergence distributions is approximated by implementing the partial derivatives twice in respective x,y,z directions the sequence of the 3D temperature distributions $T_i(x,y,z,t)$ approximated using the prespecified 3D basis functions and $T_i(I,J,K,j)$ low-pass-filtered in spatial I,J,K directions or spatiotemporal I,J,K,j directions.

In case (b), the sequence of the divergence distributions is approximated using the prespecified 4D basis functions and sequence of the nodal divergence distributions obtained by applying the differential filter in respective I,J,K directions to the measured sequence of the 3D nodal temperature gradient vector distributions $D_i(I,J,K,j)$, before which is low-pass-filtered in spatial I,J,K directions or spatiotemporal I,J,K,j directions, or obtained by applying the differential filter in respective spatial I,J,K directions to the sequence of the 3D nodal temperature gradient vector distributions $D_i(I,J,K,j)$ with cutoff frequencies in spatial I,J,K directions or spatiotemporal directions I,J,K,j. Otherwise, the sequence of the divergence distributions is approximated by implementing the partial derivatives twice in respective x,y,z directions the sequence of the 3D temperature distributions $T_i(x,y,z,t)$ approximated using the prespecified 4D basis functions and $T_i(I,J,K,j)$ low-pass-filtered in spatial I,J,K directions or spatiotemporal I,J,K,j directions.

In case (c), the sequence of the divergence distributions is approximated using sequence of the nodal divergence distributions obtained by applying the differential filter in respective I,J,K directions to the measured sequence of the 3D nodal temperature gradient vector distributions $D_i(I,J,K,j)$, before which is low-pass-filtered in spatial I,J,K directions or spatiotemporal I,J,K,j directions, or obtained by applying the differential filter in respective spatial I,J,K directions to the sequence of the 3D nodal temperature gradient vector distributions $D_i(I,J,K,j)$ with cutoff frequencies in spatial I,J,K directions or spatiotemporal directions I,J,K,j.

When the composition region is 2D or 1D, the 2D or 1D basis functions are used.

According to the first principle, in each composition region in the ROI, at least one of the spatial differential equations (41), (43), (45) and (47) expressing each unknown distributions is finite-element-approximated or discrete-approximated (based on the calculus of variations) [i.e., (a) or (b)], and by dealing with all the derived algebra equations, the simultaneous equations are derived for the unknown nodal vector U' over the ROI (Occasionally the ROI has composition regions having the same regions each other. If there exists only one composition region, the composition region is the ROI itself).

That is, according to the first principle, when the distributions Q, i.e., the thermal conductivity distributions Lij [$k_i(x,y,z,t)$ in 3D composition regions, $k_i(x,y,t)$ in 2D composition regions and $k_i(x,t)$ in 1D composition regions], Li [$k_i(x,y,z)$ in 3D composition regions, $k_i(x,y)$ in 2D composition regions and $k_i(x)$ in 1D composition regions] or L [$k(x,y,z)$ in 3D composition regions, $k(x,y)$ in 2D composition regions and $k(x)$ in 1D composition regions] expressed in the first order partial differential equations (41) in the 3D, 2D or 1D composition regions, are finite-element-approximated or discrete-approximated (based on the calculus of variations) [i.e., (a) or (b)], the functionals at time t are derived as $I_{ij}(L_{ij})$, $I_{ij}(L_i)$ or $I_{ij}(L)$ [eq. (49)] by adding $$\rho_i c_i \frac{\partial T_i}{\partial t} k_i$$

to the integral kernels of the functionals $I_i(L)$ at time t [i.e., integral kernels in eq. (5') in 3D composition regions, eq. (7') in 2D composition regions and eq. (9') in 1D composition regions, where k is ki].

Otherwise, according to the first principle, when the distributions Q, i.e., the first order partial derivative distributions of the thermal conductivity in the 1D composition regions, i.e., $dk_i(x,t)/dx$, $dk_i(x)/dx$ or $dk(x,y)/dx$, expressed in the first order partial differential equations (41) in the 1D composition regions, are finite-element-approximated or discrete-approximated (based on the calculus of variations) [i.e., (a) or (b)], the functional at time t is derived as $I_{ij}(.)$ [eq. (50)] by adding $$\rho_i c_i \frac{\partial T_i}{\partial t} \frac{\partial k_i}{\partial x}$$

to the integral kernels of the functionals $I_i(L)$ at time t [i.e., integral kernel in the second eq. in (9'), where k is ki].

Otherwise, according to the first principle, when the distributions Q, i.e., the product distributions of the density and specific heat Rij [$\rho c_i(x,y,z,t)$ in 3D composition regions, $\rho c_i(x,y,t)$ in 2D composition regions and $\rho c_i(x,t)$ in 1D composition regions], $R_i$ [$\rho c_i(x,y,z)$ in 3D composition regions, $\rho c_i(x,y)$ in 2D composition regions and $\rho c_i(x)$ in 1D composition regions] or R [$\rho c(x,y,z)$ in 3D composition regions, $\rho c(x,y)$ in 2D composition regions and $\rho c(x)$ in 1D composition regions] expressed in the first order partial differential equations (41) in the 3D, 2D or 1D composition regions, are finite-element-approximated or discrete-approximated (based on the calculus of variations) [i.e., (a) or (b)], the functionals at time t are derived for Rij, Ri or R in 3D composition regions as follows, $$I_{ij}(\bullet) = \int\int\int \left[\frac{1}{2}\frac{\partial T_i}{\partial t}(\rho_i c_i)^2 + \left[D_{ix}\left\{\frac{\partial}{\partial x}k_i\right\} + D_{iy}\left\{\frac{\partial}{\partial y}k_i\right\} + D_{iz}\left\{\frac{\partial}{\partial z}k_i\right\} + \left(\frac{\partial}{\partial x}D_{ix} + \frac{\partial}{\partial y}D_{iy} + \frac{\partial}{\partial z}D_{iz}\right)k_i\right](\rho_i c_i)dV, \quad (51)$$

for 2D composition regions as follows, $$I_{ij}(\bullet) = \iint \frac{1}{2}\frac{\partial T_i}{\partial t}(\rho_i c_i)^2 + \left[D_{ix}\left\{\frac{\partial}{\partial x}k_i\right\} + D_{iy}\left\{\frac{\partial}{\partial y}k_i\right\} + \left(\frac{\partial}{\partial x}D_{ix} + \frac{\partial}{\partial y}D_{iy}\right)k_i\right](\rho_i c_i)dA, \quad (52)$$

for 1D composition regions as follows, $$I_{ij}(\bullet) = \int \frac{1}{2}\frac{\partial T_i}{\partial t}(\rho_i c_i)^2 + \left[D_{ix}\left\{\frac{\partial}{\partial x}k_i\right\} + \left(\frac{\partial}{\partial x}D_{ix}\right)k_i\right](\rho_i c_i)dx. \quad (53)$$

Otherwise, according to the first principle, when the distributions Q, i.e., the density distributions Sij [$\rho_i(x,y,z,t)$ in 3D composition regions, $\rho_i(x,y,t)$ in 2D composition regions and $\rho_i(x,t)$ in 1D composition regions], $S_i$ [$\rho_i(x,y,z)$ in 3D composition regions, $\rho_i(x,y)$ in 2D composition regions and $\rho_i(x)$ in 1D composition regions] and S [$\rho(x,y,z)$ in 3D composition regions, $\rho(x,y)$ in 2D composition regions and $\rho(x)$ in 1D composition regions] expressed in the first order partial differential equations (41) in the 3D, 2D or 1D composition regions, are finite-element-approximated or discrete-approximated (based on the calculus of variations) [i.e., (a) or (b)], the functionals at time t are derived for Sij, Si or S in 3D composition regions as follows, $$I_{ij}(\bullet) = \iiint \frac{1}{2}c_i\frac{\partial T_i}{\partial t}(\rho_i)^2 + \left[D_{ix}\left\{\frac{\partial}{\partial x}k_i\right\} + D_{iy}\left\{\frac{\partial}{\partial y}k_i\right\} + D_{iz}\left\{\frac{\partial}{\partial z}k_i\right\} + \left(\frac{\partial}{\partial x}D_{ix} + \frac{\partial}{\partial y}D_{iy} + \frac{\partial}{\partial z}D_{iz}\right)k_i\right](\rho_i)dV,$$

for 2D composition regions as follows, $$I_{ij}(\bullet) = \iint \frac{1}{2}c_i\frac{\partial T_i}{\partial t}(\rho_i)^2 + \left[D_{ix}\left\{\frac{\partial}{\partial x}k_i\right\} + D_{iy}\left\{\frac{\partial}{\partial y}k_i\right\} + \left(\frac{\partial}{\partial x}D_{ix} + \frac{\partial}{\partial y}D_{iy}\right)k_i\right](\rho_i)dA, \quad (55)$$

for 1D composition regions as follows, $$I_{ij}(\bullet) = \int \frac{1}{2}c_i\frac{\partial T_i}{\partial t}(\rho_i)^2 + \left[D_{ix}\left\{\frac{\partial}{\partial x}k_i\right\} + \left(\frac{\partial}{\partial x}D_{ix}\right)k_i\right](\rho_i)dx. \quad (56)$$

If ci is homogeneous or assumed to be homogeneous, Iij(.) can be divided by ci.

Otherwise, according to the first principle, when the distributions Q, i.e., the specific heat distributions Sij [$c_i(x,y,z,t)$ in 3D composition regions, $c_i(x,y,t)$ in 2D composition regions and $c_i(x,t)$ in 1D composition regions], $S_i$ [$c_i(x,y,z)$ in 3D composition regions, $c_i(x,y)$ in 2D composition regions and $c_i(x)$ in 1D composition regions] and S [$c(x,y,z)$ in 3D composition regions, $c(x,y)$ in 2D composition regions and $c(x)$ in 1D composition regions] expressed in the first order partial differential equations (41) in the 3D, 2D or 1D composition regions, are finite-element-approximated or discrete-approximated (based on the calculus of variations) [i.e., (a) or (b)], the functionals at time t are derived for Sij, Si or S in 3D composition regions as follows, $$I_{ij}(\bullet) = \iiint \frac{1}{2}\rho_i\frac{\partial T_i}{\partial t}(c_i)^2 + \left[D_{ix}\left\{\frac{\partial}{\partial x}k_i\right\} + D_{iy}\left\{\frac{\partial}{\partial y}k_i\right\} + D_{iz}\left\{\frac{\partial}{\partial z}k_i\right\} + \left(\frac{\partial}{\partial x}D_{ix} + \frac{\partial}{\partial y}D_{iy} + \frac{\partial}{\partial z}D_{iz}\right)k_i\right](c_i)dV, \quad (57)$$

for 2D composition regions as follows, $$I_{ij}(\cdot) = \iint \frac{1}{2}\rho_i\frac{\partial T_i}{\partial t}(c_i)^2 + \left[D_{ix}\left\{\frac{\partial}{\partial x}k_i\right\} + D_{iy}\left\{\frac{\partial}{\partial y}k_i\right\} + \left(\frac{\partial}{\partial x}D_{ix} + \frac{\partial}{\partial y}D_{iy}\right)k_i\right](c_i)dA, \quad (58)$$

for 1D composition regions as follows, $$I_{ij}(\cdot) = \int \frac{1}{2}\rho_i\frac{\partial T_i}{\partial t}(c_i)^2 + \left[D_{ix}\left\{\frac{\partial}{\partial x}k_i\right\} + \left(\frac{\partial}{\partial x}D_{ix}\right)k_i\right](c_i)dx. \quad (59)$$

If $\rho i$ is homogeneous or assumed to be homogeneous, Iij(.) can be divided by $\rho i$.

Otherwise, according to the first principle, when the distributions Q, i.e., the thermal diffusivity distributions $H_{0ij}$ [$h_{0i}$(x,y,z,t) in 3D composition regions, $h_{0i}$(x,y,t) in 2D composition regions and $h_{0i}$(x,t) in 1D composition regions], $H_{0i}$ [$h_{0i}$(x,y,z) in 3D composition regions, $h_{0i}$(x,y) in 2D composition regions and $h_{0i}$(x) in 1D composition regions] or $H_0$ [$h_0$(x,y,z) in 3D composition regions, $h_0$(x,y) in 2D composition regions and $h_0$(x) in 1D composition regions] expressed in the first order partial differential equations (43) in the 3D, 2D or 1D composition regions, are finite-element-approximated or discrete-approximated (based on the calculus of variations) [i.e., (a) or (b)], the functionals at time t are derived for $H_{0ij}$, $H_{0i}$ or $H_0$ in 3D composition regions as follows, $$I_{ij}(\cdot) = \iiint \frac{\partial T_i}{\partial t}h_{0i} + \left[\frac{1}{4}D_{ix}\left\{\frac{\partial}{\partial x}(h_{0i})^2\right\} + \frac{1}{4}D_{iy}\left\{\frac{\partial}{\partial y}(h_{0i})^2\right\} + \frac{1}{4}D_{iz}\left\{\frac{\partial}{\partial z}(h_{0i})^2\right\} + \frac{1}{2}\left(\frac{\partial}{\partial x}D_{ix} + \frac{\partial}{\partial y}D_{iy} + \frac{\partial}{\partial z}D_{iz}\right)(h_{0i})^2\right]dV, \quad (60)$$

for 2D composition regions as follows, $$I_{ij}(\cdot) = \iint \frac{\partial T_i}{\partial t}h_{0i} + \left[\frac{1}{4}D_{ix}\left\{\frac{\partial}{\partial x}(h_{0i})^2\right\} + \frac{1}{4}D_{iy}\left\{\frac{\partial}{\partial y}(h_{0i})^2\right\} + \frac{1}{2}\left(\frac{\partial}{\partial x}D_{ix} + \frac{\partial}{\partial y}D_{iy}\right)(h_{0i})^2\right]dA, \quad (61)$$

for 1D composition regions as follows, $$I_{ij}(\cdot) = \int \frac{\partial T_i}{\partial t} h_{0i} + \left[\frac{1}{4} D_{ix}\left\{\frac{\partial}{\partial x}(h_{0i})^2\right\} + \frac{1}{2}\left(\frac{\partial}{\partial x} D_{ix}\right)(h_{0i})^2\right] dx. \quad (62)$$

Otherwise, according to the first principle, when the distributions Q, i.e., the first order partial derivative distributions of the thermal diffusivity in the 1D composition regions, i.e., $dh_{0i}(x,t)/dx$, $dh_{0i}(x)/dx$ or $dh_0(x,y)/dx$, expressed in the first order partial differential equations (43) in the 1D composition regions, are finite-element-approximated or discrete-approximated (based on the calculus of variations) [i.e., (a) or (b)], the functional at time t is derived as $$I_{ij}(\cdot) = \int \frac{\partial T_i}{\partial t}\frac{\partial h_{0i}}{\partial x} + \left[\frac{1}{2} D_{ix}\left\{\frac{\partial}{\partial x} h_{0i}\right\}^2 + \frac{1}{4}\left(\frac{\partial}{\partial x} D_{ix}\frac{\partial}{\partial x}(h_{0i})^2\right)\right] dx. \quad (63)$$

Otherwise, according to the first principle, when the distributions Q, i.e., the ratio distributions of the thermal conductivity and density $H_{1ij}$ [$h_{1i}(x,y,z,t)$ in 3D composition regions, $h_{1i}(x,y,t)$ in 2D composition regions and $h_{1i}(x,t)$ in 1D composition regions], $H_{1i}$ [$h_{1i}(x,y,z)$ in 3D composition regions, $h_{1i}(x,y)$ in 2D composition regions and $h_{1i}(x)$ in 1D composition regions] or $H_1$ [$h_1(x,y,z)$ in 3D composition regions, $h_1(x,y)$ in 2D composition regions and $h_1(x)$ in 1D composition regions] expressed in the first order partial differential equations (45) in the 3D, 2D or 1D composition regions, are finite-element-approximated or discrete-approximated (based on the calculus of variations) [i.e., (a) or (b)], the functionals at time t are derived for $H_{1ij}$, $H_{1i}$ or $H_1$ in 3D composition regions as follows, $$I_{ij}(\cdot) = \int\int\int c_i \frac{\partial T_i}{\partial t} h_{1i} + \left[\frac{1}{4} D_{ix}\left\{\frac{\partial}{\partial x}(h_{1i})^2\right\} + \frac{1}{4} D_{iy}\left\{\frac{\partial}{\partial y}(h_{1i})^2\right\} + \right. \quad (64)$$
$$\left. \frac{1}{4} D_{iz}\left\{\frac{\partial}{\partial z}(h_{1i})^2\right\} + \frac{1}{2}\left(\frac{\partial}{\partial x} D_{ix} + \frac{\partial}{\partial y} D_{iy} + \frac{\partial}{\partial z} D_{iz}\right)(h_{1i})^2\right] dV,$$

for 2D composition regions as follows, $$I_{ij}(\cdot) = \int\int c_i \frac{\partial T_i}{\partial t} h_{1i} + \left[\frac{1}{4} D_{ix}\left\{\frac{\partial}{\partial x}(h_{1i})^2\right\} + \right. \quad (65)$$
$$\left. \frac{1}{4} D_{iy}\left\{\frac{\partial}{\partial y}(h_{1i})^2\right\} + \frac{1}{2}\left(\frac{\partial}{\partial x} D_{ix} + \frac{\partial}{\partial y} D_{iy}\right)(h_{1i})^2\right] dA,$$

for 1D composition regions as follows, $$I_{ij}(\cdot) = \int c_i \frac{\partial T_i}{\partial t} h_{1i} + \left[\frac{1}{4} D_{ix}\left\{\frac{\partial}{\partial x}(h_{1i})^2\right\} + \frac{1}{2}\left(\frac{\partial}{\partial x} D_{ix}\right)(h_{1i})^2\right] dx. \quad (66)$$

Otherwise, according to the first principle, when the distributions Q, i.e., the first order partial derivative distributions of the ratio of the thermal conductivity and density in the 1D composition regions, i.e., $dh_{1i}(x,t)/dx$, $dh_{1i}(x)/dx$ or $dh_1(x,y)/dx$, expressed in the first order partial differential equations (45) in the 1D composition regions, are finite-element-approximated or discrete-approximated (based on the calculus of variations) [i.e., (a) or (b)], the functional at time t is derived as $$I_{ij}(\cdot) = \int c_i \frac{\partial T_i}{\partial t}\frac{\partial h_{1i}}{\partial x} + \left[\frac{1}{2} D_{ix}\left\{\frac{\partial}{\partial x} h_{1i}\right\}^2 + \frac{1}{4}\left(\frac{\partial}{\partial x} D_{ix}\frac{\partial}{\partial x}(h_{1i})^2\right)\right] dx. \quad (67)$$

Otherwise, according to the first principle, when the distributions Q, i.e., the ratio distributions of the thermal conductivity and specific heat $H_{2i}$ [$h_{2i}(x,y,z,t)$ in 3D composition regions, $h_{2i}(x,y,t)$ in 2D composition regions and $h_{2i}(x,t)$ in 1D composition regions], $H_{2i}$ [$h_{2i}(x,y,z)$ in 3D composition regions, $h_{2i}(x,y)$ in 2D composition regions and $h_{2i}(x)$ in 1D composition regions] or $H_2$ [$h_2(x,y,z)$ in 3D composition regions, $h_2(x,y)$ in 2D composition regions and $h_2(x)$ in 1D composition regions] expressed in the first order partial differential equations (47) in the 3D, 2D or 1D composition regions, are finite-element-approximated or discrete-approximated (based on the calculus of variations) [i.e., (a) or (b)], the functionals at time t are derived for $H_{2ij}$, $H_{2i}$ or $H_2$ in 3D composition regions as follows, $$I_{ij}(\bullet) = \int\int\int \rho_i \frac{\partial T_i}{\partial t} h_{2i} + \left[\frac{1}{4} D_{ix}\left\{\frac{\partial}{\partial x}(h_{2i})^2\right\} + \frac{1}{4} D_{iy}\left\{\frac{\partial}{\partial y}(h_{2i})^2\right\} + \right. \quad (68)$$
$$\left. \frac{1}{4} D_{iz}\left\{\frac{\partial}{\partial z}(h_{2i})^2\right\} + \frac{1}{2}\left(\frac{\partial}{\partial x} D_{ix} + \frac{\partial}{\partial y} D_{iy} + \frac{\partial}{\partial z} D_{iz}\right)(h_{2i})^2\right] dV,$$

for 2D composition regions as follows, $$I_{ij}(\bullet) = \int\int \rho_i \frac{\partial T_i}{\partial t} h_{2i} + \left[\frac{1}{4} D_{ix}\left\{\frac{\partial}{\partial x}(h_{2i})^2\right\} + \right. \quad (69)$$
$$\left. \frac{1}{4} D_{iy}\left\{\frac{\partial}{\partial y}(h_{2i})^2\right\} + \frac{1}{2}\left(\frac{\partial}{\partial x} D_{ix} + \frac{\partial}{\partial y} D_{iy}\right)(h_{2i})^2\right] dA,$$

for 1D composition regions as follows, $$I_{ij}(\bullet) = \int \rho_i \frac{\partial T_i}{\partial t} h_{2i} + \left[\frac{1}{4} D_{ix}\left\{\frac{\partial}{\partial x}(h_{2i})^2\right\} + \frac{1}{2}\left(\frac{\partial}{\partial x} D_{ix}\right)(h_{2i})^2\right] dx. \quad (70)$$

Otherwise, according to the first principle, when the distributions Q, i.e., the first order partial derivative distributions of the ratio of the thermal conductivity and specific heat in the 1D composition regions, i.e., $dh_{2i}(x,t)/dx$, $dh_{2i}(x)/dx$ or $dh_2(x,y)/dx$, expressed in the first order partial differential equations (47) in the 1D composition regions, are finite-element-approximated or discrete-approximated (based on the calculus of variations) [i.e., (a) or (b)], the functional at time t is derived as $$I_{ij}(\bullet) = \quad (71)$$
$$\int \rho_i \frac{\partial T_i}{\partial t}\frac{\partial h_{2i}}{\partial x} + \left[\frac{1}{2} D_{ix}\left\{\frac{\partial}{\partial x} h_{2i}\right\}^2 + \frac{1}{4}\left(\frac{\partial}{\partial x} D_{ix}\frac{\partial}{\partial x}(h_{2i})^2\right)\right] dx.$$

Otherwise, according to the first principle, when the distributions Q, i.e., the temperature distributions sit [$T_i(x,y,z,t)$ in 3D composition regions, $T_i(x,y,t)$ in 2D composition regions and $T_i(x,t)$ in 3D composition regions] expressed in the first order partial differential equations (41) in the 3D, 2D or 1D composition regions, are finite-element-approximated or discrete-approximated (based on the calculus of variations) [i.e., (a) or (b)], the functionals at time t are derived as $I_{ij}(s_{ij})$ [eq. (72)] by adding $$\frac{\rho_i c_i}{2}\frac{\partial}{\partial t}(T_i)^2 \text{ in case } (a) \text{ and } \frac{\rho_i c_i}{4}\frac{\partial}{\partial t}(T_i)^2 \text{ in case } (b)$$

to the integral kernels of the functionals $I_{ij}(S_{ij})$ at time t [(i.e., integral kernels in the second eq. in (6) in 3D composition regions, second eq. in (8) in 2D composition regions and second eq. in (10) in 1D composition regions].

Otherwise, according to the first principle, when the distributions Q, i.e., the temperature distributions $s_{ij}$ [$T_i(x,y,z,t)$ in 3D composition regions, $T_i(x,y,t)$ in 2D composition regions and $T_i(x,t)$ in 3D composition regions] expressed in the first order partial differential equations (43) in the 3D, 2D or 1D composition regions, are finite-element-approximated or discrete-approximated (based on the calculus of variations) [i.e., (a) or (b)], the functionals at time t are derived as $I_{ij}(s_{ij})$ [eq. (73)] by adding $$\frac{1}{2}\frac{\partial}{\partial t}(T_i)^2 \text{ in case } (a) \text{ and } \frac{1}{4}\frac{\partial}{\partial t}(T_i)^2 \text{ in case } (b)$$

to the integral kernels of the functionals for $S_{ij}$ in 3D composition regions, $$I_{ij}(s_{ij}) = \frac{1}{2}\int\int\int\left\{h_{0i}\left(\frac{\partial}{\partial x}T_i\right)^2 + h_{0i}\left(\frac{\partial}{\partial y}T_i\right)^2 + h_{0i}\left(\frac{\partial}{\partial z}T_i\right)^2\right\}dV,$$

for 2D composition regions, $$I_{ij}(s_{ij}) = \frac{1}{2}\int\int\left\{h_{0i}\left(\frac{\partial}{\partial x}T_i\right)^2 + h_{0i}\left(\frac{\partial}{\partial y}T_i\right)^2\right\}dA,$$

for 1D composition regions, $$I_{ij}(s_{ij}) = \frac{1}{2}\int\left\{h_{0i}\left(\frac{\partial}{\partial x}T_i\right)^2\right\}dx.$$

Otherwise, according to the first principle, when the distributions Q, i.e., the temperature distributions sij [$T_i(x,y,z,t)$ in 3D composition regions, $T_i(x,y,t)$ in 2D composition regions and $T_i(x,t)$ in 3D composition regions] expressed in the first order partial differential equations (45) in the 3D, 2D or 1D composition regions, are finite-element-approximated or discrete-approximated (based on the calculus of variations) [i.e., (a) or (b)], the functionals at time t are derived as $I_{ij}(s_{ij})$ [eq. (74)] by adding $$\frac{c_i}{2}\frac{\partial}{\partial t}(T_i)^2 \text{ in case } (a) \text{ and } \frac{c_i}{4}\frac{\partial}{\partial t}(T_i)^2 \text{ in case } (b)$$

to the integral kernels of the functionals for $S_{ij}$ in 3D composition regions, $$I_{ij}(s_{ij}) = \frac{1}{2}\int\int\int\left\{h_{1i}\left(\frac{\partial}{\partial x}T_i\right)^2 + h_{1i}\left(\frac{\partial}{\partial y}T_i\right)^2 + h_{1i}\left(\frac{\partial}{\partial z}T_i\right)^2\right\}dV,$$

for 2D composition regions, $$I_{ij}(s_{ij}) = \frac{1}{2}\int\int\left\{h_{1i}\left(\frac{\partial}{\partial x}T_i\right)^2 + h_{1i}\left(\frac{\partial}{\partial y}T_i\right)^2\right\}dA,$$

for 1D composition regions, $$I_{ij}(s_{ij}) = \frac{1}{2}\int\left\{h_{1i}\left(\frac{\partial}{\partial x}T_i\right)^2\right\}dx.$$

Otherwise, according to the first principle, when the distributions Q, i.e., the temperature distributions sij [$T_i(x,y,z,t)$ in 3D composition regions, $T_i(x,y,t)$ in 2D composition regions and $T_i(x,t)$ in 3D composition regions] expressed in the first order partial differential equations (47) in the 3D, 2D or 1D composition regions, are finite-element-approximated or discrete-approximated (based on the calculus of variations) [i.e., (a) or (b)], the functionals at time t are derived as $I_{ij}(s_{ij})$ [eq. (75)] by adding $$\frac{\rho_i}{2}\frac{\partial}{\partial t}(T_i)^2 \text{ in case}(a)$$

and $$\frac{\rho_i}{4}\frac{\partial}{\partial t}(T_i)^2 \text{ in case}(b)$$

to the integral kernels of the functionals for $S_{ij}$ in 3D composition regions, $$I_{ij}(s_{ij}) = \frac{1}{2}\int\int\int\left\{h_{2i}\left(\frac{\partial}{\partial x}T_i\right)^2 + h_{2i}\left(\frac{\partial}{\partial y}T_i\right)^2 + h_{2i}\left(\frac{\partial}{\partial z}T_i\right)^2\right\}dV,$$

for 2D composition regions, $$I_{ij}(s_{ij}) = \frac{1}{2}\int\int\left\{h_{2i}\left(\frac{\partial}{\partial x}T_i\right)^2 + h_{2i}\left(\frac{\partial}{\partial y}T_i\right)^2\right\}dA,$$

for 1D composition regions, $$I_{ij}(s_{ij}) = \frac{1}{2}\int\left\{h_{2i}\left(\frac{\partial}{\partial x}T_i\right)^2\right\}dx.$$

When the ROI is 3D, at least one of the functionals $I_{ij}(Q)$ [eq. (49) to (75)] with respect to the unknown distribution Q in 3D, 2D or 1D composition regions derived from eqs. (41), (43), (45) or (47) are finite-element-approximated or discrete-approximated using the prespecified basis functions. Here, Q are $L_{ij}$, $L_i$, L, the first order partial derivative distribution of the thermal conductivity, $R_{ij}$, $R_i$, R, $S_{ij}$, $S_i$, S, $H_{0ij}$, $H_0i$, $H_0$, the first order partial derivative distribution of the diffusivity, $H_{1ij}$, $H_{1i}$, $H_1$, the first order partial derivative distribution of the ratio of the thermal conductivity and density, $H_{2ij}$, $H_{2i}$, $H_2$, the first order partial derivative distribution of the ratio of the thermal conductivity and specific heat, or $s_{ij}$. As the result, the following functionals $I_{ij}(Q'')$ are derived for the unknown nodal distributions Q''. If only one functional $I_{ij}(Q)$ is used, the composition region is the ROI itself.

(1) The functionals $I_{ij}(L''_{ij})$ with respect to the vector $L''_{ij}$ composed of the thermal conductivity nodal distributions $k_i(I,J,K,j)$, $k_i(I,J,j)$ or $k_i(I,j)$ in 3D, 2D or 1D composition regions, the functionals $I_{ij}(L''_i)$ with respect to the vector $L''_i$ composed of the thermal conductivity nodal distributions $k_i(I,J,K)$, $k_i(I,J)$ or $k_i(I)$ in 3D, 2D or 1D composition regions, the functionals $I_{ij}(L'')$ with respect to the vector $L''$ composed of the thermal conductivity nodal distributions $k(I,J,K)$, $k(I,J)$ or $k(I)$ in 3D, 2D or 1D composition regions.

(2) The functionals $I_{ij}(R''_{ij})$ with respect to the vector $R''_{ij}$ composed of the product nodal distributions of the density and specific heat $\rho c_i(I,J,K,j)$, $\rho c_i(I,J,j)$ or $\rho c_i(I,j)$ in 3D, 2D or 1D composition regions, the functionals $I_{ij}(R''_i)$ with respect to the vector $R''_i$ composed of the product nodal distributions of the density and specific heat $\rho c_i(I,J,K)$, $\rho c_i(I,J)$ or $\rho c_i(I)$ in 3D, 2D or 1D composition regions, the functionals $I_{ij}(R'')$ with respect to the vector $R''$ composed of the product nodal distributions of the density and specific heat $\rho c(I,J,K)$, $\rho c(I,J)$ or $\rho c(I)$ in 3D, 2D or 1D composition regions.

(3) The functionals $I_{ij}(S''_{ij})$ with respect to the vector $S''_{ij}$ composed of the density nodal distributions $\rho_i(I,J,K,j)$, $\rho_i(I,J,j)$ or $\rho_i(I,j)$ in 3D, 2D or 1D composition regions, the functionals $I_{ij}(S''_i)$ with respect to the vector $S''_i$ composed of the density nodal distributions $\rho_i(I,J,K)$, $\rho_i(I,J)$ or $\rho_i(I)$ in 3D, 2D or 1D composition regions, the functionals $I_{ij}(S'')$ with respect to the vector $S''$ composed of the density nodal distributions $\rho(I,J,K)$, $\rho(I,J)$ or $\rho(I)$ in 3D, 2D or 1D composition regions.

(4) The functionals $I_{ij}(S''_{ij})$ with respect to the vector $S''_{ij}$ composed of the specific heat nodal distributions $c_i(I,J,K,j)$, $c_i(I,J,j)$ or $c_i(I,j)$ in 3D, 2D or 1D composition regions, the functionals $I_{ij}(S''_i)$ with respect to the vector $S''_i$ composed of the specific heat nodal distributions $c_i(I,J,K)$, $c_i(I,J)$ or $c_i(I)$ in 3D, 2D or 1D composition regions, the functionals $I_{ij}(S'')$ with respect to the vector $S''$ composed of the specific heat nodal distributions $c(I,J,K)$, $c(I,J)$ or $c(I)$ in 3D, 2D or 1D composition regions.

(5) The functionals $I_{ij}(H_0''ij)$ with respect to the vector $H_0''ij$ composed of the thermal diffusivity nodal distributions $h_{0i}(I,J,K,j)$, $h_{0i}(I,J,j)$ or $h_{0i}(I,j)$ in 3D, 2D or 1D composition regions, the functionals $I_{ij}(H_0''i)$ with respect to the vector $H_0''i$ composed of the thermal diffusivity nodal distributions $h_{0i}(I,J,K)$, $h_{0i}(I,J)$ or $h_{0i}(I)$ in 3D, 2D or 1D composition regions, the functionals $I_{ij}(H_0'')$ with respect to the vector $H_0''$ composed of the thermal diffusivity nodal distributions $h_0(I,J,K)$, $h_0(I,J)$ or $h_0(I)$ in 3D, 2D or 1D composition regions.

(6) The functionals $I_{ij}(H_1''ij)$ with respect to the vector $H_1''ij$ composed of the ratio nodal distributions of the thermal conductivity and density $h_{1i}(I,J,K,j)$, $h_{1i}(I,J,j)$ or $h_{1i}(I,j)$ in 3D, 2D or 1D composition regions, the functionals $I_{ij}(H_1''i)$ with respect to the vector $H_1''i$ composed of the ratio nodal distributions of the thermal conductivity and density $h_{1i}(I,J,K)$, $h_{1i}(I,J)$ or $h_{1i}(I)$ in 3D, 2D or 1D composition regions, the functionals $I_{ij}(H_1'')$ with respect to the vector $H_1''$ composed of the ratio nodal distributions of the thermal conductivity and density $h_1(I,J,K)$, $h_1(I,J)$ or $h_1(I)$ in 3D, 2D or 1D composition regions.

(7) The functionals $I_{ij}(H_2''ij)$ with respect to the vector $H_2''ij$ composed of the ratio nodal distributions of the thermal conductivity and specific heat $h_{2i}(I,J,K,j)$, $h_{2i}(I,J,j)$ or $h_{2i}(I,j)$ in 3D, 2D or 1D composition regions, the functionals $I_{ij}(H_2''i)$ with respect to the vector $H_2''i$ composed of the ratio nodal distributions of the thermal conductivity and specific heat $h_{2i}(I,J,K)$, $h_{2i}(I,J)$ or $h_{2i}(I)$ in 3D, 2D or 1D composition regions, the functionals $I_{ij}(H_2'')$ with respect to the vector $H_2''$ composed of the ratio nodal distributions of the thermal conductivity and specific heat $h_2(I,J,K)$, $h_2(I,J)$ or $h_2(I)$ in 3D, 2D or 1D composition regions.

(8) The functionals $I_{ij}(s''ij)$ with respect to the vector $s''ij$ composed of the temperature nodal distributions $T_i(I,J,K,j)$, $T_i(I,J,j)$ or $T_i(I,j)$ in 3D, 2D or 1D composition regions.

Respective these functionals are minimized with respect to the nodal distribution Q'' [i.e., $L''_{ij}$, $L''_i$, $L''$, $R''_{ij}$, $R''_i$, $R''$, $S''_{ij}$, $S''_i$, $S''$, $H_0''_{ij}$, $H_0''_i$, $H_0''$, $H_1''_{ij}$, $J_1''_i$, $H_1''$, $H_2''_{ij}$, $H_2''_i$, $H_2''$ or $s''_{ij}$], after which all the nodal data in the ROI [the low-pass-filtered temperature distributions data $T_i(I,J,K,j)$, temporal first order partial derivative distributions data of the temperature, temperature gradient vector distributions data $D_i(I,J,K,j)$, divergence distributions data of the temperature gradient vector, and occasionally reference thermal conductivities (distributions) data $k'i(I,J,K,j)$, $k'_i(I,J,K)$, $k'(I,J,K)$, reference thermal diffusivities (distributions) data $h_0'_i(I,J,K,j)$, $h_0'_i(I,J,K)$, $h_0'(I,J,K)$, reference ratios (distributions) data of the thermal conductivity and density $h_1'_i(I,J,K,j)$, $h_1'_i(I,J,K)$, $h_1'(I,J,K)$, reference ratios (distributions) data of the thermal conductivity and specific heat $h_2'_i(I,J,K,j)$, $h_2'_i(I,J,K)$, $h_2'(I,J,K)$, reference products (distributions) data of the density and specific heat $\rho c_i(I,J,K,j)$, $\rho c_i(I,J,K)$, $\rho c(I,J,K)$, reference densities (distributions) data $\rho_i(I,J,K,j)$, $\rho_i(I,J,K)$, $\rho(I,J,K)$, reference specific heats (distributions) data $c_i(I,J,K,j)$, $c_i(I,J,K)$, $c(I,J,K)$] are substituted into the derived algebra equations.

Thus, when the ROI is 3D, by dealing with all the derived algebra equations for the respective unknown nodal distributions in 3D, 2D or 1D composition regions in the 3D ROI, the following algebra equations are derived for the unknown nodal vector U' over the ROI composed of the respective unknown nodal distributions in the composition regions, i.e., $$E_{ij}U' = e_{ij} \quad (76)$$

Here, the composition regions can have the same regions each other.

The unknown nodal vector U' in eqs. (76) derived from eqs. (41) [i.e., eq. (49) to (59) and (72)] includes as the vector components, i.e., the unknown thermal conductivity nodal distributions $L'_{ij}$ $[k_i(I,J,K,j)]$, $L'_i$ $[k_i(I,J,K)]$, $L'$ $[k(I,J,K)]$ respectively when the ROI having the 3D composition regions whose thermal conductivity distributions $k_i(x,y,z,t)$, $k_i(x,y,z)$, $k(x,y,z)$ are unknown, the unknown thermal conductivity nodal distributions $L'_{ij}$ $[k_i(I,J,j)]$, $L'_i$ $[k_i(I,J)]$, $L'$ $[k(I,J)]$ respectively when the ROI having the 2D composition regions whose thermal conductivity distributions $k_i(x,y,t)$, $k_i(x,y)$, $k(x,y)$ are unknown, the unknown thermal conductivity nodal distributions $L'_{ij}$ $[k_i(I,j)]$, $L'_i$ $[k_i(I)]$, $L'$ $[k(I)]$ respectively when the ROI having the 1D composition regions whose thermal conductivity distributions $k_i(x,t)$, $k_i(x)$, $k(x)$ are unknown, the unknown product nodal distributions of the density and specific heat $R'_{ij}$ $[\rho c_i(I,J,K,j)]$, $R'_i$ $[\rho c_i(I,J,K)]$, $R'$ $[\rho c(I,J,K)]$ respectively when the ROI having the 3D composition regions whose density distributions $\rho_i(x,y,z,t)$, $\rho_i(x,y,z)$, $\rho(x,y,z)$ and specific heat distributions $c_i(x,y,z,t)$, $c_i(x,y,z)$, $c(x,y,z)$ are unknown, the unknown product nodal distributions of the density and specific heat $R'_{ij}$ [$\rho c_i(I,J,j)$], $R'_i$ [$\rho c_i(I,J)$], $R'$ [$\rho c(I,J)$] respectively when the ROI having the 2D composition regions whose density distributions $\rho_i(x,y,t)$, $\rho_i(x,y)$, $\rho(x,y)$ and specific heat distributions $c_i(x,y,t)$, $c_i(x,y)$, $c(x,y)$ are unknown, the unknown product nodal distributions of the density and specific heat $R'_{ij}$ [$\rho c_i(I,j)$], $R'_i$ [$\rho c_i(I)$], $R'$[$\rho c(I)$] respectively when the ROI having the 1D composition regions whose density distributions $\rho_i(x,t)$, $\rho_i(x)$, $\rho(x)$ and specific heat distributions $c_i(x,t)$, $c_i(x)$, $c(x)$ are unknown, the unknown density nodal distributions $S'_{ij}$ [$\rho_i(I,J,K,j)$], $S'_i$ [$\rho_i(I,J,K)$], $S'$ [$\rho(I,J,K)$] respectively when the ROI having the 3D composition regions whose density distributions $\rho_i(x,y,z,t)$, $\rho_i(x,y,z)$, $\rho(x,y,z)$ are unknown, the unknown density nodal distributions $S'_{ij}$ [$\rho_i(I,J,j)$], $S'_i$ [$\rho_i(I,J)$], $S'$ [$\rho(I,J)$] respectively when the ROI having the 2D composition regions whose density distributions $\rho_i(x,y,t)$, $\rho_i(x,y)$, $\rho(x,y)$ are unknown, the unknown density nodal distributions $S'_{ij}$ [$\rho_i(I,j)$], $S'_i$ [$\rho_i(I)$], $S'$ [$\rho(I)$] respectively when the ROI having the 1D composition regions whose density distributions $\rho_i(x,t)$, $\rho_i(x)$, $\rho(x)$ are unknown, the unknown specific heat nodal distributions $S'_{ij}$ [$c_i(I,J,K,j)$], $S'_i$ [$c_i(I,J,K)$], $S'$ [$c(I,J,K)$] respectively when the ROI having the 3D composition regions whose specific heat distributions $c_i(x,y,z,t)$, $c_i(x,y,z)$, $c(x,y,z)$ are unknown, the unknown specific heat nodal distributions $S'_{ij}$ [$c_i(I,J,j)$], $S'_i$ [$c_i(I,J)$], $S'$ [$c(I,J)$] respectively when the ROI having the 2D composition regions whose specific heat distributions $c_i(x,y,t)$, $c_i(x,y)$, $c(x,y)$ are unknown, the unknown specific heat nodal distributions $S'_{ij}$ [$c_i(I,j)$], $S'_i$ [$c_i(I)$], $S'$ [$c(I)$] respectively when the ROI having the 1D composition regions whose specific heat distributions $c_i(x,t)$, $c_i(x)$, $c(x)$ are unknown.

Otherwise, the unknown nodal vector U' in eqs. (76) derived from eqs. (43) [i.e., eq. (60) to (63) and (73)] includes as the vector components, i.e., the unknown thermal diffusivity nodal distributions $H'_{0ij}$ [$h_{0i}(I,J,K,j)$], $H'_{0i}$ [$h_{0i}(I,J,K)$], $H'_0$ [$h_0(I,J,K)$] when the ROI having the 3D composition regions, the unknown thermal diffusivity nodal distributions $H'_{0ij}$ [$h_{0i}(I,J,j)$], $H'_{0i}$ [$h_{0i}(I,J)$], $H'_0$ [$h_0(I,J)$] when the ROI having the 2D composition regions, the unknown thermal diffusivity nodal distributions [$h_{0i}(I,j)$], $H'_{0i}$ [$h_{0i}(I)$], $H'_0$ [$h_0(I)$] when the ROI having the 1D composition regions, otherwise, the unknown nodal vector U' in eqs. (76) derived from eqs. (45) [i.e., eq. (64) to (67) and (74)] includes as the vector components, i.e., the unknown ratio nodal distributions of the thermal conductivity and density $H_{1ij}$ [$h_{1i}(I,J,K,j)$], $H_{1ij}$ [$h_{1i}(I,J,K)$], $H_1$ [$h_1(I,J,K)$] when the ROI having the 3D composition regions, the unknown ratio nodal distributions of the thermal conductivity and density $H_{1ij}$ [$h_{1i}(I,J,j)$], $H_{1ij}$ [$h_{1i}(I,J)$], $H_1$ [$h_1(I,J)$] when the ROI having the 2D composition regions, the unknown ratio nodal distributions of the thermal conductivity and density $H_{1ij}$ [$h_{1i}(I,j)$], $H_{1ij}$ [$h_{1i}(I)$], $H_1$ [$h_1(I)$] when the ROI having the 1D composition regions, otherwise, the unknown nodal vector U' in eqs. (76) derived from eqs. (47) [i.e., eq. (68) to (71) and (75)] includes as the vector components, i.e., the unknown ratio nodal distributions of the thermal conductivity and specific heat $H_{2ij}$ [$h_{2i}(I,J,K,j)$], $H_{2i}$ [$h_{2i}(I,J,K)$], $H_2$ [$h_2(I,J,K)$] when the ROI having the 3D composition regions, the unknown ratio nodal distributions of the thermal conductivity and specific heat $H_{2ij}$ [$h_{2i}(I,J,j)$], $H_{2i}$ [$h_{2i}(I,J)$], $H_2$ [$h_2(I,J)$] when the ROI having the 2D composition regions, the unknown ratio nodal distributions of the thermal conductivity and specific heat $H_{2ij}$ [$h_{2i}(I,j)$], $H_{2i}$ [$h_{2i}(I)$], $H_2$ [$h_2(I)$] when the ROI having the 1D composition regions.

When the ROI is 2D, at least one of the functionals $I_{ij}(Q'')$ [eq. (49), (50), (52), (53), (55), (56), (58), (59), (61) to (63), (65) to (67), (69) to (71), (72) to (75)] is minimized with respect to the unknown nodal distributions Q'' in 2D or 1D composition regions [i.e., $L''_{ij}$, $L''_i$, $L''$, $R''_{ij}$, $R''_i$, $R''$, $S''_{ij}$, $S''_i$, $S''$, $H_0''_{ij}$, $H_0''_i$, $H_0''$, $H_1''_{ij}$, $H_1''_i$, $H_1''$, $H_2''_{ij}$, $H_2''_i$, $H_2''$ or $s''_{ij}$]; or when the ROI is 1D, at least one of the functionals $I_{ij}(Q'')$ [eq. (49), (50), (53), (56), (59), (62), (63), (66), (67), (70), (71), (72) to (75)] is minimized with respect to the unknown nodal distributions Q'' in 1D composition regions, by dealing with all the derived algebra equations for the respective unknown nodal distributions, the algebra equations (76) are similarly derived for the unknown nodal vector U' over the ROI composed of the respective unknown nodal distributions in the composition regions.

According to the second principle, in each composition region in the ROI, at least one of the spatial differential equations (41), (43), (45) and (47) expressing each unknown distributions is finite-difference-approximated (discrete-approximated) [i.e., (c)], and by dealing with all the derived algebra equations, the simultaneous equations (76) are derived for the unknown nodal vector U' over the ROI (Occasionally the ROI has composition regions having the same regions each other. If there exists only one composition region, the composition region is the ROI itself).

That is, according to the second principle, after the distributions Q, i.e., the thermal conductivity distributions Lij, Li or L, the first order partial derivatives of the thermal conductivity distributions, product distributions of the density and specific heat Rij, Ri or R, density distributions Sij, Si or S, specific heat distributions Sij, Si or S, temperature gradient vector distributions sij [Di(x,y,z,t) in 3D composition regions, Di(x,y,t) in 2D composition regions, Di(x,t) in 1D composition regions], temporal first order partial derivative distributions of the temperature sij [$dT_i(x,y,z,t)/dt$ in 3D composition regions, $dT_i(x,y,t)/dt$ in 2D composition regions, $dT_i(x,t)/dt$ in 1D composition regions], divergence distributions of the temperature gradient vector sij or temperature distributions sij [$T_i(x,y,z,t)$ in 3D composition regions, $T_i(x,y,t)$ in 2D composition regions, $T_i(x,t)$ in 1D composition regions] expressed in the first order partial differential equations (41) in the 3D, 2D or 1D composition regions, are finite-difference-approximated (discrete-approximated), the nodal data [the low-pass-filtered first order partial derivative distributions data of the temperature $T_i(I,J,K,j)$, temperature gradient vector distributions data D (I,J,K,j), divergence distributions data of the temperature gradient vector, and occasionally the reference thermal conductivities (distributions) data $k'_i(I,J,K,j)$, $k'_i(I,J,K)$, $k'(I,J,K)$, reference thermal diffusivities (distributions) data $h_0'_i(I,J,K,j)$, $h_0'_i(I,J,K)$, $h_0'(I,J,K)$, reference ratios (distributions) data of the thermal conductivity and specific heat $h_1'_i(I,J,K,j)$, $h_1'_i(I,J,K)$, $h_1'(I,J,K)$, reference ratios (distributions) data of the thermal conductivity and specific heat $h_2'_i(I,J,K,j)$, $h_2'_i(I,J,K)$, $h_2'(I,J,K)$, products (distributions) data of the density and specific heat $\rho c_i(I,J,K,j)$, $\rho c_i(I,J,K)$, $\rho c(I,J,K)$, densities (distributions) data $\rho_i(I,J,K,j)$, $\rho_i(I,J,K)$, $\rho(I,J,K)$ or specific heats (distributions) data $c_i(I,J,K,j)$, $c_i(I,J,K)$, $c(I,J,K)$] in the ROI are substituted into the nodal distributions Q'' in the derived algebra equations. Thus, by dealing with all the derived algebra equations, the algebra equations (76) for the unknown nodal distributions U' over the ROI are derived.

Otherwise, according to the second principle, after the distributions Q, i.e., the thermal diffusivity distributions $H_{0ij}$, $H_{0i}$, $H_0$, the first order partial derivative distributions of the thermal diffusivity, temperature gradient vector distributions sij, temporal first order partial derivative distributions of the temperature sij, divergence distributions of the temperature gradient vector sij or temperature distributions sij expressed in the first order partial differential equations (43) in the 3D, 2D or 1D composition regions, are finite-difference-approximated (discrete-approximated), the nodal data [the low-pass-filtered first order partial derivative distributions data of the temperature $T_i(I,J,K,j)$, temperature gradient vector distributions data $D_i(I,J,K,j)$, divergence distributions data of the temperature gradient vector, and occasionally the reference thermal conductivities (distributions) data $k'_i(I,J,K,j)$, $k'_i(I,J,K)$, $k'(I,J,K)$, reference thermal diffusivities (distributions) data $h_0'_i(I,J,K,j)$, $h_0'_i(I,J,K)$, $h_0'(I,J,K)$, reference ratios (distributions) data of the thermal conductivity and specific heat $h_1'_i(I,J,K,j)$, $h_1'_i(I,J,K)$, $h_1'(I,J,K)$, reference ratios (distributions) data of the thermal conductivity and specific heat $h_2'_i(I,J,K,j)$, $h_2'_i(I,J,K)$, $h_2'(I,J,K)$, products (distributions) data of the density and specific heat $\rho c_i(I,J,K,j)$, $\rho c_i(I,J,K)$, $\rho_c(I,J,K)$, densities (distributions) data $\rho_i(I,J,K,j)$, $\rho_i(I,J,K)$, $\rho(I,J,K)$ or specific heats (distributions) data $c_i(I,J,K,j)$, $c_i(I,J,K)$, $c(I,J,K)$] in the ROI are substituted into the nodal distributions Q" in the derived algebra equations. Thus, by dealing with all the derived algebra equations, the algebra equations (76) for the unknown nodal distributions U' over the ROI are derived.

Otherwise, according to the second principle, after the distributions Q, i.e., the ratio distributions of the thermal conductivity and density $H_{1ij}$, $H_{1i}$, $H_1$, the first order partial derivative distributions of the ratio of the thermal conductivity and density, specific heat distributions Sij, Si or S, temperature gradient vector distributions sij, temporal first order partial derivative distributions of the temperature sij, divergence distributions of the temperature gradient vector sij or temperature distributions sij expressed in the first order partial differential equations (45) in the 3D, 2D or 1D composition regions, are finite-difference-approximated (discrete-approximated), the nodal data [the low-pass-filtered first order partial derivative distributions data of the temperature $T_i(I,J,K,j)$, temperature gradient vector distributions data $D_i(I,J,K,j)$, divergence distributions data of the temperature gradient vector, and occasionally the reference thermal conductivities (distributions) data $k'_i(I,J,K,j)$, $k'_i(I,J,K)$, $k'(I,J,K)$, reference thermal diffusivities (distributions) data $h_0'_i(I,J,K,j)$, $h_0'_i(I,J,K)$, $h_0'(I,J,K)$, reference ratios (distributions) data of the thermal conductivity and specific heat $h_1'_i(I,J,K,j)$, $h_1'_i(I,J,K)$, $h_1'(I,J,K)$, reference ratios (distributions) data of the thermal conductivity and specific heat $h_2'_i(I,J,K,j)$, $h_2'_i(I,J,K)$, $h_2'(I,J,K)$, products (distributions) data of the density and specific heat $\rho c_i(I,J,K,j)$, $\rho c_i(I,J,K)$, $\rho_c(I,J,K)$, densities (distributions) data $\rho_i(I,J,K,j)$, $\rho_i(I,J,K)$, $\rho(I,J,K)$ or specific heats (distributions) data $c_i(I,J,K,j)$, $c_i(I,J,K)$, $c(I,J,K)$] in the ROI are substituted into the nodal distributions Q" in the derived algebra equations. Thus, by dealing with all the derived algebra equations, the algebra equations (76) for the unknown nodal distributions U' over the ROI are derived.

Otherwise, according to the second principle, after the distributions Q, i.e., the ratio distributions of the thermal conductivity and specific heat $H_{2ij}$, $H_{2i}$, $H_2$, the first order partial derivative distributions data of the ratio of the thermal conductivity and specific heat, density distributions Sij, Si or S, temperature gradient vector distributions sij, temporal first order partial derivative distributions of the temperature sij, divergence distributions of the temperature gradient vector sij or temperature distributions sij expressed in the first order partial differential equations (47) in the 3D, 2D or 1D composition regions, are finite-difference-approximated (discrete-approximated), the nodal data [the low-pass-filtered first order partial derivative distributions data of the temperature $T_i(I,J,K,j)$, temperature gradient vector distributions data $D_i(I,J,K,j)$, divergence distributions data of the temperature gradient vector, and occasionally the reference thermal conductivities (distributions) data $k'_i(I,J,K,j)$, $k'_i(I,J,K)$, $k'(I,J,K)$, reference thermal diffusivities (distributions) data $h_0'_i(I,J,K,j)$, $h_0'_i(I,J,K)$, $h_0'(I,J,K)$, reference ratios (distributions) data of the thermal conductivity and specific heat $h_1'_i(I,J,K,j)$, $h_1'_i(I,J,K)$, $h_1'(I,J,K)$, reference ratios (distributions) data of the thermal conductivity and specific heat $h_2'_i(I,J,K,j)$, $h_2'_i(I,J,K)$, $h_2'(I,J,K)$, products (distributions) data of the density and specific heat $\rho c_i(I,J,K,j)$, $\rho c_i(I,J,K)$, $\rho c(I,J,K)$, densities (distributions) data $\rho_i(I,J,K,j)$, $\rho_i(I,J,K)$, $\rho(I,J,K)$ or specific heats (distributions) data $c_i(I,J,K,j)$, $c_i(I,J,K)$, $c(I,J,K)$] in the ROI are substituted into the nodal distributions Q" in the derived algebra equations. Thus, by dealing with all the derived algebra equations, the algebra equations (76) for the unknown nodal distributions U' over the ROI are derived.

According to the second principle, in each composition region in the ROI, at least one of the spatial differential equations (41), (43), (45) and (47) expressing each unknown distributions is finite-element-approximated (based on the Galerkin's method) or discrete-approximated [i.e., (a) or (b)], and by dealing with all the derived algebra equations, the simultaneous equations (76) are derived for the unknown nodal vector U' over the ROI (Occasionally the ROI has composition regions having the same regions each other. If there exists only one composition region, the composition region is the ROI itself).

That is, according to the second principle, when the distributions Q, i.e., the thermal conductivity distributions Lij, Li or L, the first order partial derivative distributions of the thermal conductivity, product distributions of the density and specific heat Rij, Ri or R, density distributions Sij, Si or S, specific heat distributions Sij, Si or S, temperature gradient vector distributions sij [Di(x,y,z,t) in 3D composition regions, Di(x,y,t) in 2D composition regions, Di(x,t) in 1D composition regions], temporal first order partial derivative distributions of the temperature sij [$dT_i(x,y,z,t)/dt$ in 3D composition regions, $dT_i(x,y,t)/dt$ in 2D composition regions, $dT_i(x,t)/dt$ in 1D composition regions], divergence distributions of the temperature gradient vector sij or temperature distributions sij [$T_i(x,y,z,t)$ in 3D composition regions, $T_i(x,y,t)$ in 2D composition regions, $T_i(x,t)$ in 1D composition regions] expressed in the first order partial differential equations (41) in the 3D, 2D or 1D composition regions, are finite-element-approximated (based on Galerkin's method) or discrete-approximated [i.e., (a) or (b)], the functionals at time t are derived for Lij, Li or L in 3D composition regions as follows, $$I_{ij}(\bullet) = \int\int\int \left[\rho_i c_i \frac{\partial T_i}{\partial t} + D_{ix}\left\{\frac{\partial}{\partial x}k_i\right\} + D_{iy}\left\{\frac{\partial}{\partial y}k_i\right\} + D_{iz}\left\{\frac{\partial}{\partial z}k_i\right\} + \left(\frac{\partial}{\partial x}D_{ix} + \frac{\partial}{\partial y}D_{iy} + \frac{\partial}{\partial z}D_{iz}\right)k_i\right]v(x, y, z, t)dV, \quad (77)$$

for 2D composition regions, $$I_{ij}(\bullet) = \iint \left[ \rho_i c_i \frac{\partial T_i}{\partial t} + D_{ix}\left\{\frac{\partial}{\partial x}k_i\right\} + D_{iy}\left\{\frac{\partial}{\partial y}k_i\right\} + \left(\frac{\partial}{\partial x}D_{ix} + \frac{\partial}{\partial y}D_{iy}\right)k_i \right] v(x,y,t)dA, \quad (78)$$

for 1D composition regions, $$I_{ij}(\bullet) = \int \left[ \rho_i c_i \frac{\partial T_i}{\partial t} + D_{ix}\left\{\frac{\partial}{\partial x}k_i\right\} + \left(\frac{\partial}{\partial x}D_{ix}\right)k_i \right] v(x,t)dx. \quad (79)$$

Here, v in eqs. (77) to (79) is the weight function being satisfied with $|v(x,y,z,t)|\neq 0$.

Otherwise, according to the second principle, when the distributions Q, i.e., the thermal diffusivity distributions $H_{0ij}$, $H_{0i}$ or $H_0$, the first order partial derivative distributions of the thermal diffusivity, temperature gradient vector distributions sij [Di(x,y,z,t) in 3D composition regions, Di(x,y,t) in 2D composition regions, Di(x,t) in 1D composition regions], temporal first order partial derivative distributions of the temperature sij [$dT_i(x,y,z,t)/dt$ in 3D composition regions, $dT_i(x,y,t)/dt$ in 2D composition regions, $dT_i(x,t)/dt$ in 1D composition regions], divergence distributions of the temperature gradient vector sij or temperature distributions sij [$T_i(x,y,z,t)$ in 3D composition regions, $T_i(x,y,t)$ in 2D composition regions, $T_i(x,t)$ in 1D composition regions] expressed in the first order partial differential equations (43) in the 3D, 2D or 1D composition regions, are finite-element-approximated (based on Galerkin's method) or discrete-approximated [i.e., (a) or (b)], the functionals at time t are derived for $H_{0ij}$, $H_{0i}$ or $H_0$ in 3D composition regions as follows, $$I_{ij}(\bullet) = \iiint \left[ \frac{\partial T_i}{\partial t} + D_{ix}\left\{\frac{\partial}{\partial x}h_{0i}\right\} + D_{iy}\left\{\frac{\partial}{\partial y}h_{0i}\right\} + D_{iz}\left\{\frac{\partial}{\partial z}h_{0i}\right\} + \left(\frac{\partial}{\partial x}D_{ix} + \frac{\partial}{\partial y}D_{iy} + \frac{\partial}{\partial z}D_{iz}\right)h_{0i} \right] v(x,y,z,t)dV, \quad (80)$$

for 2D composition regions, $$I_{ij}(\bullet) = \iint \left[ \frac{\partial T_i}{\partial t} + D_{ix}\left\{\frac{\partial}{\partial x}h_{0i}\right\} + D_{iy}\left\{\frac{\partial}{\partial y}h_{0i}\right\} + \left(\frac{\partial}{\partial x}D_{ix} + \frac{\partial}{\partial y}D_{iy}\right)h_{0i} \right] v(x,y,t)dA, \quad (81)$$

for 1D composition regions, $$I_{ij}(\bullet) = \int \left[ \frac{\partial T_i}{\partial t} + D_{ix}\left\{\frac{\partial}{\partial x}h_{0i}\right\} + \left(\frac{\partial}{\partial x}D_{ix}\right)h_{0i} \right] v(x,t)dx. \quad (82)$$

Here, v in eqs. (80) to (82) is the weight function being satisfied with $|v(x,y,z,t)|\neq 0$.

Otherwise, according to the second principle, when the distributions Q, i.e., the ratio distributions of the thermal conductivity and density $H_{1ij}$, $H_{1i}$ or $H_1$, the first order partial derivative distributions of the ratio of the thermal conductivity and density, temperature gradient vector distributions sij [Di(x,y,z,t) in 3D composition regions, Di(x,y,t) in 2D composition regions, Di(x,t) in 1D composition regions], temporal first order partial derivative distributions of the temperature sij [$dT_i(x,y,z,t)/dt$ in 3D composition regions, $dT_i(x,y,t)/dt$ in 2D composition regions, $dT_i(x,t)/dt$ in 1D composition regions], divergence distributions of the temperature gradient vector sij or temperature distributions sij [$T_i(x,y,z,t)$ in 3D composition regions, $T_i(x,y,t)$ in 2D composition regions, $T_i(x,t)$ in 1D composition regions] expressed in the first order partial differential equations (45) in the 3D, 2D or 1D composition regions, are finite-element-approximated (based on Galerkin's method) or discrete-approximated [i.e., (a) or (b)], the functionals at time t are derived for $H_{1ij}$, $H_{1i}$ or $H_1$ in 3D composition regions as follows, $$I_{ij}(\bullet) = \iiint \left[ c_i\frac{\partial T_i}{\partial t} + D_{ix}\left\{\frac{\partial}{\partial x}h_{1i}\right\} + D_{iy}\left\{\frac{\partial}{\partial y}h_{1i}\right\} + D_{iz}\left\{\frac{\partial}{\partial z}h_{1i}\right\} + \left(\frac{\partial}{\partial x}D_{ix} + \frac{\partial}{\partial y}D_{iy} + \frac{\partial}{\partial z}D_{iz}\right)h_{1i} \right] v(x,y,z,t)dV, \quad (83)$$

for 2D composition regions, $$I_{ij}(\bullet) = \iint \left[ c_i\frac{\partial T_i}{\partial t} + D_{ix}\left\{\frac{\partial}{\partial x}h_{1i}\right\} + D_{iy}\left\{\frac{\partial}{\partial y}h_{1i}\right\} + \left(\frac{\partial}{\partial x}D_{ix} + \frac{\partial}{\partial y}D_{iy}\right)h_{1i} \right] v(x,y,t)dA, \quad (84)$$

for 1D composition regions, $$I_{ij}(\bullet) = \int \left[ c_i\frac{\partial T_i}{\partial t} + D_{ix}\left\{\frac{\partial}{\partial x}h_{1i}\right\} + \left(\frac{\partial}{\partial x}D_{ix}\right)h_{1i} \right] v(x,t)dx. \quad (85)$$

Here, v in eqs. (83) to (85) is the weight function being satisfied with $|v(x,y,z,t)|\neq 0$.

Otherwise, according to the second principle, when the distributions Q, i.e., the ratio distributions of the thermal conductivity and specific heat $H_{2ij}$, $H_{2i}$ or $H_2$, the first order partial derivative distributions of the ratio of the thermal conductivity and specific heat, temperature gradient vector distributions sij [Di(x,y,z,t) in 3D composition regions, Di(x,y,t) in 2D composition regions, Di(x,t) in 1D composition regions], temporal first order partial derivative distributions of the temperature sij [$dT_i(x,y,z,t)/dt$ in 3D composition regions, $dT_i(x,y,t)/dt$ in 2D composition regions, $dT_i(x,t)/dt$ in 1D composition regions], divergence distributions of the temperature gradient vector sij or temperature distributions sij [$T_i(x,y,z,t)$ in 3D composition regions, $T_i(x,y,t)$ in 2D composition regions, $T_i(x,t)$ in 1D composition regions] expressed in the first order partial differential equations (47) in the 3D, 2D or 1D composition regions, are finite-element-approximated (based on Galerkin's method) or discrete-approximated [i.e., (a) or (b)], the functionals at time t are derived for $H_{2ij}$, $H_{2i}$ or $H_2$ in 3D composition regions as follows, $$I_{ij}(\bullet) = \int\int\int \left[\rho_i \frac{\partial T_i}{\partial t} + D_{ix}\left\{\frac{\partial}{\partial x}h_{2i}\right\} + D_{iy}\left\{\frac{\partial}{\partial y}h_{2i}\right\} + D_{iz}\left\{\frac{\partial}{\partial z}h_{2i}\right\} + \right.$$
$$\left.\left(\frac{\partial}{\partial x}D_{ix} + \frac{\partial}{\partial y}D_{iy} + \frac{\partial}{\partial z}D_{iz}\right)h_{2i}\right]v(x,y,z,t)dV, \quad (86)$$

for 2D composition regions, $$I_{ij}(\bullet) = \int\int \left[\rho_i \frac{\partial T_i}{\partial t} + D_{ix}\left\{\frac{\partial}{\partial x}h_{2i}\right\} + \right.$$
$$\left. D_{iy}\left\{\frac{\partial}{\partial y}h_{2i}\right\} + \left(\frac{\partial}{\partial x}D_{ix} + \frac{\partial}{\partial y}D_{iy}\right)h_{2i}\right]v(x,y,t)dA, \quad (87)$$

for 1D composition regions, $$I_{ij}(\bullet) = \int\left[\rho_i \frac{\partial T_i}{\partial t} + D_{ix}\left\{\frac{\partial}{\partial x}h_{2i}\right\} + \left(\frac{\partial}{\partial x}D_{ix}\right)h_{2i}\right]v(x,t)dx. \quad (88)$$

Here, v in eqs. (86) to (88) is the weight function being satisfied with $|v(x,y,z,t)| \neq 0$.

In respective composition regions, the corresponding functional $Ii(.)$ (77) to (88) is used, where the basis functions used for approximating each distribution Q are used as the weight function v. The prespecified basis functions being independent of the time t can also be used.

Thus, when the spatial partial differential equations (41) are used, the nodal data [the low-pass-filtered temporal first order partial derivative distributions of the temperature $dT_i(I,J,K,j)/dt$, temperature gradient vector distributions $Di(I,J,K)$, divergence distributions of the temperature gradient vector, temperature distributions $T_i(I,J,K,j)$, and occasionally the reference thermal conductivities (distributions) data $k'_i(I,J,K,j)$, $k'_i(I,J,K)$, $k'(I,J,K)$, reference thermal diffusivities (distributions) data $h_0'_i(I,J,K,j)$, $h_0'_i(I,J,K)$, $h_0'(I,J,K)$, products (distributions) data of the density and specific heat $\rho c_i(I,J,K,j)$, $\rho c_i(I,J,K)$, $\rho c(I,J,K)$, densities (distributions) data $\rho_i(I,J,K,j)$, $\rho_i(I,J,K)$, $\rho(I,J,K)$ or specific heats (distributions) data $c_i(I,J,K,j)$, $c_i(I,J,K)$, $c(I,J,K)$] in the ROI are substituted into the nodal distributions Q'' in the finite-element-approximated Iij(.) [eqs. (77) to (79)] using the basis functions, and by dealing with all the algebra equations derived by setting zero the each substituted Iij(.), the algebra equations (76) for the unknown nodal distributions U' over the ROI are derived. Here, when implementing the partial integration to the gradient distributions of the thermal conductivity Lij, Li, L, the basis functions of the thermal conductivity distribution can be direct currents.

Otherwise, when the spatial partial differential equations (43) are used, the nodal data [the low-pass-filtered temporal first order partial derivative distributions of the temperature $dT_i(I,J,K,j)/dt$, temperature gradient vector distributions $Di(I,J,K)$, divergence distributions of the temperature gradient vector, temperature distributions $T_i(I,J,K,j)$, and occasionally the reference thermal diffusivities (distributions) data $h_0'_i(I,J,K,j)$, $h_0'_i(I,J,K)$, $h_0'(I,J,K)$] in the ROI are substituted into the nodal distributions Q'' in the finite-element-approximated Iij(.) [eqs. (80) to (82)] using the basis functions, and by dealing with all the algebra equations derived by setting zero the each substituted Iij(.), the algebra equations (76) for the unknown nodal distributions U' over the ROI are derived. Here, when implementing the partial integration to the gradient distributions of the thermal diffusivity $H_0ij$, $H_0i$, $H_0$, the basis functions of the thermal conductivity distribution can be direct currents.

Otherwise, when the spatial partial differential equations (45) are used, the nodal data [the low-pass-filtered temporal first order partial derivative distributions of the temperature $dT_i(I,J,K,j)/dt$, temperature gradient vector distributions $Di(I,J,K)$, divergence distributions of the temperature gradient vector, temperature distributions $T_i(I,J,K,j)$, and occasionally the reference ratios (distributions) data of the thermal conductivity and density $h_1'_i(I,J,K,j)$, $h_1'_i(I,J,K)$, $h_1'(I,J,K)$, reference specific heats (distributions) data $c_i(I,J,K,j)$, $c_i(I,J,K)$, $c(I,J,K)$] in the ROI are substituted into the nodal distributions Q'' in the finite-element-approximated Iij(.) [eqs. (83) to (85)] using the basis functions, and by dealing with all the algebra equations derived by setting zero the each substituted Iij(.), the algebra equations (76) for the unknown nodal distributions U' over the ROI are derived. Here, when implementing the partial integration to the gradient distributions of the thermal diffusivity $H_1ij$, $H_1i$, $H_1$, the basis functions of the thermal conductivity distribution can be direct currents.

Otherwise, when the spatial partial differential equations (47) are used, the nodal data [the low-pass-filtered temporal first order partial derivative distributions of the temperature $dT_i(I,J,K,j)/dt$, temperature gradient vector distributions $Di(I,J,K)$, divergence distributions of the temperature gradient vector, temperature distributions $T_i(I,J,K,j)$, and occasionally the reference ratios (distributions) data of the thermal conductivity and specific heat $h_2'_i(I,J,K,j)$, $h_2'_i(I,J,K)$, $h_2'(I,J,K)$, reference densities (distributions) data $\rho i(I,J,K,j)$, $\rho i(I,J,K)$, $\rho(I,J,K)$] in the ROI are substituted into the nodal distributions Q'' in the finite-element-approximated Iij(.) [eqs. (86) to (88)] using the basis functions, and by dealing with all the algebra equations derived by setting zero the each substituted Iij(.), the algebra equations (76) for the unknown nodal distributions U' over the ROI are derived. Here, when implementing the partial integration to the gradient distributions of the thermal diffusivity $H_2ij$, $H_2i$, $H_2$, the basis functions of the thermal conductivity distribution can be direct currents.

As above described, according to the first and second principles, the algebra equations (76) can be solved for the unknown nodal vector U' over the ROI as the simultaneous equations. Otherwise, the simultaneous equations in the algebra equations (76) can be solved in the respective composition regions for the unknown nodal distributions Q', i.e., the vector V' composed of the unknown, thermal conductivity nodal distribution L'ij, L'i, L', product nodal distribution of density and specific heat R'ij, R'i, R', density or specific heat nodal distributions S'ij, S'i, S', thermal diffusivity nodal distributions $H_0'ij$, $H_0'i$, $H_0'$, ratio nodal distributions of the thermal conductivity and density $H_1'ij$, $H_1'I$, $H_1'$ or ratio nodal distributions of the thermal conductivity and specific heat $H_2'ij$, $H_2'i$, $H_2'$. Thus, if the configurations of the thermal sources/sinks and reference regions are proper, occasionally, even when only one set of $dTi/dt$, $Ti$, $Di$, $\nabla Di$ is measured, the unknown thermal conductivity distributions Lij [$ki(x,y,z,t)$ when the composition region is 3D], Li [$ki(x,y,z)$], L [$k(x,y,z)$], thermal diffusivity distributions $H_0ij$ [$h_{0i}(x,y,z,t)$], $H_0i$ [$h_{0i}(x,y,z)$], $H_0[h_0(x,y,z)]$, ratio distributions of the thermal conductivity and density $H_1ij$ [$h_{1i}(x,y,z,t)$], $H_1i$ [$h_{1i}(x,y,z)$], $H_1$ [$h_1(x,y,z)$], ratio distributions of the thermal conductivity and specific heat $H_2ij$ [$h_{2i}(x,y,z,t)$], $H_2i$ [$h_{2i}(x,y,z)$], $H_2$ [$h_2(x,y,z)$] can be estimated in the ROI. Occasionally, the unknown product distributions of the density and specific heat Rij [$\rho ci(x,y,z,t)$], Ri [$\rho ci(x,y,z)$], R [$\rho c(x,y,z)$], specific heat distributions Sij [$ci(x,y,z,t)$], Si [$ci(x,y,z)$], S [$c(x,y,z)$], density distributions Sij [$\rho i(x,y,z,t)$], Si [$\rho i(x,y,z)$], S [$\rho(x,y,z)$] can be simultaneously estimated in the ROI. Otherwise, under arbitrary configurations of the thermal sources/sinks and reference regions, when the thermal conductivity distributions Lij [ki(x,y,z,t)], Li [ki(x,y,z)], L [k(x,y,z)], thermal diffusivity distributions $H_0$ij [$h_{0i}$(x,y,z,t)], $H_0$i [$h_0$i(x,y,z)], $H_0$ [$h_0$(x,y,z)], ratio distributions of the thermal conductivity and density $H_1$ij [$h_{1i}$(x,y,z,t)], $H_{1i}$ [$h_{1i}$(x,y,z)], $H_1$ [$h_1$(x,y,z)] or ratio distributions of the thermal conductivity and specific heat $H_2$ij [$h_{2i}$(x,y,z,t)], $H_2$i[$h_{2i}$(x,y,z)], $H_2$ [$h_2$(x,y,z)] are given in the ROI, the unknown product distributions of the density and specific heat Rij [92 ci(x,y,z,t)], Ri [ρci(x,y,z)], R [ρc(x,y,z)], specific heat distributions Sij [ci(x,y,z,t)], Si [ci(x,y,z)], S [c(x,y,z)] or density distributions Sij [ρi(x,y,z,t)], Si [ρi(x,y,z)], S [ρ(x,y,z)] can be estimated in the ROI. Here, when using the finite element approximations, the prespecified basis functions are used. The same as in the case when the ROI is 2D or 1D.

Otherwise, when plural independent sequences of the temperature nodal distributions Ti(I,J,K,j) [i=1~M, j=0~n] are measured, and the plural sequences are used to estimate the unknown nodal distribution U' over the ROI, according to the dependency of U' on i and j, one of the following functionals II(U') [eqs. (89) to (97)] using the algebra equations (76) can be used. That is, the unknown nodal vector U' in the algebra equations (76) expresses in the ROI the unknown nodal distribution, Uij [includes at least one of the unknown nodal distributions Q' being dependent of i and j, i.e., L'ij, R'ij, S'ij, $H_0$'ij, $H_1$'ij, $H_2$'ij and can include the unknown nodal distributions Q' being dependent of only i or being invariant with respect to i and j, i.e., L'i, L', R'i, R', S'i, S', $H_0$'i, $H_0$', $H_1$'i, $H_1$', $H_2$'i, $H_2$'], Ui [includes at least one of the unknown nodal distributions Q' being dependent of i, i.e., L'ij, L'i, R'ij, R'i, S'ij, S'i, $H_0$'ij, $H_0$'i, $H_1$'ij, $H_1$'i, $H_2$'ij, $H_2$'i and can include the unknown nodal distributions Q' being invariant with respect to i and j, i.e., L', R', S', $H_0$', $H_1$', $H_2$'], U [includes at least one of the unknown nodal distributions Q' being invariant with respect to i and j, i.e., L', R', S', $H_0$', $H_1$', $H_2$'] or Uj [Uij being invariant with respect to i]. Thus, the functionals are minimized with respect to one of Uij, Ui, U or Uj.

Here, Pij of the functionals IIij(U') [eqs. (89) to (97)] for, in eqs. (76), the respective algebra equations derived only for one of the unknown nodal distributions R'ij, R'i, R', R'j (from the functionals Iij(.) [eqs. (49) to (75) or (77) to (88)]), are the powers of the temporal first order partial derivative distributions of the temperature $dT_{ij}$(x,y,z,t)/dt of the respective composition regions (integral regions). If possible, Pi is multiplied to the standard deviation of the respective power.

Otherwise, Pij of the functionals IIij(U') [eqs. (89) to (97)] for, in eqs. (76), the respective algebra equations derived only for one of the unknown nodal distributions S'ij, S'i, S', S'j (from the functionals Iij(.) [eqs. (49) to (75) or (77) to (88)]), are the powers of the product distributions of either density ρ or specific heat c and temporal first order partial derivative of the temperature of the respective composition regions (integral regions). If possible, Pi is multiplied to the standard deviation of the respective power.

Otherwise, Pij of the functionals IIij(U') [eqs. (89) to (97)] for, in eqs. (76), the respective algebra equations derived for both one of the unknown nodal distributions R'ij, R'i, R', R'j, S'ij, S'i, S', S'j and one of the unknown nodal distributions L'ij, L'i, L', L'j, $H_1$'$_{ij}$, $H_1$'$_I$, $H_1$', $H_1$'$_j$, $H_2$'$_{ij}$, $H_2$'$_I$, $H_2$', $H_2$'$_j$ (from the functionals Iij(.) [eqs. (49) to (71) or (77) to (88)]), are the summation of the powers of the product distributions of one of the product of the density ρ and specific heat c, density ρ or specific heat c and the temporal first order partial derivative of the temperature (if possible, Pi is multiplied to the standard deviation of the respective power), the powers of the inner product distributions of the temperature gradient vector Di(x,y,z,t) and gradient vector for the unknown thermal conductivity k, ratio h1 of the thermal conductivity and density, ratio h2 of the thermal conductivity and specific heat (if possible, Pi is multiplied to the standard deviation of the respective power) and the powers of the distributions of the divergence of the temperature gradient vector (if possible, Pi is multiplied to the standard deviation of the respective power) of the respective composition regions (integral regions).

Otherwise, Pij of the functionals IIij(U') [eqs. (89) to (97)] for, in eqs. (76), the respective algebra equations derived for one of the unknown nodal distributions L'ij, L'i, L', L'j, $H_0$'$_{ij}$, $H_0$'$_I$, $H_0$', $H_0$'$_j$, $H_1$'$_{ij}$, $H_1$'$_I$, $H_1$', $H_1$'$_j$, $H_2$'$_{ij}$, $H_2$'$_I$, $H_2$', $H_2$'$_j$ (from the functionals Iij(.) [eqs. (49) to (71) or (77) to (88)]), are the summation of the powers of the inner product distributions of the temperature gradient vector Di(x,y,z,t) and gradient vector for the unknown thermal conductivity k, thermal diffusivity $h_0$, ratio $h_1$ of the thermal conductivity and density, ratio $h_2$ of the thermal conductivity and specific heat (if possible, Pi is multiplied to the standard deviation of the respective power) and the powers of the distributions of the divergence of the temperature gradient vector (if possible, Pi is multiplied to the standard deviation of the respective power) of the respective composition regions (integral regions).

Otherwise, Pij of the functionals IIij(U') [eqs. (89) to (97)] for, in eqs. (76), the respective algebra equations derived for both one of the unknown nodal distributions R'ij, R'i, R', R'j, S'ij, S'i, S', S'j and one of the unknown nodal distributions L'ij, L'i, L', L'j, $H_1$'$_{ij}$, $H_1$'$_I$, $H_1$', $H_1$'$_j$, $H_2$'$_{ij}$, $H_2$'$_I$, $H_2$', $H_2$'$_j$ (from the functionals Iij(.) [eqs. (72) to (75)]), are the summation of the powers of the product distributions of one of the product of the density ρ and specific heat c, density ρ or specific heat c and the temporal first order partial derivative of the temperature (if possible, Pi is multiplied to the standard deviation of the respective power) and the powers of the distributions of the temperature gradient vector Di(x,y,z,t) (if possible, Pi is multiplied to the standard deviation of the respective power).

Otherwise, Pij of the functionals IIij(U') [eqs. (89) to (97)] for, in eqs. (76), the respective algebra equations derived for one of the unknown nodal distributions L'ij, L'i, L', L'j, $H_0$'$_{ij}$, $H_0$'$_I$, $H_0$', $H_0$'$_j$, $H_1$'$_{ij}$, $H_1$'$_I$, $H_1$', $H_1$'$_j$, $H_2$'$_{ij}$, $H_2$'$_I$, $H_2$', $H_2$'$_j$ (from the functionals Iij(.) [eqs. (72) to (75)]), are the powers of the distributions of the temperature gradient vector Di(x,y,z,t) (if possible, Pi is multiplied to the standard deviation of the respective power) of the respective composition regions (integral regions).

Thus, generally, the algebra equations in the functionals are normalized by Pij.

With respect to the unknown nodal distributions Uij (i=1~M, j=j=0~n), the following functional holds.

$$II_{ij}(U_{ij}) = \frac{1}{P_{ij}}\|e_{ij} - E_{ij}U_{ij}\|^2 \quad (89)$$

$$(\text{or } II_{ij}(U_{ij}) = \|e_{ij} - E_{ij}U_{ij}\|^2)$$

Here, the unknown nodal distributions Uij can be invariant with respect to either i or j, or both i and j, and then occasionally, measured one set of temperature data dTi/dt, Ti, Di, ∇Di can also be used.

Otherwise, with respect to the unknown nodal distributions Uij (i=1~M, j=j=0~n), the following functional holds.

$$\Pi_j\left(\begin{bmatrix} U_{1j} \\ U_{2j} \\ \vdots \\ U_{Mj} \end{bmatrix}\right) = \sum_{i=1}^{M} \frac{1}{Pij}\|e_{ij} - E_{ij}U_{ij}\|^2 \quad (90)$$

$$\left(\text{or } \Pi_j\left(\begin{bmatrix} U_{1j} \\ U_{2j} \\ \vdots \\ U_{Mj} \end{bmatrix}\right) = \sum_{i=1}^{M} \|e_{ij} - E_{ij}U_{ij}\|^2\right)$$

Here, the unknown nodal distributions Uij can be invariant with respect to j.

Otherwise, with respect to the unknown nodal distributions Uj (j=j=0~n) [when Uij is invariant with respect to i], the following functional holds.

$$\Pi_j(U_j) = \sum_{i=1}^{M} \frac{1}{Pij}\|e_{ij} - E_{ij}U_j\|^2 \quad (91)$$

$$\left(\text{or } \Pi_j(U_j) = \sum_{i=1}^{M} \|e_{ij} - E_{ij}U_j\|^2\right)$$

Here, the unknown nodal distributions Uj can be invariant with respect to j.

Otherwise, with respect to the unknown nodal distributions Uij (i=1~M, j=j=0~n), the following functional holds.

$$\Pi_i\left(\begin{bmatrix} U_{i0} \\ U_{i1} \\ \vdots \\ U_{in} \end{bmatrix}\right) = \sum_{j=0}^{n} \frac{1}{Pij}\|e_{ij} - E_{ij}U_{ij}\|^2 \quad (92)$$

$$\left(\text{or } \Pi_j\left(\begin{bmatrix} U_{i0} \\ U_{i1} \\ \vdots \\ U_{in} \end{bmatrix}\right) = \sum_{j=0}^{n} \|e_{ij} - E_{ij}U_{ij}\|^2\right)$$

Here, the unknown nodal distributions Uij can be invariant with respect to i.

Otherwise, with respect to the unknown nodal distributions Ui (i=1~M) [when Uij is invariant with respect to j], the following functional holds.

$$\Pi_i(U_i) = \sum_{j=0}^{n} \frac{1}{Pij}\|e_{ij} - E_{ij}U_i\|^2 \quad (93)$$

$$\left(\text{or } \Pi_i(U_i) = \sum_{j=0}^{n} \|e_{ij} - E_{ij}U_i\|^2\right)$$

Here, the unknown nodal distribution Ui can be invariant with respect to i.

Otherwise, with respect to the unknown nodal distributions Uij (i=1~M, j=j=0~n), the following functional holds.

$$\Pi\left(\begin{bmatrix} U_{10} \\ U_{11} \\ \vdots \\ U_{1n} \\ U_{20} \\ U_{21} \\ \vdots \\ U_{2n} \\ \vdots \\ U_{M0} \\ U_{M1} \\ \vdots \\ U_{Mn} \end{bmatrix}\right) = \sum_{i=1, j=0}^{M,n} \frac{1}{Pij}\|e_{ij} - E_{ij}U_{ij}\|^2 \quad (94)$$

$$\left(\text{or } \Pi\left(\begin{bmatrix} U_{10} \\ U_{11} \\ \vdots \\ U_{1n} \\ U_{20} \\ U_{21} \\ \vdots \\ U_{2n} \\ \vdots \\ U_{M0} \\ U_{M1} \\ \vdots \\ U_{Mn} \end{bmatrix}\right) = \sum_{i=1, j=0}^{M,n} \|e_{ij} - E_{ij}U_{ij}\|^2\right)$$

Otherwise, with respect to the unknown nodal distributions Uj (j=j=0~n) [when Uij is invariant with respect to i], the following functional holds.

$$\Pi\left(\begin{bmatrix} U_1 \\ U_2 \\ \vdots \\ U_n \end{bmatrix}\right) = \sum_{i=1, j=0}^{M,n} \frac{1}{Pij}\|e_{ij} - E_{ij}U_j\|^2 \quad (95)$$

$$\left(\text{又、} \Pi\left(\begin{bmatrix} U_1 \\ U_2 \\ \vdots \\ U_n \end{bmatrix}\right) = \sum_{i=1, j=0}^{M,n} \|e_{ij} - E_{ij}U_j\|^2\right)$$

Otherwise, with respect to the unknown nodal distributions Ui (i=1~M) [when Uij is in variant with respect to j], the following functional holds.

$$\Pi\left(\begin{bmatrix} U_1 \\ U_2 \\ \vdots \\ U_n \end{bmatrix}\right) = \sum_{i=1, j=0}^{M,n} \frac{1}{Pij}\|e_{ij} - E_{ij}U_i\|^2 \quad (96)$$

$$\left(\text{or } \Pi\left(\begin{bmatrix} U_1 \\ U_2 \\ \vdots \\ U_M \end{bmatrix}\right) = \sum_{i=1,j=0}^{M,n} \|e_{ij} - E_{ij}U_i\|^2\right)$$

Otherwise, with respect to the unknown nodal distributions U [when Uij is in variant with respect to both i and j], the following functional holds.

$$\Pi(U) = \sum_{i=1,j=0}^{M,n} \frac{1}{P_{ij}} \|e_{ij} - E_{ij}U\|^2 \quad (97)$$

$$\left(\text{or } \Pi(U) = \sum_{i=1,j=0}^{M,n} \|e_{ij} - E_{ij}U\|^2\right)$$

By minimizing the functionals $\Pi(U')$ [eq. (89) to (97)] with respect to the unknown nodal vector U' [one of the unknown nodal distributions Uij, Ui, U, Uj], as described below, the normal equations are derived for U'.

From the functional $\Pi_{ij}(U_{ij})$ of eq. (89), the following normal equations are derived for the unknown nodal distribution Uij (i=1~M, j=0~n) [Here, Uij can be invariant with respect to either i or j or both i and j, and then occasionally only one set of temperature data dTi/dt, Ti, Di, ∇Di can also be used].

$$E'_{ij}U_{ij} = e'_{ij} \quad (98)$$

Here, the matrix, $$E'_{ij} = \frac{1}{P_{ij}} E^T_{ij} E_{ij}$$

and the vector $$e'_{ij} = \frac{1}{P_{ij}} E^T_{ij} e_{ij}.$$

From the functional $\Pi_j(U_{ij})$ of eq. (90), the following normal equations are derived for the unknown nodal distribution Uij (i=1~M, j=0~n) [Here, Uij can be invariant with respect to j].

$$\begin{bmatrix} E'_{1j} & & & 0 \\ & E'_{2j} & & \\ & & \ddots & \\ 0 & & & E'_{Mj} \end{bmatrix} \begin{bmatrix} U_{1j} \\ U_{2j} \\ \vdots \\ U_{Mj} \end{bmatrix} = \begin{bmatrix} e'_{1j} \\ e'_{2j} \\ \vdots \\ e'_{Mj} \end{bmatrix} \quad (99)$$

Here, the local matrix E'ij and vector $e'_{ij}$ (i=1~M, j=0~n) are respectively those of the normal equations (98).

From the functional $\Pi_j(U_j)$ of eq. (91), the following normal equations are derived for the unknown nodal distribution Uj (j=0~n) [Here, Uj can be invariant with respect to j].

$$E_j U_j = e_j \quad (100)$$

Here, the matrix $E_j$ and the vector $e_j$ (j=0~n) are respectively $\Sigma_{i=1}^{M} E'_{ij}$ and $\Sigma_{i=1}^{M} e'_{ij}$ using the matrix $E'_{ij}$ and the vector $e'_{ij}$ of the normal equations (98).

From the functional $\Pi_i(U_{ij})$ of eq. (92), the following nomal equations are derived for the unknown nodal distribution Uij (i=1~M, j=0~n) [Here, Uij can be invariant with respect to i].

$$\begin{bmatrix} E'_{i0} & & & 0 \\ & E'_{i1} & & \\ & & \ddots & \\ 0 & & & E'_{in} \end{bmatrix} \begin{bmatrix} U_{i0} \\ U_{i1} \\ \vdots \\ U_{in} \end{bmatrix} = \begin{bmatrix} e'_{i0} \\ e'_{i1} \\ \vdots \\ e'_{in} \end{bmatrix} \quad (101)$$

Here, the matrix $E'_{ij}$ and the vector $e'_{ij}$ (i=1~M, j=0~n) are respectively those of the normal equations (98).

From the functional $\Pi_i(U_i)$ of eq. (93), the following normal equations are derived for the unknown nodal distribution Ui (i=1~M) [Here, Ui can be invariant with respect to i].

$$E_i U_i = e_i \quad (102)$$

Here, the matrix $E_i$ and the vector $e_i$ (i=1~M) are respectively $\Sigma_{j=0}^{n} E'_{ij}$ and $\Sigma_{j=0}^{n} e'_{ij}$ using the matrix $E'_{ij}$ and the vector $e'_{ij}$ of the normal equations (98).

From the functional $\Pi(U_{ij})$ of eq. (94), the following nomal equations are derived for the unknown nodal distribution Uij (i=1~M, j=0~n).

$$\begin{bmatrix} E'_{10} & & & & & & & & \\ & E'_{11} & & & & & & & \\ & & \ddots & & & & & 0 & \\ & & & E'_{1n} & & & & & \\ & & & & E'_{20} & & & & \\ & & & & & E'_{21} & & & \\ & & & & & & \ddots & & \\ & & & & & & & E'_{2n} & \\ & & & & & & & & \ddots \\ & & & & & & & & & E'_{M0} \\ & 0 & & & & & & & & & E'_{M1} \\ & & & & & & & & & & & \ddots \\ & & & & & & & & & & & & E'_{Mn} \end{bmatrix} \quad (103)$$

-continued $$\begin{bmatrix} U_{10} \\ U_{11} \\ \vdots \\ U_{1n} \\ U_{20} \\ U_{21} \\ \vdots \\ U_{2n} \\ \vdots \\ U_{M0} \\ U_{M1} \\ \vdots \\ U_{Mn} \end{bmatrix} = \begin{bmatrix} e'_{10} \\ e'_{11} \\ \vdots \\ e'_{1n} \\ e'_{20} \\ e'_{21} \\ \vdots \\ e'_{2n} \\ \vdots \\ e'_{M0} \\ e'_{M1} \\ \vdots \\ e'_{Mn} \end{bmatrix}$$

Here, the matrix $E'_{ij}$ and the vector $e'_{ij}$ (i=1~M, j=0~n) are respectively those of the normal equations (98).

From the functional $II(Uj)$ of eq. (95), the following nomal equations are derived for the unknown nodal distribution Uj (j=0~n).

$$\begin{bmatrix} E_0 & & & 0 \\ & E_1 & & \\ & & \ddots & \\ 0 & & & E_n \end{bmatrix} \begin{bmatrix} U_0 \\ U_1 \\ \vdots \\ U_n \end{bmatrix} = \begin{bmatrix} e_0 \\ e_1 \\ \vdots \\ e_n \end{bmatrix} \quad (104)$$

Here, the matrix $E_j$ and the vector $e_j$ (j=0~n) are respectively $\sum_{i=1}^{M} E'_{ij}$ and $\sum_{i=1}^{M} e'_{ij}$ using the matrix $E'_{ij}$ and the vector $e'_{ij}$ of the normal equation (98).

From the functional $II(Ui)$ of eq. (96), the following nomal equations are derived for the unknown nodal distribution Ui (i=1~M).

$$\begin{bmatrix} E_1 & & & 0 \\ & E_2 & & \\ & & \ddots & \\ 0 & & & E_M \end{bmatrix} \begin{bmatrix} U_1 \\ U_2 \\ \vdots \\ U_M \end{bmatrix} = \begin{bmatrix} e_1 \\ e_2 \\ \vdots \\ e_M \end{bmatrix} \quad (105)$$

Here, the matrix Ei and the vector ei (i=1~M) are respectively $\sum_{j=0}^{n} E'_{ij}$ and $\sum_{j=0}^{n} e'_{ij}$ using the matrix $E'_{ij}$ and the vector $e'_{ij}$ of the normal equations (98).

From the functional $II(U)$ of eq. (97), the following nomal equations are derived for the unknown nodal distribution U.

$$EU = e \quad (106)$$

Here, the matrix E and the vector e are respectively $\sum_{i=1}^{M}\sum_{j=0}^{n} E'_{ij}$ and $\sum_{i=1}^{M}\sum_{j=0}^{n} e'_{ij}$ using the matrix $E'_{ij}$ and the vector $e'_{ij}$ of the normal equations (98).

By solving the above-described normal equations (98) to (106) for the unknown nodal vector U', one of the unknown nodal distributions Uij, Ui, U and Uj is estimated. Here, the unknown nodal distribution Uij includes at least one of the unknown nodal distributions Q' being dependent of i and j, i.e., L'ij, R'ij, S'ij, $H_0$'ij, $H_1$'ij, $H_2$'ij and can include the unknown nodal distributions being dependent of only i or being invariant with respect to both i and j, i.e., L'i, L', R'i, R', S'i, S', $H_0$'i, $H_0$', $H_1$'i, $H_1$', $H_2$'i, $H_2$'. The unknown nodal distribution Ui includes at least one of the distributions Q' being dependent of i, i.e., L'ij, L'i, R'ij, R'i, S'ij, S'i, $H_0$'ij, $H_0$'i, $H_1$'ij, $H_1$'i, $H_2$'ij, $H_2$'I and can include the unknown nodal distributions Q' being invariant with respect to both i and j, i.e., L', R', S', $H_0$', $H_1$', $H_2$'. The unknown nodal distribution U includes at least one of the unknown nodal distributions Q' being invariant with respect to both i and j, i.e., L', R', S', $H_0$', $H_1$', $H_2$'. The unknown nodal distribution Uj corresponds to Uij being invariant with respect to i.

Here, the functionals $II(U')$ (89) to (97) with respect to the unknown nodal vector U' for over the ROI can also be dealt with as the functionals $II(V')$ derived from the algebra equations for the unknown nodal distributions V' in each composition region, i.e., Vij, Vi, V or Vj. According to the dependency of the unknown nodal distribution V' on i and j, the respective functionals are minimized with respect to the unknown nodal distributions Vij, Vi, V or Vj. As the result, the nomal equations (98) to (106) for the unknown nodal vector V' in each composition region are derived. By solving the nomal equations, one of the unknown nodal distributions Vij, Vi, V or Vj is estimated. Here, the unknown nodal vector Vij includes at least one of the unknown nodal distributions Q' being dependent of i and j, i.e., L'ij, R'ij, S'ij, $H_0$'ij, $H_1$'ij, $H_2$'ij and can include the unknown nodal distributions Q' being dependent of only i or being invariant with respect to both i and j, i.e., L'i, L', R'i, R', S'i, S', $H_0$'i, $H_0$', $H_1$'i, $H_1$', $H_2$'i, $H_2$'. The unknown nodal distribution Vi includes at least one of the unknown nodal distributions Q' being dependent of i, i.e., L'ij, L'i, R'ij, R'i, S'ij, S'i, $H_0$'ij, $H_0$'i, $H_1$'ij, $H_1$'i, $H_2$'ij, $H_2$'I and can include the unknown nodal distributions being invariant with respect to both i and j, i.e., L', R', S', $H_0$', $H_1$', $H_2$'. The unknown nodal distribution V includes at least one of the unknown nodal distributions Q' being invariant with respect to both i and j, i.e., L', R', S', $H_0$'', $H_1$', $H_2$'. The unknown nodal distribution Vj corresponds to Vij being invariant with respect to i.

Thus, if the configurations of the thermal sources/sinks and reference regions are proper, occasionally, even when only one set of dTi/dt, Ti, Di, $\nabla$Di is measured, the unknown thermal conductivity distributions Lij [ki(x,y,z,t)] when the composition region is 3D], Li [ki(x,y,z)], L [k(x,y,z)], Lj [k(x,y,z,t)], thermal diffusivity distributions $H_0$ij [$h_{0i}$(x,y,z,t)], $H_{0i}$ [$h_{0i}$(x,y,z)], $H_0$ [$h_0$(x,y,z)], $H_{0j}$ [$h_0$(x,y,z,t)], ratio distributions of the thermal conductivity and density $H_1$ij [$h_{1i}$(x,y,z,t)], $H_1$i [$h_{1i}$(x,y,z)], $H_1$ [$h_1$(x,y,z)], $H_{1j}$ [$h_1$(x,y,z,t)], ratio distributions of the thermal conductivity and specific heat $H_2$ij [$h_{2i}$(x,y,z,t)], $H_2$i [$h_{2i}$(x,y,z)], $H_2$ [$h_2$(x,y,z)], $H_{2j}$ [$h_2$(x,y,z,t)] can be estimated in the ROI. Occasionally, the unknown product distributions of the density and specific heat Rij [ρci (x,y,z,t)], Ri [ρci(x,y,z)], R [ρc(x,y,z)], Rj [ρc(x,y,z,t)], specific heat distributions Sij [ci (x,y,z,t)], Si [ci(x,y,z)], S [c(x,y,z)], Sj [c (x,y,z,t)], density distributions Sij [ρi(x,y,z,t)], Si [ρi(x,y,z)], S [ρ(x,y,z)], Sj [ρ(x,y,z,t)] can be simultaneously estimated in the ROI. Otherwise, under arbitrary configurations of the thermal sources/sinks and reference regions, when the thermal conductivity distributions Lij [ki(x,y,z,t)], Li [ki (x,y,z)], L [k(x,y,z)], Lj [k(x,y,z,t)], thermal diffusivity distributions $H_0$ij [$h_{0i}$(x,y,z,t)], $H_0$i [$h_{0i}$(x,y,z)], $H_0$ [$h_0$(x,y, z)], $H_{0j}$ [$h_0$ (x,y,z,t)], ratio distributions of the thermal conductivity and density $H_1$ij [$h_1$i(x,y,z,t)], $H_1$i [$h_{1i}$(x,y,z)], $H_1$ [$h_1$(x,y,z)], $H_{1j}$ [$h_1$(x,y,z,t)] or ratio distributions of the thermal conductivity and specific heat $H_2$ij [$h_{2i}$(x,y,z,t)], $H_2$i [$h_{2i}$(x,y,z)], $H_2$ [$h_2$(x,y,z)], $H_{2j}$ [$h_2$(x,y,z,t)] are given in the ROI, the unknown product distributions of the density and specific heat Rij [ρci(x,y,z,t)], Ri [ρci(x,y,z)], R [ρc(x,y,z)], Rj [ρc(x,y,z,t)], specific heat distributions Sij [ci(x,y,z,t)], Si [ci(x,y,z)], S [c(x,y,z)], Sj [c(x,y,z,t)] or density distributions Sij [ρi(x,y,z,t)], Si [ρi(x,y,z)], S [ρ(x,y,z)], Sj [ρ(x,y,z,t)] can be estimated in the ROI. Here, when using the finite element approximations, the prespecified basis functions are used. The same as in the case when the ROI is 2D or 1D.

The matrixes E, Eij, Ei, Ej and vectors e, eij, ei, ej of the normal equations (98) to (106) derived by minimizing the functionals II(U') or II(V') with respect to U' or V' [eqs. (89) to (97)] are composed of the low-pass-filtered temporal first order partial derivative distributions data of temperature, temperature gradient vector distributions data and divergence distributions data of the temperature gradient vector. Then, the inverse of the matrixes E, Eij, Ei and Ej respectively amplify the high frequency noise remained in the vectors e, eij, ei and ej. Moreover, particularly when dealing with eq. (98), (99), (101) and (103), the configurations of the thermal sources/sinks and reference regions possibly become improper ones. As the results, the estimates of the unknown nodal distributions Uij, Ui, Uj, U, Vij, Vi, Vj, V become unstable.

Thus, as in the first and second principles, occasionally, the reconstruction (estimation) can be stabilized by applying the regularization to the normal equations (98) to (106). That is, as described below, the penalty terms considered in the continuous coordinate system are used together with the regularization parameters $\alpha_{1ij}$, $\alpha_{2ij}$, $\alpha_{3ij}$, $\beta_{1ij}$, $\beta_{2ij}$, $\beta_{3ij}$, $\chi_{1ij}$, $\chi_{2ij}$, $\chi_{3ij}$, $\delta_{1ij}$, $\delta_{2ij}$, $\delta_{3ij}$, $\epsilon_{1ij}$, $\epsilon_{2ij}$, $\epsilon_{3ij}$, $\gamma_{1ij}$, $\gamma_{2ij}$, $\gamma_{3ij}$, $\eta_{1ij}$, $\eta_{2ij}$, $\eta_{3ij}$ (positive values) being possibly set for each measured temperature distribution Tij.

That is, when the unknown nodal vector U' or V' includes the unknown thermal conductivity distribution L'ij, L'i, L' or L'j, for instance, when the ROI is 3D and there exists at least one 3D composition region of unknown thermal conductivity distribution ki(x,y,z,t) [ki(I,J,K,j)], ki(x,y,z) [ki(I,J,K)], k(x,y,z) [k(I,J,K)] or k(x,y,z,t) [k(I,J,K,j)], the integration in each composition region is used as the penalty term (25).

$$\int\int\int \left[\alpha_{1ij}k^2 + \alpha_{2ij}\left\{\left(\frac{\partial}{\partial x}k\right)^2 + \left(\frac{\partial}{\partial y}k\right)^2 + \left(\frac{\partial}{\partial z}k\right)^2\right\} + \alpha_{3ij}\left\{\frac{\partial^2}{\partial x^2}k + \frac{\partial^2}{\partial y^2}k + \frac{\partial^2}{\partial z^2}k\right\}^2\right]dV \quad (107)$$

Here, k is the thermal conductivity at each point, i.e., ki(x,y,z,t), ki(x,y,z), k(x,y,z) or k(x,y,z,t)

When there exists at least one 2D composition region of unknown thermal conductivity distribution ki(x,y,t) [ki(I,J,j)], ki(x,y) [ki(I,J)], k(x,y) [k(I,J)] or k(x,y,t) [k(I,J,j)], the integration in each composition region is used as the penalty term (26).

$$\int\int \left[\alpha_{1ij}k^2 + \alpha_{2ij}\left\{\left(\frac{\partial}{\partial x}k\right)^2 + \left(\frac{\partial}{\partial y}k\right)^2\right\} + \alpha_{3ij}\left\{\frac{\partial^2}{\partial x^2}k + \frac{\partial^2}{\partial y^2}k\right\}^2\right]dA \quad (108)$$

Here, k is the thermal conductivity at each point, i.e., ki(x,y,t), ki(x,y), k(x,y) or k(x,y,t).

When there exists at least one 1D composition region of unknown thermal conductivity distribution ki(x,t) [ki(I,j)], ki(x) [ki(I)], k(x) [k(I)] or k(x,t) [k(I,j)], the integration in each composition region is used as the penalty term (27).

$$\int \left[\alpha_{1ij}k^2 + \alpha_{2ij}\left\{\frac{\partial}{\partial x}k\right\}^2 + \alpha_{3ij}\left\{\frac{\partial^2}{\partial x^2}k\right\}^2\right]dx \quad (109)$$

Here, k is the thermal conductivity at each point, i.e., ki(x,t), ki(x), k(x) or k(x,t).

Otherwise, when the unknown nodal vector U' or V' includes the unknown product distribution of the density and specific heat R'ij, R'i, R' or R'j, for instance, when the ROI is 3D and there exists at least one 3D composition region of unknown product distribution of the density and specific heat ρci(x,y,z,t) [ρci(I,J,K,j)], ρci(x,y,z) [ρci(I,J,K)], ρc(x,y,z) [ρc(I,J,K)], ρc(x,y,z,t) [ρc(I,J,K,j)], the integration in each composition region is used as the penalty term for the product of the density and specific heat.

$$\int\int\int \left[\beta_{1ij}(\rho c)^2 + \beta_{2ij}\left\{\left(\frac{\partial}{\partial x}(\rho c)\right)^2 + \left(\frac{\partial}{\partial y}(\rho c)\right)^2 + \left(\frac{\partial}{\partial z}(\rho c)\right)^2\right\} + \beta_{3ij}\left\{\frac{\partial^2}{\partial x^2}(\rho c) + \frac{\partial^2}{\partial y^2}(\rho c) + \frac{\partial^2}{\partial z^2}(\rho c)\right\}^2\right]dV \quad (110)$$

Here, ρc is the product of the density and specific heat at each point, i.e., ρci(x,y,z,t), ρci(x,y,z), ρc(x,y,z) or ρc(x,y,z,t). The same as in the case when the 3D ROI includes the 2D or 1D composition region. The same as in the case when the ROI is 2D or 1D.

Otherwise, when the unknown nodal vector U' or V' includes the unknown density distribution S'ij, S'i, S' or S'j, for instance, when the ROI is 3D and there exists at least one 3D composition region of unknown density distribution ρi(x,y,z,t) [ρi(I,J,K,j)], ρi(x,y,z) [ρi(I,J,K)], ρ(x,y,z) [ρ(I,J,K)], ρ(x,y,z,t) [ρ(I,J,K,j)], the integration in each composition region is used as the penalty term for the density.

$$\int\int\int \left[\chi_{1ij}\rho^2 + \chi_{2ij}\left\{\left(\frac{\partial}{\partial x}\rho\right)^2 + \left(\frac{\partial}{\partial y}\rho\right)^2 + \left(\frac{\partial}{\partial z}\rho\right)^2\right\} + \chi_{3ij}\left\{\frac{\partial^2}{\partial x^2}\rho + \frac{\partial^2}{\partial y^2}\rho + \frac{\partial^2}{\partial z^2}\rho\right\}^2\right]dV \quad (111)$$

Here, ρ is the density at each point, i.e., ρi(x,y,z,t), ρi(x,y,z), ρ(x,y,z) or ρ(x,y,z,t). The same as in the case when the 3D ROI includes the 2D or 1D composition region. The same as in the case when the ROI is 2D or 1D.

Otherwise, when the unknown nodal vector U' or V' includes the unknown specific heat distribution S'ij, S'i, S' or S'j, for instance, when the ROI is 3D and there exists at least one 3D composition region of unknown specific heat distribution ci(x,y,z,t) [ci(I,J,K,j)], ci(x,y,z) [ci(I,J,K)], c(x,y,z) [c(I,J,K)], c(x,y,z,t) [c(I,J,K,j)], the integration in each composition region is used as the penalty term for the specific heat.

$$\int\int\int \left[\delta_{1ij}c^2 + \delta_{2ij}\left\{\left(\frac{\partial}{\partial x}c\right)^2 + \left(\frac{\partial}{\partial y}c\right)^2 + \left(\frac{\partial}{\partial z}c\right)^2\right\} + \delta_{3ij}\left\{\frac{\partial^2}{\partial x^2}c + \frac{\partial^2}{\partial y^2}c + \frac{\partial^2}{\partial z^2}c\right\}^2\right]dV \quad (112)$$

Here, c is the specific heat at each point, i.e., ci(x,y,z,t), ci(x,y,z), c(x,y,z) or c(x,y,z,t). The same as in the case when the 3D ROI includes the 2D or 1D composition region. The same as in the case when the ROI is 2D or 1D.

Otherwise, when the unknown nodal vector U' or V' includes the unknown thermal diffusivity distribution $H_0'ij$, $H_0'i$, $H_0'$ or $H_0'j$, for instance, when the ROI is 3D and there exists at least one 3D composition region of unknown thermal diffusivity distribution $h_0i(x,y,z,t)$ [$h_0i(I,J,K,j)$], $h_0i(x,y,z)$ [$h_0i(I,J,K)$], $h_0(x,y,z)$ [$h_0(I,J,K)$], $h_0(x,y,z,t)$ [$h_0(I,J,K,j)$], the integration in each composition region is used as the penalty term for the thermal diffusivity.

$$\int\int\int \left[\varepsilon_{1ij}h_0^2 + \varepsilon_{2ij}\left\{\left(\frac{\partial}{\partial x}h_0\right)^2 + \left(\frac{\partial}{\partial y}h_0\right)^2 + \left(\frac{\partial}{\partial z}h_0\right)^2\right\} + \varepsilon_{3ij}\left\{\frac{\partial^2}{\partial x^2}h_0 + \frac{\partial^2}{\partial y^2}h_0 + \frac{\partial^2}{\partial z^2}h_0\right\}^2\right]dV \quad (113)$$

Here, $h_0$ is the thermal diffusivity at each point, i.e., $h_0i(x,y,z,t)$, $h_0i(x,y,z)$, $h_0(x,y,z)$, $h_0(x,y,z,t)$. The same as in the case when the 3D ROI includes the 2D or 1D composition region. The same as in the case when the ROI is 2D or 1D.

Otherwise, when the unknown nodal vector U' or V' includes the unknown ratio distribution of the thermal conductivity and density $H_1'ij$, $H_1'i$, $H_1'$ or $H_1'j$, for instance, when the ROI is 3D and there exists at least one 3D composition region of unknown ratio distribution of the thermal conductivity and density $h_1i(x,y,z,t)$ [$h_1i(I,J,K,j)$], $h_1i(x,y,z)$ [$h_1i(I,J,K)$], $h_1(x,y,z)$ [$h_1(I,J,K)$], $h_1(x,y,z,t)$ [$h_1(I,J,K,j)$], the integration in each composition region is used as the penalty term for the ratio of the thermal conductivity and density.

$$\int\int\int \left[\gamma_{1ij}h_1^2 + \gamma_{2ij}\left\{\left(\frac{\partial}{\partial x}h_1\right)^2 + \left(\frac{\partial}{\partial y}h_1\right)^2 + \left(\frac{\partial}{\partial z}h_1\right)^2\right\} + \gamma_{3ij}\left\{\frac{\partial^2}{\partial x^2}h_1 + \frac{\partial^2}{\partial y^2}h_1 + \frac{\partial^2}{\partial z^2}h_1\right\}^2\right]dV \quad (114)$$

Here, $h_1$ is the ratio of the thermal conductivity and density at each point, i.e., $h_{1i}(x,y,z,t)$, $h_{1i}(x,y,z)$, $h_1(x,y,z)$, $h_1(x,y,z,t)$. The same as in the case when the 3D ROI includes the 2D or 1D composition region. The same as in the case when the ROI is 2D or 1D.

Otherwise, when the unknown nodal vector U' or V' includes the unknown ratio distribution of the thermal conductivity and specific heat $H_2'ij$, $H_2'i$, $H_2'$ or $H_2'j$, for instance, when the ROI is 3D and there exists at least one 3D composition region of unknown ratio distribution of the thermal conductivity and specific heat $h_2i(x,y,z,t)$ [$h_2i(I,J,K,j)$], $h_2i(x,y,z)$ [$h_2i(I,J,K)$], $h_2(x,y,z)$ [$h_2(I,J,K)$], $h_2(x,y,z,t)$ [$h_2(I,J,K,j)$], the integration in each composition region is used as the penalty term for the ratio of the thermal conductivity and specific heat.

$$\int\int\int \left[\eta_{1ij}h_2^2 + \eta_{2ij}\left\{\left(\frac{\partial}{\partial x}h_2\right)^2 + \left(\frac{\partial}{\partial y}h_2\right)^2 + \left(\frac{\partial}{\partial z}h_2\right)^2\right\} + \eta_{3ij}\left\{\frac{\partial^2}{\partial x^2}h_2 + \frac{\partial^2}{\partial y^2}h_2 + \frac{\partial^2}{\partial z^2}h_2\right\}^2\right]dV \quad (115)$$

Here, $h_2$ is the ratio of the thermal conductivity and specific heat at each point, i.e., $h_{2i}(x,y,z,t)$, $h_{2i}(x,y,z)$, $h_2(x,y,z)$, $h_2(x,y,z,t)$. The same as in the case when the 3D ROI includes the 2D or 1D composition region. The same as in the case when the ROI is 2D or 1D.

When the functionals II(U') or II(V') [eqs. (89) to (97)] are finite-element-approximated, the respective penalty terms (107) to (115) are finite-element-approximated using the same basis functions as those used for the finite-element approximating eqs. (89) to (97). Otherwise, the respective penalty terms (107) to (115) are finite-difference-approximated. When the functionals II(U') or II(V') [eqs. (89) to (97)] are finite-difference-approximated, the respective penalty terms (107) to (115) are finite-difference-approximated.

When the penalty terms (107) to (115) are finite-element-approximated, for instance, when the ROI is 3D, the functional II(U') or II(V') [eqs. (89) to (97)] added to the penalty terms is minimized with respect to U' or V' after the reference conductivities (distributions) k'i(I,J,K,j), k'i(I,J,K), k'(I,J,K), k'(I,J,K,j) are substituted into eqs. (107) to (109), the reference products (distributions) of the density and specific heat ρci(I,J,K,j), ρci(I,J,K), ρc(I,J,K), ρc(I,J,K,j) into eq. (110), the reference densities (distributions), the reference densities (distributions) ρi(I,J,K,j), ρi(I,J,K), ρ(I,J,K), ρ(I,J,K,j) are substituted into eq. (111), the reference specific heats (distributions) ci(I,J,K,j), ci(I,J,K), c(I,J,K), c(I,J,K,j) are substituted into eq. (112), the reference thermal diffusivities (distributions) h'$_0$i(I,J,K,j), h'$_0$i(I,J,K), h'$_0$(I,J,K), h'$_0$(I,J,K,j) are substituted into eq. (113), the reference ratios (distributions) of the thermal conductivity and density h'$_1$i(I,J,K,j), h'$_1$i(I,J,K), h'$_1$(I,J,K), h'$_1$(I,J,K,j) are substituted into eq. (114), the reference ratios (distributions) of thermal conductivity and specific heat h'$_2$i(I,J,K,j), h'$_2$i(I,J,K), h'$_2$(I,J,K), h'$_2$(I,J,K,j) are substituted into (115). The same as in the case when the ROI is 2D or 1D.

When the penalty terms (107) to (115) are finite-difference-approximated, for instance, when the ROI is 3D, the functional II(U') or II(V') [eqs. (89) to (97)] added to the penalty terms is minimized with respect to U' or V' after the reference conductivities (distributions) k'i(I,J,K,j), k'i(I,J,K), k'(I,J,K), k'(I,J,K,j) are substituted into eqs. (107) to (109) [where $\alpha_{1ij}=0$], the reference products (distributions) of the density and specific heat $\rho c i(I,J,K,j)$, $\rho c i(I,J,K)$, $\rho c(I,J,K)$, $\rho c(I,J,K,j)$ into eq. (110) [where $\beta_{1ij}=0$], the reference densities (distributions), the reference densities (distributions) $\rho i(I,J,K,j)$, $\rho i(I,J,K)$, $\rho(I,J,K)$, $\rho(I,J,K,j)$ are substituted into eq. (111) [where $\chi_{1ij}=0$], the reference specific heats (distributions) $c i(I,J,K,j)$, $c i(I,J,K)$, $c(I,J,K)$, $c(I,J,K,j)$ are substituted into eq. (112) [where $\delta_{1ij}=0$], the reference thermal diffusivities (distributions) $h'_0 i(I,J,K,j)$, $h'_0 i(I,J,K)$, $h'_0(I,J,K)$, $h'_0(I,J,K,j)$ are substituted into eq. (113) [$\epsilon_{1ij}=0$], the reference ratios (distributions) of the thermal conductivity and density $h'_1 i(I,J,K,j)$, $h'_1 i(I,J,K)$, $h'_1(I,J,K)$, $h'_1(I,J,K,j)$ are substituted into eq. (114) [$\gamma_{1ij}=0$], the reference ratios (distributions) of thermal conductivity and specific heat $h'_2 i(I,J,K,j)$, $h'_2 i(I,J,K)$, $h'_2(I,J,K)$, $h'_2(I,J,K,j)$ are substituted into (115) [$\eta_{1ij}=0$]. The same as in the case when the ROI is 2D or 1D.

By solving the regularized normal equations (116) to (124) for the unknown nodal distribution U' or V' derived from the respective functionals II(U') or II(V'), the unknown nodal distribution Uij, Ui, Uj, U, Vij, Vi, Vj or V is stably obtained. Here, respective $G^T G$ and $G^T G G^T G$ in the regularized normal equations are the Laplacian and squared Laplacian operators (applied to the unknown nodal distribution Uij, Ui, Uj, U, Vij, Vi, Vj or Q' in V in the ROI) approximated by the finite element or finite difference (discrete). Here, the unknown nodal distribution Q' can include the unknown thermal conductivity distribution, L'ij, L'i, L' or L'j, the unknown product distribution of the density and specific heat, R'ij, R'I, R' or R'j, the unknown density or specific heat distribution, S'ij, S'i, S' or S'j, the unknown thermal diffusivity distribution $H_0'ij$, $H_0'i$, $H_0'$ or $H_0'j$, the unknown ratio of the thermal conductivity and density $H_1'ij$, $H_1'i$, $H_1'$ or $H_1'j$, or the unknown ratio of the thermal conductivity and specific heat $H_2'ij$, $H_2'i$, $H_2'$ or $H_2'j$.

Therefore, the respective regularization parameters $\lambda_{1ij}$, $\lambda_{2ij}$, $\lambda_{3ij}$ in equations are expressed such that the respective regularization parameters of the used penalty terms (107) to (115) are multiplied to the corresponding penalty terms, i.e., $\alpha_{1ij}$, $\alpha_{2ij}$, $\alpha_{3ij}$, $\beta_{1ij}$, $\beta_{2ij}$, $\beta_{3ij}$, $\chi_{1ij}$, $\chi_{2ij}$, $\chi_{3ij}$, $\delta_{1ij}$, $\delta_{2ij}$, $\delta_{3ij}$, $\epsilon_{1ij}$, $\epsilon_{2ij}$, $\epsilon_{3ij}$, $\gamma_{1ij}$, $\gamma_{2ij}$, $\gamma_{3ij}$, $\eta_{1ij}$, $\eta_{2ij}$, $\eta_{3ij}$ (positive values).

From the functional IIij(Uij) [eq. (89)], the following regularized normal equations are derived for the unknown nodal distribution Uij (i=1~M, j=0~n). Here, the unknown nodal distribution Uij can be invariant with respect to either i or j, or both i and j. Occasionally, the equations can also be used when only one set of the temperature data $DTi/dt$, Ti, Di, $\nabla Di$ is measured.

$$(E'_{ij}+W_{ij})U_{ij}=e'_{ij} \quad (116)$$

Here, the matrix E'ij and the vector e'ij are respectively the matrix $E'_{ij}=E_{ij}^T E_{ij}$ and the vector $e'_{ij}=E_{ij}^T e_{ij}$ in the normal equations (98), and the matrix $W_{ij}=\lambda_{1ij}I+\lambda_{2ij}G^T G+\lambda_{3ij}G^T G G^T G$.

From the functional IIj(Uij) [eq. (90)], the following regularized normal equations are derived for the unknown nodal distribution Uij (i=1~M, j=0~n). Here, Uij can be invariant with respect to j.

$$\begin{bmatrix} E'_{1j}+W_{1j} & & & 0 \\ & E'_{2j}+W_{2j} & & \\ & & \ddots & \\ 0 & & & E'_{Mj}+W_{Mj} \end{bmatrix} \begin{bmatrix} U_{1j} \\ U_{2j} \\ \vdots \\ U_{Mj} \end{bmatrix} = \begin{bmatrix} e'_{1j} \\ e'_{2j} \\ \vdots \\ e'_{Mj} \end{bmatrix} \quad (117)$$

Here, the matrix E'ij and the vector e'ij (i=1~M, j=0~n) are respectively those in the normal equations (98), and the matrix $W_{ij}=\lambda_{1ij}I+\lambda_{2ij}G^T G+\lambda_{3ij}G^T G G^T G$.

From the functional IIj(Uj) [eq. (91)], the following regularized normal equations are derived for the unknown nodal distribution Uj (j=0~n). Here, Uj can be invariant with respect to j.

$$(E_j+W_j)U_j=e_j \quad (118)$$

Here, the matrix Ej and the vector ej (j=0~n) are respectively $\Sigma_{i=1}^M E'_{ij}$ and $\Sigma_{i=1}^M e'_{ij}$ using the matrix E'ij and the vector e'ij in the normal equations (98), and the matrix $W_j=\lambda_{1j}I+\lambda_{2j}G^T G+\lambda_{3j}G^T G G^T G$, where $\lambda_{1j}=\Sigma_{i=1}^M \lambda_{1ij}$, $\lambda_{2j}=\Sigma_{i=1}^M \lambda_{2ij}$, $\lambda_{3j}=\Sigma_{i=1}^M \lambda_{3ij}$.

From the functional IIi(Uij) [eq. (92)], the following regularized normal equations are derived for the unknown nodal distribution Uij (i=1~M, j=0~n). Here, Uij can be invariant with respect to i.

$$\begin{bmatrix} E'_{i0}+W_{i0} & & & 0 \\ & E'_{i1}+W_{i1} & & \\ & & \ddots & \\ 0 & & & E'_{in}+W_{in} \end{bmatrix} \begin{bmatrix} U_{i0} \\ U_{i1} \\ \vdots \\ U_{in} \end{bmatrix} = \begin{bmatrix} e'_{i0} \\ e'_{i1} \\ \vdots \\ e'_{in} \end{bmatrix} \quad (119)$$

Here, the matrix E'ij and the vector e'ij (i=1~M, j=0~n) are respectively those of the normal equations (98), and the matrix $W_{ij}=\lambda_{1ij}I+\lambda_{2ij}G^T G+\lambda_{3ij}G^T G G^T G$.

From the functional IIi(Ui) [eq. (93)], the following regularized normal equations are derived for the unknown nodal distribution Ui (i=1~M). Here, Ui can be invariant with respect to i.

$$(E_i+W_i)U_i=e_i \quad (120)$$

Here, the matrix Ei and the vector ei (i=1~M) are respectively $\Sigma_{j=0}^n E'_{ij}$ and $\Sigma_{j=0}^n e'_{ij}$ using the matrix E'ij and the vector e'ij in the normal equations (98), and the matrix $W_i=\lambda_{1i}I+\lambda_{2i}G^T G+\lambda_{3i}G^T G G^T G$, where $\lambda_{1i}=\Sigma_{j=0}^n \lambda_{1ij}$, $\lambda_{2i}=\Sigma_{j=0}^n \lambda_{2ij}$, $\lambda_{3i}=\Sigma_{j=0}^n \lambda_{3ij}$.

From the functional II(Uij) [eq. (94)], the following regularized normal equations are derived for the unknown nodal distribution Uij (i=1~M, j=0~n).

$$\begin{bmatrix} E'_{10}+W_{10} & & & & & & & & & \\ & E'_{11}+W_{11} & & & & & & & & \\ & & \ddots & & & & & & & \\ & & & E'_{1n}+W_{1n} & & & & & & \\ & & & & E'_{20}+W_{20} & & & & & \\ & & & & & E'_{21}+W_{21} & & & 0 & \\ & & & & & & \ddots & & & \\ & & & & & & & E'_{2n}+W_{2n} & & \\ & & & & & & & & \ddots & \\ & & & & & & & & & E'_{M0}+W_{M0} & \\ & & 0 & & & & & & & & E'_{M1}+W_{M1} \\ & & & & & & & & & & & \ddots \\ & & & & & & & & & & & & E'_{Mn}+W_{Mn} \end{bmatrix} \quad (121)$$

$$\begin{bmatrix} U_{10} \\ U_{11} \\ \vdots \\ U_{1n} \\ U_{20} \\ U_{21} \\ \vdots \\ U_{2n} \\ \vdots \\ U_{M0} \\ U_{M1} \\ \vdots \\ U_{Mn} \end{bmatrix} = \begin{bmatrix} e'_{10} \\ e'_{11} \\ \vdots \\ e'_{1n} \\ e'_{20} \\ e'_{21} \\ \vdots \\ e'_{2n} \\ \vdots \\ e'_{M0} \\ e'_{M1} \\ \vdots \\ e'_{Mn} \end{bmatrix}$$

Here, the matrix E'ij and the vector e'ij (i=1~M, j=0~n) are respectively those of the normal equations (98), and the matrix $W_{ij}=\lambda_{1ij}+\lambda_{2ij}G^TG+\lambda_{3ij}G^TGG^TG$.

From the functional II(Uj) [eq. (95)], the following regularized normal equations are derived for the unknown nodal distribution Uj (j=0~n).

$$\begin{bmatrix} E_0+W_0 & & & \\ & E_1+W_1 & & 0 \\ & & \ddots & \\ & 0 & & E_n+W_n \end{bmatrix} \begin{bmatrix} U_0 \\ U_1 \\ \vdots \\ U_n \end{bmatrix} = \begin{bmatrix} e_0 \\ e_1 \\ \vdots \\ e_n \end{bmatrix} \quad (122)$$

Here, the matrix Ej and the vector ej (j=0~n) are respectively $\Sigma_{i=1}^{M} E'_{ij}$ and $\Sigma_{i=1}^{M} e'_{ij}$ using the matrix E'ij and the vector e'ij in the normal equations (98), and the matrix $W_j=\lambda_{1j}I+\lambda_{2j}G^TG+\lambda_{3j}G^TGG^TG$, where $\lambda_{1j}=\Sigma_{i=1}^{M}\lambda_{1ij}$, $\lambda_{2j}=\Sigma_{i=1}^{M}\lambda_{2ij}$, $\lambda_{3j}=\Sigma_{i=1}^{M}\lambda_{3ij}$.

From the functional II(Ui) [eq. (96)], the following regularized normal equations are derived for the unknown nodal distribution Ui (i=1~M).

$$\begin{bmatrix} E_1+W_1 & & & \\ & E_2+W_2 & & 0 \\ & & \ddots & \\ & 0 & & E_M+W_M \end{bmatrix} \begin{bmatrix} U_1 \\ U_2 \\ \vdots \\ U_M \end{bmatrix} = \begin{bmatrix} e_1 \\ e_2 \\ \vdots \\ e_M \end{bmatrix} \quad (123)$$

Here, the matrix Ei and the vector ei (i=1~M) are respectively $\Sigma_{j=0}^{n} E'_{ij}$ and $\Sigma_{j=0}^{n} e'_{ij}$ using the matrix E'ij and the vector e'ij of the normal equations (98), the matrix $W_i=\lambda_{1i}I+\lambda_{2i}G^TG+\lambda_{3i}G^TGG^TG$, where $\lambda_{1i}=\Sigma_{j=0}^{n}\lambda_{1ij}$, $\lambda_{2i}=\Sigma_{j=0}^{n}\lambda_{2ij}$, $\lambda_{3i}=\Sigma_{j=0}^{n}\lambda_{3ij}$.

From the functional II(U) [eq. (97)], the following regularized normal equations are derived for the unknown nodal distribution U.

$$(E+W)U=e \quad (124)$$

Here, the matrix E and the vector e are respectively $\Sigma_{i=1}^{M}\Sigma_{j=0}^{n} E'_{ij}$ and $\Sigma_{i=1}^{M}\Sigma_{j=0}^{n} e'_{ij}$ using the matrix E'ij and the vector e'ij of the normal equations (98), $W=\lambda_1 I+\lambda_2 G^TG+\lambda_3 G^TGG^TG$, where $\lambda_1=\Sigma_{i=1}^{M}\Sigma_{j=0}^{n}\lambda_{1ij}$, $\lambda_2=\Sigma_{i=1}^{M}\Sigma_{j=0}^{n}\lambda_{2ij}$, $\lambda_3=\Sigma_{i=1}^{M}\Sigma_{j=0}^{n}\lambda_{3ij}$.

By solving the above-described normal equations (116) to (124) for the unknown nodal vector U', the unknown nodal distribution Uij, Ui, U or Uj can be estimated for over the ROI. Alternatively, the unknown nodal distribution V can also be estimated for the composition regions, i.e., Vij, Vi, V or Vj.

Thus, the unknown, thermal conductivity distribution Lij [ki(x,y,z,t)] when the ROI is 3D], Li [ki(x,y,z)], L [k(x,y,z)], Lj [k(x,y,z,t)], product distribution of the density and specific heat Rij [ρci(x,y,z,t)], Ri [ρci(x,y,z)], R [ρc(x,y,z)], Rj [ρc(x,y,z,t)], specific heat distribution Sij [ci(x,y,z,t)], Si [ci(x,y,z)], S [c(x,y,z)], Sj [c(x,y,z,t)], density distribution Sij [ρi(x,y,z,t)], Si [ρi(x,y,z)], S [ρ(x,y,z)], Sj [ρ(x,y,z,t)], thermal diffusivity distribution $H_0$ij [$h_{0i}$(x,y,z,t)], $H_0$i [$h_{0i}$(x,y,z)], $H_0$ [$h_0$(x,y,z)], $H_{0j}$ [$h_0$(x,y,z,t)], ratio distribution of the thermal conductivity and density $H_1$ij [$h_{1i}$(x,y,z,t)], $H_1$i [$h_{1i}$(x,y,z)], $H_1$ [$h_1$(x,y,z)], $H_{1j}$ [$h_1$(x,y,z,t)], ratio distribution of the thermal conductivity and specific heat $H_2$ij [$h_{2i}$(x,y,z,t)], $H_2$i [$h_{2i}$(x,y,z)], $H_2$ [$h_2$(x,y,z)], $H_{2j}$ [$h_2$(x,y,z,t)] can be estimated. When using the finite element approximations, the above-described basis functions are used. As in the case when the ROI is 2D or 1D. Occasionally, when only one set of the temperature data dTi/dt, Ti, Di, ∇Di is measured, these can also be estimated.

When regularizing the functionals II(U') or II(V') [eqs. (92), (94) and (95)] with respect to the unknown nodal vector U' (i.e., Uij or Uj) or V' (i.e., Vij or Vj) being dependent of j, in addition to the penalty terms (107) to (115), the penalty terms (107) to (115) of which integral kernels are added to the temporal first and second partial derivatives with respect to t(j) of the unknown distributions in the respective composition regions, expressed in the continuous coordinate system, can be used to stabilize the reconstruction. The new regularization parameters used together with the penalty terms are set for the respective temperature distributions Tij as described bellows, i.e., $\alpha_{4ij}$, $\alpha_{5ij}$, $\beta_{4ij}$, $\beta_{5ij}$, $\chi_{4ij}$, $\chi_{5ij}$, $\delta_{4ij}$, $\delta_{5ij}$, $\epsilon_{4ij}$, $\epsilon_{5ij}$, $\gamma_{4ij}$, $\gamma_{5ij}$, $\eta_{4ij}$, $\eta_{5ij}$ (positive values)

That is, when the unknown nodal vector U' or V' includes the unknown thermal conductivity distribution L'ij or L'j, for instance, when the ROI is 3D and the ROI includes at least one composition region of the unknown thermal conductivity distribution $k_i$(x,y,z,t) [$k_i$(I,J,K,j)], k(x,y,z,t) [k(I,J,K,j)], the integral kernel of the penalty term (107) can be added to the temporal first and second derivatives with respect to t(j) of the thermal conductivity distribution.

$$\int\int\int \left[\alpha_{1ij}k^2 + \alpha_{2ij}\left\{\left(\frac{\partial}{\partial x}k\right)^2\left(\frac{\partial}{\partial y}k\right)^2 + \left(\frac{\partial}{\partial z}k\right)^2\right\} + \alpha_{3ij}\left\{\frac{\partial^2}{\partial x^2}k + \frac{\partial^2}{\partial y^2}k + \frac{\partial^2}{\partial z^2}k\right\}^2 + \alpha_{4ij}\left(\frac{\partial}{\partial t}k\right)^2 \alpha_{5ij}\left(\frac{\partial^2}{\partial t^2}k\right)^2\right]dV \quad (125)$$

Here, k is the thermal conductivity at each point, i.e., $k_i$(x,y,z,t) or k(x,y,z,t).

When the ROI is 2D and the ROI includes at least one composition region of the unknown thermal conductivity distribution $k_i$(x,y,t) [$k_i$(I,J,j)], k(x,y,t) [k(I,J,j)], the integral kernel of the penalty term (108) can be added to the temporal first and second derivatives with respect to t(j) of the thermal conductivity distribution.

$$\int\int \left[\alpha_{ij}k^2 + \alpha_{2ij}\left\{\left(\frac{\partial}{\partial x}k\right)^2 + \left(\frac{\partial}{\partial y}k\right)^2\right\} + \alpha_{3ij}\left\{\frac{\partial^2}{\partial x^2}k + \frac{\partial^2}{\partial y^2}k\right\}^2 + \alpha_{4ij}\left(\frac{\partial}{\partial t}k\right)^2 + \alpha_{5ij}\left(\frac{\partial^2}{\partial t^2}k\right)^2\right]dA \quad (126)$$

Here, k is the thermal conductivity at each point, i.e., $k_i$(x,y,t) or k(x,y,t).

When the ROI is 2D and the ROI includes at least one composition region of the unknown thermal conductivity distribution $k_i$(x,t) [$k_i$(I,j)], k(x,t) [k(I,j)], the integral kernel of the penalty term (109) can be added to the temporal first and second derivatives with respect to t(j) of the thermal conductivity distribution.

$$\int \left[\alpha_{1ij}k^2 + \alpha_{2ij}\left\{\frac{\partial}{\partial x}k\right\}^2 + \alpha_{3ij}\left\{\frac{\partial^2}{\partial x^2}k\right\}^2 + \alpha_{4ij}\left(\frac{\partial}{\partial t}k\right)^2 + \alpha_{5ij}\left(\frac{\partial^2}{\partial t^2}k\right)^2\right]dx \quad (127)$$

Here, k is the thermal conductivity at each point, i.e., $k_i$(x,y,t) or k(x,y,t). As in the case when the ROI is 2D or 1D.

Otherwise, when the unknown nodal vector U' or V' includes the unknown product distribution of the density and specific heat R'ij or R'j, for instance, when the ROI is 3D and the ROI includes at least one composition region of the unknown product distribution of the density and specific heat $\rho c_i$(x,y,z,t) [$\rho c_i$(I,J,K,j)], ρc(x,y,z,t) [ρc(I,J,K,j)], the integral kernel of the penalty term (110) can be added to the temporal first and second derivatives with respect to t(j) of the product distribution of the density and specific heat.

$$\int\int\int \left[\beta_{1ij}(\rho c)^2 + \beta_{2ij}\left\{\left(\frac{\partial}{\partial x}(\rho c)\right)^2 + \left(\frac{\partial}{\partial y}(\rho c)\right)^2 + \left(\frac{\partial}{\partial z}(\rho c)\right)^2\right\} + \beta_{3ij}\left\{\frac{\partial^2}{\partial x^2}(\rho c) + \frac{\partial^2}{\partial y^2}(\rho c) + \frac{\partial^2}{\partial z^2}(\rho c)\right\}^2 + \beta_{4ij}\left(\frac{\partial}{\partial t}(\rho c)\right)^2 + \beta_{5ij}\left(\frac{\partial^2}{\partial t^2}(\rho c)\right)^2\right]dV \quad (128)$$

Here, ρc is the product of the density and specific heat at each point, i.e., $\rho c_i$(x,y,z,t), ρc(x,y,z,t). The same as in the case when the 3D ROI includes the 2D or 1D composition region. The same as in the case when the ROI is 2D or 1D.

Otherwise, when the unknown nodal vector U' or V' includes the unknown density distribution S'ij or S'j, for instance, when the ROI is 3D and the ROI includes at least one composition region of the unknown density distribution $\rho_i$(x,y,z,t) [$\rho_i$(I,J,K,j)], ρ(x,y,z,t) [ρ(I,J,K,j)], the integral kernel of the penalty term (111) can be added to the temporal first and second derivatives with respect to t(j) of the density distribution.

$$\int\int\int\left[\chi_{1ij}\rho^2+\chi_{2ij}\left\{\left(\frac{\partial}{\partial x}\rho\right)^2+\left(\frac{\partial}{\partial y}\rho\right)^2+\left(\frac{\partial}{\partial z}\rho\right)^2\right\}+\right.\quad(129)$$
$$\chi_{3ij}\left\{\frac{\partial^2}{\partial x^2}\rho+\frac{\partial^2}{\partial y^2}\rho+\frac{\partial^2}{\partial z^2}\rho\right\}^2+$$
$$\left.\chi_{4ij}\left(\frac{\partial}{\partial t}\rho\right)^2+\chi_{5ij}\left(\frac{\partial^2}{\partial t^2}\rho\right)^2\right]dV$$

Here, $\rho$ is the density at each point, i.e., $\rho_i(x,y,z,t)$, $\rho(x,y,z,t)$. The same as in the case when the 3D ROI includes the 2D or 1D composition region. The same as in the case when the ROI is 2D or 1D.

Otherwise, when the unknown nodal vector U' or V' includes the unknown specific heat distribution S'ij or S'j, for instance, when the ROI is 3D and the ROI includes at least one composition region of the unknown specific heat distribution $c_i(x,y,z,t)$ [$c_i(I,J,K,j)$], $c(x,y,z,t)$ [$c(I,J,K,j)$], the integral kernel of the penalty term (112) can be added to the temporal first and second derivatives with respect to t(j) of the specific heat distribution.

$$\int\int\int\left[\delta_{1ij}c^2+\delta_{2ij}\left\{\left(\frac{\partial}{\partial x}c\right)^2+\left(\frac{\partial}{\partial y}c\right)^2+\left(\frac{\partial}{\partial z}c\right)^2\right\}+\delta_{3ij}\right.\quad(130)$$
$$\left.\left\{\frac{\partial^2}{\partial x^2}c+\frac{\partial^2}{\partial y^2}c+\frac{\partial^2}{\partial z^2}c\right\}^2+\delta_{4ij}\left(\frac{\partial}{\partial t}c\right)^2+\delta_{5ij}\left(\frac{\partial^2}{\partial t^2}c\right)^2\right]dV$$

Here, c is the specific heat at each point, i.e., $c_i(x,y,z,t)$, $c(x,y,z,t)$. The same as in the case when the 3D ROI includes the 2D or 1D composition region. The same as in the case when the ROI is 2D or 1D.

Otherwise, when the unknown nodal vector U' or V' includes the unknown thermal diffusivity distribution $H_0'_{ij}$, $H_0'_j$, for instance, when the ROI is 3D and the ROI includes at least one composition region of the unknown thermal diffusivity distribution $h_{0i}(x,y,z,t)$ [$h_{0i}(I,J,K,j)$], $h_0(x,y,z,t)$ [$h_0(I,J,K,j)$], the integral kernel of the penalty term (113) can be added to the temporal first and second derivatives with respect to t(j) of the thermal diffusivity distribution.

$$\int\int\int\left[\varepsilon_{1ij}h_0^2+\varepsilon_{2ij}\left\{\left(\frac{\partial}{\partial x}h_0\right)^2+\left(\frac{\partial}{\partial y}h_0\right)^2+\left(\frac{\partial}{\partial z}h_0\right)^2\right\}+\right.\quad(131)$$
$$\varepsilon_{3ij}\left\{\frac{\partial^2}{\partial x^2}h_0+\frac{\partial^2}{\partial y^2}h_0+\frac{\partial^2}{\partial z^2}h_0\right\}^2+$$
$$\left.\varepsilon_{4ij}\left(\frac{\partial}{\partial t}h_0\right)^2+\varepsilon_{5ij}\left(\frac{\partial^2}{\partial t^2}h_0\right)^2\right]dV$$

Here, $h_0$ is the thermal diffusivity at each point, i.e., $h_{0i}(x,y,z,t)$, $h_0(x,y,z,t)$. The same as in the case when the 3D ROI includes the 2D or 1D composition region. The same as in the case when the ROI is 2D or 1D.

Otherwise, when the unknown nodal vector U' or V' includes the unknown ratio distribution of the thermal conductivity and density $H_1'_{ij}$, $H_1'_j$, for instance, when the ROI is 3D and the ROI includes at least one composition region of the unknown ratio distribution of the thermal conductivity and density $h_{1i}(x,y,z,t)$ [$h_{1i}(I,J,K,j)$], $h_1(x,y,z,t)$ [$h_1(I,J,K,j)$], the integral kernel of the penalty term (114) can be added to the temporal first and second derivatives with respect to t(j) of the ratio distribution of the thermal conductivity and density.

$$\int\int\int\left[\gamma_{1ij}h_1^2+\gamma_{2ij}\left\{\left(\frac{\partial}{\partial x}h_1\right)^2+\left(\frac{\partial}{\partial y}h_1\right)^2+\left(\frac{\partial}{\partial z}h_1\right)^2\right\}+\right.\quad(132)$$
$$\gamma_{3ij}\left\{\frac{\partial^2}{\partial x^2}h_1+\frac{\partial^2}{\partial y^2}h_1+\frac{\partial^2}{\partial z^2}h_1\right\}^2+$$
$$\left.\gamma_{4ij}\left(\frac{\partial}{\partial t}h_1\right)^2+\gamma_{5ij}\left(\frac{\partial^2}{\partial t^2}h_1\right)^2\right]dV$$

Here, $h_1$ is the ratio of the thermal conductivity and density at each point, i.e., $h_{1i}(x,y,z,t)$, $h_1(x,y,z,t)$. The same as in the case when the 3D ROI includes the 2D or 1D composition region. The same as in the case when the ROI is 2D or 1D.

Otherwise, when the unknown nodal vector U' or V' includes the unknown ratio distribution of the thermal conductivity and specific heat $H_2'_{ij}$, $H_2'_j$, for instance, when the ROI is 3D and the ROI includes at least one composition region of the unknown ratio distribution of the thermal conductivity and specific heat $h_{1i}(x,y,z,t)$ [$h_{1i}(I,J,K,j)$], $h_1(x,y,z,t)$ [$h_1(I,J,K,j)$], the integral kernel of the penalty term (115) can be added to the temporal first and second derivatives with respect to t(j) of the ratio distribution of the thermal conductivity and specific heat.

$$\int\int\int\left[\eta_{1ij}h_2^2+\eta_{2ij}\left\{\left(\frac{\partial}{\partial x}h_2\right)^2+\left(\frac{\partial}{\partial y}h_2\right)^2+\left(\frac{\partial}{\partial z}h_2\right)^2\right\}+\right.\quad(133)$$
$$\eta_{3ij}\left\{\frac{\partial^2}{\partial x^2}h_2+\frac{\partial^2}{\partial y^2}h_2+\frac{\partial^2}{\partial z^2}h_2\right\}^2+$$
$$\left.\eta_{4ij}\left(\frac{\partial}{\partial t}h_2\right)^2+\eta_{5ij}\left(\frac{\partial^2}{\partial t^2}h_2\right)^2\right]dV$$

Here, $h_2$ is the ratio of the thermal conductivity and specific heat at each point, i.e., $h_{2i}(x,y,z,t)$, $h_2(x,y,z,t)$. The same as in the case when the 3D ROI includes the 2D or 1D composition region. The same as in the case when the ROI is 2D or 1D.

When the functionals II(U') or II(V') [eqs. (92), (94) and (95)] are finite-element-approximated, the respective penalty terms (125) to (133) are finite-element-approximated using the same basis functions as those used for the finite-element approximating eqs. (92), (94) and (95). Otherwise, the respective penalty terms (125) to (133) are finite-difference-approximated. When the functionals II(U') or II(V') [eqs. (92), (94) and (95)] are finite-difference-approximated, the respective penalty terms (125) to (133) are finite-difference-approximated.

When the penalty terms (125) to (133) are finite-element-approximated, for instance, when the ROI is 3D, the functional II(U') or II(V') [eqs. (92), (94) and (95)] added to the penalty terms is minimized with respect to U' or V' after the reference conductivities (distributions) k'i(I,J,K,j), k'i(I,J,K), k'(I,J,K), k'(I,J,K,j) are substituted into eqs. (125) to (127), the reference products (distributions) of the density and specific heat $\rho ci(I,J,K,j)$, $\rho ci(I,J,K)$, $\rho c(I,J,K)$, $\rho c(I,J,K,j)$ into eq. (128), the reference densities (distributions), the reference densities (distributions) $\rho i(I,J,K,j)$, $\rho i(I,J,K)$, $\rho(I,J,K)$, $\rho(I,J,K,j)$ are substituted into eq. (129), the reference specific heats (distributions) $ci(I,J,K,j)$, $ci(I,J,K)$, $c(I,J,K)$, $c(I,J,K,j)$ are substituted into eq. (130), the reference thermal diffusivities (distributions) $h'_0i(I,J,K,j)$, $h'_0i(I,J,K)$, $h'_0(I,J,K)$, $h'_0(I,J,K,j)$ are substituted in to eq. (131), the reference ratios (distributions) of the thermal conductivity and density $h'_1i(I,J,K,j)$, $h'_1i(I,J,K)$, $h'_1(I,J,K)$, $h'_1(I,J,K,j)$ are substituted into eq. (132), the reference ratios (distributions) of thermal conductivity and specific heat $h'_2i(I,J,K,j)$, $h'_2i(I,J,K)$, $h'_2(I,J,K)$, $h'_2(I,J,K,j)$ are substituted into (133) The same as in the case when the ROI is 2D or 1D.

Here, the unknown nodal vector U' is the unknown nodal distribution Uij or Uj, and the unknown nodal vector V' is the unknown nodal distribution Vij or Vj.

When the penalty terms (125) to (133) are finite-difference-approximated, for instance, when the ROI is 3D, the functional II(U') or II(V') [eqs. (92), (94) and (95)] added to the penalty terms is minimized with respect to U' or V' after the reference conductivities (distributions) k'i(I,J,K,j), k'i(I,J,K), k'(I,J,K), k'(I,J,K,j) are substituted into eqs. (125) to (127) [where $\alpha_{1ij}=0$], the reference products (distributions) of the density and specific heat $\rho ci(I,J,K,j)$, $\rho ci(I,J,K)$, $\rho c(I,J,K)$, $\rho c(I,J,K,j)$ into eq. (128) [where $\beta_{1ij}=0$], the reference densities (distributions), the reference densities (distributions) $\rho i(I,J,K,j)$, $\rho i(I,J,K)$, $\rho(I,J,K)$, $\rho(I,J,K,j)$ are substituted into eq. (129) [where $\chi_{1ij}=0$], the reference specific heats (distributions) $ci(I,J,K,j)$, $ci(I,J,K)$, $c(I,J,K)$, $c(I,J,K,j)$ are substituted into eq. (130) [where $\delta_{1ij}=0$], the reference thermal diffusivities (distributions) $h'_0i(I,J,K,j)$, $h'_0i(I,J,K)$, $h'_0(I,J,K)$, $h'_0(I,J,K,j)$ are substituted into eq. (131) [$\epsilon_{1ij}=0$], the reference ratios (distributions) of the thermal conductivity and density $h'_1i(I,J,K,j)$, $h'_1i(I,J,K)$, $h'_1(I,J,K)$, $h'_1(I,J,K,j)$ are substituted into eq. (132) [$\gamma_{1ij}=0$], the reference ratios (distributions) of thermal conductivity and specific heat $h'_2i(I,J,K,j)$, $h'_2i(I,J,K)$, $h'_2(I,J,K)$, $h'_2(I,J,K,j)$ are substituted into (133) [$\eta_{1ij}=0$]. The same as in the case when; the ROI is 2D or 1D.

By solving the regularized normal equations (134) to (136) for the unknown nodal distribution U' or V' derived from the respective functionals II(U') or II(V'), the unknown nodal distribution Uij, Uj, Vij or Vj is stably obtained. Here, the respective regularization parameters $\lambda_{1ij}$, $\lambda_{2ij}$, $\lambda_{3ij}$, $\lambda_{4ij}$ and $\lambda_{5ij}$ in equations are expressed such that the respective regularization parameters of the used penalty terms (125) to (133) are multiplied to the corresponding penalty terms, i.e., $\alpha_{1ij}$, $\alpha_{2ij}$, $\alpha_{3ij}$, $\alpha_{4ij}$, $\alpha_{5ij}$, $\beta_{1ij}$, $\beta_{2ij}$, $\beta_{3ij}$, $\beta_{4ij}$, $\beta_{5ij}$, $\chi_{1ij}$, $\chi_{2ij}$, $\chi_{3ij}$, $\chi_{4ij}$, $\chi_{5ij}$, $\delta_{1ij}$, $\delta_{2ij}$, $\delta_{3ij}$, $\delta_{4ij}$, $\delta_{5ij}$, $\epsilon_{1ij}$, $\epsilon_{2ij}$, $\epsilon_{3ij}$, $\epsilon_{4ij}$, $\epsilon_{5ij}$, $\gamma_{1ij}$, $\gamma_{2ij}$, $\gamma_{3ij}$, $\gamma_{4ij}$, $\gamma_{5ij}$, $\eta_{1ij}$, $\eta_{2ij}$, $\eta_{3ij}$, $\eta_{4ij}$, $\eta_{5ij}$ (positive values).

That is, the unknown sequence of the nodal distributions $(U_{i0}, U_{i1}, \ldots, U_{in})$ for over the ROI or $(V_{i0}, V_{i1}, \ldots, V_{in})$ for the composition region can be stably estimated [i=1~M] by solving the following regularized normal equations for the unknown nodal vector $X_{ij}=(U_{i0}{}^T, U_{i1}{}^T, \ldots, U_{in}{}^T)^T$ or $X_{ij}=(V_{i0}{}^T, V_{i1}{}^T, \ldots, V_{in}{}^T)^T$ derived from the functional $II_t(X_{ij})$ [eq. (92)].

$$\left[\begin{array}{cccc} E'_{i0}+W_{i0} & & & 0 \\ & E'_{i1}+W_{i1} & & \\ & & \ddots & \\ 0 & & & E'_{in}+W_{in} \end{array}\right] + \left[\begin{array}{cccc} \lambda_{4i0} & & & 0 \\ & \lambda_{4i1} & & \\ & & \ddots & \\ 0 & & & \lambda_{4in} \end{array}\right] \quad (134)$$

$$\left\{G_t^T G_t + \left[\begin{array}{cccc} \lambda_{5i0} & & & 0 \\ & \lambda_{5i1} & & \\ & & \ddots & \\ 0 & & & \lambda_{5in} \end{array}\right] G_t^T G_t G_t^T G_t\right\} \left[\begin{array}{c} U_{i0} \\ U_{i1} \\ \vdots \\ U_{in} \end{array}\right] = \left[\begin{array}{c} e'_{i0} \\ e'_{i1} \\ \vdots \\ e'_{in} \end{array}\right]$$

Here, the matrix E'ij and the vector e'ij (i=1~M, j=0~n) are respectively those of the normal equations (98), and the matrix $W_{ij}=\lambda_{1ij}I+\lambda_{2ij}G^TG+\lambda_{3ij}G^TGG^TG$.

Here, the matrix $G^TG$, $G^TGG^TG$, $Gt^TGt$, $Gt^TGtGt^TGt$ are respectively the finite-element-approximated or finite-difference (discrete)-approximated, above-described Laplacian and squared Laplacian operators, and temporal first and second order partial derivative operators with respect t(j) multiplied to the unknown nodal distributions Q' included by the unknown nodal distributions $(U_{i0}, U_{i1}, \ldots, U_{in})$ or $(V_{i0}, V_{i1}, \ldots, V_{in})$. Here, the unknown nodal distribution Q' can include the unknown, thermal conductivity nodal distribution $L'_{ij}$, $L_j'$, product nodal distribution of the density and specific heat $R'_{ij}$, $R'_j$, density or specific heat nodal distribution $S'_{ij}$, $S'_j$, thermal diffusivity nodal distribution $H_0'_{ij}$, $H_0'_j$, ratio distribution of the thermal conductivity and density $H_1'_{ij}$, $H_1'_j$, ratio distribution of the thermal conductivity and specific heat $H_2'_{ij}$, $H_2'_j$.

That is, the unknown sequence of the nodal distributions; $(U_{10}, U_{11}, \ldots, U_{1n}, U_{20}, U_{21}, \ldots, U_{2n}, \ldots, U_{M0}, U_{M1}, \ldots, U_{Mn})$ for over the ROI or $(V_{10}, V_{11}, \ldots, V_{1n}, V_{20}, V_{21}, \ldots, V_{2n}, \ldots, V_{M0}, V_{M1}, \ldots, V_{Mn})$ for the composition region can be stably estimated by solving the following regularized normal equations for the unknown nodal vector $X_{ij}=(U_{10}{}^T, U_{11}{}^T, \ldots, U_{1n}{}^T, U_{20}{}^T, U_{21}{}^T, \ldots, U_{2n}{}^T, \ldots, U_{M0}{}^T, U_{M1}{}^T, \ldots, U_{Mn}{}^T)^T$ or $X_{ij}=(V_{10}{}^T, V_{11}{}^T, \ldots, V_{1n}{}^T, V_{20}{}^T, V_{21}{}^T, \ldots, V_{2n}{}^T, \ldots, V_{M0}{}^T, V_{M1}{}^T, \ldots, V_{Mn}{}^T)^T$ derived from the functional $II_t(X_{ij})$ [eq. (94)].

$$\left[\begin{bmatrix} E'_{10}+W_{10} & & & & & & & & & \\ & E'_{11}+W_{11} & & & & & & & & \\ & & \ddots & & & & & & & \\ & & & E'_{1n}+W_{1n} & & & & & & \\ & & & & E'_{20}+W_{20} & & & & 0 & \\ & & & & & E'_{21}+W_{21} & & & & \\ & & & & & & \ddots & & & \\ & & & & & & & E'_{2n}+W_{2n} & & \\ & & & & & & & & \ddots & \\ & & & & & & & & & E'_{M0}+W_{M0} \\ & & 0 & & & & & & & E'_{M1}+W_{M1} \\ & & & & & & & & & \ddots \\ & & & & & & & & & E'_{Mn}+W_{Mn} \end{bmatrix}\right. +$$
(135)

$$\begin{bmatrix} \lambda_{410} & & & & & & & & & \\ & \lambda_{420} & & & & & 0 & & & \\ & & \ddots & & & & & & & \\ & & & \lambda_{41n} & & & & & & \\ & & & & \lambda_{420} & & & & & \\ & & & & & \lambda_{421} & & & & \\ & & & & & & \ddots & & & \\ & & & & & & & \lambda_{42n} & & \\ & & & & & & & & \ddots & \\ & & & & & & & & & \lambda_{4M0} \\ & & 0 & & & & & & & \lambda_{4M1} \\ & & & & & & & & & \ddots \\ & & & & & & & & & \lambda_{4Mn} \end{bmatrix}$$

$$\left. G_t^T G + \begin{bmatrix} \lambda_{510} & & & & & & & & \\ & \lambda_{511} & & & & & 0 & & \\ & & \ddots & & & & & & \\ & & & \lambda_{51n} & & & & & \\ & & & & \lambda_{520} & & & & \\ & & & & & \lambda_{521} & & & \\ & & & & & & \ddots & & \\ & & & & & & & \lambda_{52n} & \\ & & & & & & & & \ddots \\ & & & & & & & & \lambda_{5M1} \\ & & 0 & & & & & & \lambda_{5M2} \\ & & & & & & & & \ddots \\ & & & & & & & & \lambda_{5Mn} \end{bmatrix} G_t^T G_t G_t^T G \right] \begin{bmatrix} U_{10} \\ U_{11} \\ \vdots \\ U_{1n} \\ U_{20} \\ U_{21} \\ \vdots \\ U_{2n} \\ \vdots \\ U_{M0} \\ U_{M1} \\ \vdots \\ U_{Mn} \end{bmatrix} = \begin{bmatrix} e'_{10} \\ e'_{11} \\ \vdots \\ e'_{1n} \\ e'_{20} \\ e'_{21} \\ \vdots \\ e'_{2n} \\ \vdots \\ e'_{M0} \\ e'_{M1} \\ \vdots \\ e'_{Mn} \end{bmatrix}$$

Here, the matrix E'ij and the vector e'ij (i=1~M, j=0~n) are respectively those of the normal equations (98), and the matrix $W_{ij} = \lambda_{1ij} I + \lambda_{2ij} G^T G + \lambda_{3ij} G^T G G^T G$.

Here, the matrix $G^T G$, $G^T G G^T G$, $Gt^T Gt$, $Gt^T Gt Gt^T Gt$ are respectively the finite-element-approximated or finite-difference (discrete)-approximated, above-described Laplacian and squared Laplacian operators, and temporal first and second order partial derivative operators with respect t(j) multiplied to the unknown nodal distributions Q' included by the unknown nodal distributions ($U_{10}$, $U_{11}$, . . . , $U_{1n}$, $U_{20}$, $U_{21}$, . . . , $U_{2n}$, . . . , $U_{M0}$, $U_{M1}$, . . . , $U_{Mn}$) or ($V_{10}$, $V_{11}$, . . . , $V_{1n}$, $V_{20}$, $V_{21}$, . . . , $V_{2n}$, . . . , $V_{M0}$, $V_{M1}$, . . . , $V_{Mn}$). Here, the unknown nodal distribution Q' can include the unknown, thermal conductivity nodal distribution $L'_{ij}$, $L_j'$, product nodal distribution of the density and specific heat $R'_{ij}$, $R'_j$, density or specific heat nodal distribution $S'_{ij}$, $S'_j$, thermal diffusivity nodal distribution $H_0'_{ij}$, $H_0'_j$, ratio distribution of the thermal conductivity and density $H_1'_{ij}$, $H_1'_j$, ratio distribution of the thermal conductivity and specific heat $H_2'_{ij}$, $H_2'_j$.

That is, the unknown sequence of the nodal distributions $(U_0, U_1, \ldots, U_n)$ for over the ROI or $(V_0, V_1, \ldots, V_n)$ for the composition region can be stably estimated by solving the following regularized normal equations for the unknown nodal vector $X_j = (U_0^T, U_1^T, \ldots, U_n^T)^T$ or $X_j = (V_0^T, V_1^T, \ldots, V_n^T)^T$ derived from the functional $\Pi_i(X_i)$ [eq. (95)].

$$\left\{ \begin{bmatrix} E_0 + W_0 & & & 0 \\ & E_1 + W_1 & & \\ & & \ddots & \\ 0 & & & E_n + W_n \end{bmatrix} + \begin{bmatrix} \lambda_{40} & & & 0 \\ & \lambda_{41} & & \\ & & \ddots & \\ 0 & & & \lambda_{4n} \end{bmatrix} G_t^T G_t + \begin{bmatrix} \lambda_{50} & & & 0 \\ & \lambda_{51} & & \\ & & \ddots & \\ 0 & & & \lambda_{5n} \end{bmatrix} G_t^T G_t G_t^T G_t \right\} \begin{bmatrix} U_0 \\ U_1 \\ \vdots \\ U_n \end{bmatrix} = \begin{bmatrix} e_0 \\ e_1 \\ \vdots \\ e_n \end{bmatrix} \quad (136)$$

Here, the matrix Ej and the vector ej (j=0~n) are respectively $\Sigma_{i=1}^{M} E'_{ij}$ and $\Sigma_{i=1}^{M} e'_{ij}$ using the matrix E'ij and the vector e'ij of the normal equations (98), and the matrix $W_j = \lambda_{1j} I + \lambda_2 G^T G + \lambda_{3j} G^T GG^T G$ where $\lambda_{1j} = \Sigma_{i=1}^{M}\lambda_{1ij}$, $\lambda_{2j} = \Sigma_{i=1}^{M}\lambda_{2ij}$, $\lambda_{3j} = \Sigma_{i=1}^{M}\lambda_{3ij}$, and $\lambda_{4j} = \Sigma_{i=1}^{M}\lambda_{4ij}$, $\lambda_{5j} = \Sigma_{i=1}^{M}\lambda_{5ij}$. Moreover, the matrix $G^T G$, $G^T GG^T G$, $Gt^T Gt$, $Gt^T Gt Gt^T Gt$ are respectively the finite-element-approximated or finite-difference (discrete)-approximated, above-described Laplacian and squared Laplacian operators, and temporal first and second order partial derivative operators with respect t (j) multiplied to the unknown nodal distributions Q' included by the unknown nodal distributions $(U_0, U_1, \ldots, U_n)$ or $(V_0, V_1, \ldots, V_n)$.

Thus, the unknown, thermal conductivity distribution Lij [ki(x,y,z,t) when the ROI is 3D], Li [ki(x,y,z)], L [k(x,y,z)], Lj [k(x,y,z,t)], product distribution of the density and specific heat Rij [ρci(x,y,z,t)], Ri [ρci(x,y,z)], R [ρc(x,y,z)], Rj [ρc(x,y,z,t)], specific heat distribution Sij [ci(x,y,z,t)], Si [ci(x,y,z)], S [c(x,y,z)], Sj [c(x,y,z,t)], density distribution Sij [ρi(x,y,z,t)], Si [ρi(x,y,z)], S [ρ(x,y,z)], Sj [ρ(x,y,z,t)], thermal diffusivity distribution $H_0$ij [$h_{0i}$(x,y,z,t)], $H_0$i [$h_{0i}$(x,y,z)], $H_0$ [$h_0$(x,y,z)], $H_{0j}$ [$h_0$(x,y,z,t)], ratio distribution of the thermal conductivity and density $H_1$ij [$h_{1i}$(x,y,z,t)], $H_1$i [$h_{1i}$(x,y,z)], $H_1$ [$h_1$(x,y,z)], $H_{1j}$ [$h_1$(x,y,z,t)], ratio distribution of the thermal conductivity and specific heat $H_2$ij [$h_{2i}$(x,y,z,t)], $H_2$i [$h_{2i}$(x,y,z)], $H_2$ [$h_2$(x,y,z)], $H_{2j}$ [$h_2$(x,y,z,t)] can be estimated. When using the finite element approximations, the above-described basis functions are used. As in the case when the ROI is 2D or 1D.

The respective regularization parameters $\lambda_{1ij}$, $\lambda_{2ij}$, $\lambda_{3ij}$, $\lambda_{4ij}$, $\lambda_{5ij}$ in the regularized normal equations (116) to (124) and (134) to (136), as in the regularized normal equations (19) derived using the above-described first principle, are set large such that the matrix multiplied to the unknown nodal vector U' or V' becomes numerically positive-definite for the respective temperatures Tij. Otherwise, the respective regularization parameters $\alpha_{1ij}$, $\alpha_{2ij}$, $\alpha_{3ij}$, $\alpha_{4ij}$, $\alpha_{5ij}$, $\beta_{1ij}$, $\beta_{2ij}$, $\beta_{3ij}$, $\beta_{4ij}$, $\beta_{5ij}$, $\chi_{1ij}$, $\chi_{2ij}$, $\chi_{3ij}$, $\chi_{4ij}$, $\chi_{5ij}$, $\delta_{1ij}$, $\delta_{2ij}$, $\delta_{3ij}$, $\delta_{4ij}$, $\delta_{5ij}$, $\epsilon_{1ij}$, $\epsilon_{2ij}$, $\epsilon_{3ij}$, $\epsilon_{4ij}$, $\epsilon_{5ij}$, $\gamma_{1ij}$, $\gamma_{2ij}$, $\gamma_{3ij}$, $\gamma_{4ij}$, $\gamma_{5ij}$, $\eta_{1ij}$, $\eta_{2ij}$, $\eta_{3ij}$, $\eta_{4ij}$, $\eta_{5ij}$ determining $\lambda_{1ij}$, $\lambda_{2ij}$, $\lambda_{3ij}$, $\lambda_{4ij}$, $\lambda_{5ij}$ can be set with respect to the accuracies (SNRs) of the spatial and temporal partial derivative distributions data of the temperature (temporal first order partial derivative distributions data of the temperature, temperature gradient vector distributions data, divergence distributions data of the temperature gradient vector) in the respective composition regions [eqs. (107) to (115) and (125) to (133)] for the respective temperature distributions Tij.

Specifically, the regularization parameters multiplied to the unknown nodal distributions $R'_{ij}$, $R'_i$, $R'$, $R'_j$ in the unknown nodal vector U' or V' can be controlled by the accuracies (SNRs) of the temporal first order partial derivative distributions data of the temperature in the integral regions of the respective penalty terms. Otherwise, the regularization parameters multiplied to the unknown nodal distributions $S'_{ij}$, $S'_i$, $S'$, $S'_j$ in the unknown nodal vectors U' or V' can be controlled by the accuracies (SNRs) of the product distributions data of the temporal first order partial derivative of the temperature and the given either density or specific heat in the integral regions of the respective penalty terms.

Otherwise, the regularization parameters multiplied to the unknown nodal distributions $L'_{ij}$, $L'_i$, $L'$, $L'_j$, $H_0'_{ij}$, $H_0'_i$, $H_0'$, $H_0'_j$, $H_1'_{ij}$, $H_1'_i$, $H_1'$, $H_1'_j$, $H_2'_{ij}$, $H_2'_i$, $H_2'$, $H_2'_j$ in the unknown nodal vectors U' or V' derived from the functionals Iij(.) [eqs. (49) to (71) and (77) to (88)] in the functionals IIij (U') [eqs. (89) to (97)] can be controlled by the accuracies (SNRs) of the inner product distributions data of the temperature gradient vector and the gradient operator applied to the unknown thermal conductivity k, thermal diffusivity $h_0$, ratio of the thermal conductivity and density $h_1$ or ratio of the thermal conductivity and specific heat $h_2$, and the divergence distributions data of the temperature gradient vector in the integral regions of the respective penalty terms.

Otherwise, the regularization parameters multiplied to the unknown nodal distributions $L'_{ij}$, $L'_i$, $L'$, $L'_j$, $H_0'_{ij}$, $H_0'_i$, $H_0'$, $H_0'_j$, $H_1'_{ij}$, $H_1'_i$, $H_1'$, $H_1'_j$, $H_2'_{ij}$, $H_2'_i$, $H_2'$, $H_2'_j$ in the unknown nodal vectors U' or V' derived from the functionals Iij(.) [eqs. (72) to (75)] in the functionals IIij(U') [eqs. (89) to (97)] can be controlled by the accuracies (SNRs) of the temperature gradient vector distributions in the integral regions of the respective penalty terms.

That is, when the SNR is higher, they are set smaller, vice versa.

For instance, the regularization parameters multiplied to the unknown nodal distributions $R'_{ij}$, $R'_i$, $R'$, $R'_j$ in the unknown nodal vectors U' or V' can be set proportional to the reciprocals of the SNRs of the powers of the temporal first order partial derivative distributions data of the temperature in the integral regions of the respective penalty terms.

Otherwise, the regularization parameters multiplied to the unknown nodal distributions $S'_{ij}$, $S'_i$, $S'$, $S'_j$ in the unknown nodal vectors $U'$ or $V'$ can be set proportional to the reciprocals of the SNRs of the powers of the product distributions of the temporal first order partial derivative of the temperature and the given either density or specific heat in the integral regions of the respective penalty terms.

Otherwise, the regularization parameters multiplied to the unknown nodal distributions $L'_{ij}$, $L'_i$, $L'$, $L'_j$, $H_0'_{ij}$, $H_0'_i$, $H_0'$, $H_0'_j$, $H_1'_{ij}$, $H_1'_i$, $H_1'$, $H_1'_j$, $H_2'_{ij}$, $H_2'_i$, $H_2'$, $H_2'_j$ in the unknown nodal vectors $U'$ or $V'$ derived from the functionals Iij(.) [eqs. (49) to (71) and (77) to (88)] in the functionals IIij ($U'$) [eqs. (89) to (97)] can be set proportional to the reciprocals of the SNRs of the powers of the summations of the inner product distributions data of the temperature gradient vector and the gradient operator applied to the unknown thermal conductivity k, thermal diffusivity $h_0$, ratio of the thermal conductivity and density $h_1$ or ratio of the thermal conductivity and specific heat $h_2$, and the divergence distributions data of the temperature gradient vector in the integral regions of the respective penalty terms.

Otherwise, the regularization parameters multiplied to the unknown nodal distributions $L'_{ij}$, $L'_i$, $L'$, $L'_j$, $H_0'_{ij}$, $H_0'_i$, $H_0'$, $H_0'_j$, $H_1'_{ij}$, $H_1'_i$, $H_1'$, $H_1'_j$, $H_2'_{ij}$, $H_2'_i$, $H_2'$, $H_2'_j$ in the unknown nodal vectors $U'$ or $V'$ derived from the functionals Iij(.) [eqs. (72) to (75)] in the functionals IIij($U'$) [eqs. (89) to (97)] can be set proportional to the reciprocals of the SNRs of the powers of the temperature gradient vector distributions in the integral regions of the respective penalty terms.

Here, the SNRs of the spatial and temporal partial derivative distributions data of the temperature (the temporal first derivative distribution of the temperature or temperature gradient vector distribution) depend on the measured sequential temperature distributions data itself and the spatial and temporal intervals of the data (i.e., the direction of the partial derivative of the temperature and magnitudes of the derivatives). In addition, the SNR also depends on the direction of the aperture. Thus, the SNRs of the partial derivatives differ each other.

Therefore, the regularization parameters $\alpha_{2ij}$, $\alpha_{3ij}$, $\alpha_{4ij}$, $\alpha_{5ij}$, $\beta_{2ij}$, $\beta_{3ij}$, $\beta_{4ij}$, $\beta_{5ij}$, $\chi_{2ij}$, $\chi_{3ij}$, $\chi_{4ij}$, $\chi_{5ij}$, $\delta_{2ij}$, $\delta_{3ij}$, $\delta_{4ij}$, $\delta_{5ij}$, $\epsilon_{2ij}$, $\epsilon_{3ij}$, $\epsilon_{4ij}$, $\epsilon_{5ij}$, $\gamma_{2ij}$, $\gamma_{3ij}$, $\gamma_{4ij}$, $\gamma_{5ij}$, $\eta_{2ij}$, $\eta_{3ij}$, $\eta_{4ij}$, $\eta_{5ij}$ can be respectively set for the directions of the partial derivatives in the penalty terms (107) to (115) and (125) to (133). That is, the regularization parameters can be set small and large respectively when the SNR (accuracy) of measured temperature derivative distribution data is high and low for the respective measured temperature distributions Tij in the composition (integral) regions.

Specifically, the regularization parameters $\beta_{2ij}$ and $\beta_{3ij}$ can be controlled by the accuracies (SNRs) of the respective changes of the first order partial derivative of the temperature in I, J and K directions in the distances $\Delta x$, $\Delta y$ and $\Delta z$. The regularization parameters $\chi_{2ij}$ and $\chi_{3ij}$ can be controlled by the accuracies (SNRs) of the respective changes of the product of the first order partial derivative of the temperature and given specific heat in I, J and K directions in the distances $\Delta x$, $\Delta y$ and $\Delta z$. The regularization parameters $\delta_{2ij}$ and $\delta_{3ij}$ can be controlled by the accuracies (SNRs) of the respective changes of the first order partial derivative of the temperature and given density in I, J and K directions in the distances $\Delta x$, $\Delta y$ and $\Delta z$. Moreover, the regularization parameters $\beta_{4ij}$, $\beta_{5ij}$, $\chi_{4ij}$, $\chi_{5ij}$, $\delta_{4ij}$ and $\delta_{5ij}$ can be controlled by the accuracies (SNRs) of the change of the first order partial derivative of the temperature in j direction in the distance $\Delta t$.

Otherwise, the regularization parameters $\alpha_{2ij}$, $\alpha_{3ij}$, $\epsilon_{2ij}$, $\epsilon_{3ij}$, $\gamma_{2ij}$, $\gamma_{3ij}$, $\eta_{2ij}$ and $\eta_{3ij}$ when the functionals Iij(.) of eqs. (49) to (71) and eqs. (77) to (88) are used, can be controlled by the accuracies (SNRs) of the product distributions data of the temperature gradient vector components and the gradient operator components applied to the unknown thermal conductivity k, thermal diffusivity $h_0$, ratio of the thermal conductivity and density $h_1$ or ratio of the thermal conductivity and specific heat $h_2$, and those of the divergence components of the temperature gradient vector. Otherwise, the regularization parameters can be controlled by the accuracies (SNRs) of the changes of the inner product distribution of the temperature gradient vector and the gradient operator applied to the unknown thermal conductivity k, thermal diffusivity $h_0$, ratio of the thermal conductivity and density $h_1$ or ratio of the thermal conductivity and specific heat $h_2$ and the changes of the divergence distribution of the temperature gradient vector in the directions I, J, and K in the distances $\Delta x$, $\Delta y$ and $\Delta z$.

Otherwise, the regularization parameters $\alpha_{2ij}$, $\alpha_{3ij}$, $\epsilon_{2ij}$, $\epsilon_{3ij}$, $\gamma_{2ij}$, $\gamma_{3ij}$, $\eta_{2ij}$ and $\eta_{3ij}$ when the functionals Iij(.) of eqs. (72) to (75) are used, can be controlled by the accuracies (SNRs) of the temperature gradient vector component distributions data, or by the changes of the magnitude distribution of the temperature gradient vector in the directions I, J and K in the distances $\Delta x$, $\Delta y$ and $\Delta z$.

Otherwise, the regularization parameters $\alpha_{4ij}$, $\alpha_{5ij}$, $\epsilon_{4ij}$, $\epsilon_{5ij}$, $\gamma_{4ij}$, $\gamma_{5ij}$, $\eta_{4ij}$ and $\eta_{5ij}$, when the functionals Iij(.) of eqs. (49) to (71) and eqs. (77) to (88) are used, can be controlled by the accuracies (SNRs) of the change of the inner product distribution of the temperature gradient vector and the gradient operator applied to the unknown thermal conductivity k, thermal diffusivity $h_0$, ratio of the thermal conductivity and density $h_1$, or ratio of the thermal conductivity and specific heat $h_2$ and the change of the divergence distribution of the temperature gradient vector in j direction in the distance $\Delta t$. Otherwise, the regularization parameters $\alpha_{4ij}$, $\alpha_{5ij}$, $\epsilon_{4ij}$, $\epsilon_{5ij}$, $\gamma_{4ij}$, $\gamma_{5ij}$, $\eta_{4ij}$ and $\eta_{5ij}$, when the functionals Iij(.) of eqs. (72) to (75) are used, can be controlled by the accuracies (SNRs) of the change of the magnitude distribution of the temperature gradient vector in j direction in the distance $\Delta t$.

For instance, the regularization parameters can be set proportional to the reciprocals of the SNRs of the powers evaluated in the composition (integral) regions.

In such cases, the respective regularization parameters can also be set, for instance, small and large when the data distance is long and short (for instance, such that they becomes proportional to the reciprocal of the squared distance). Thus, these regularization parameters can also be set proportional to the product of the weighted values determined by the respective factors determining the SNRs of the temperature derivative distributions data and the respective component distributions for the respective measured temperature distributions Tij in the respective composition (integral) regions.

Here, the measurement of the SNR (accuracy) of the sequential temperature measurement is performed to evaluate the accuracy of the measurement equipment. The SNR of the power can be estimated from the ratio of the squared mean and variance of the temperature distributions measured for a flat black body having a constant temperature. Alternatively, to evaluate the accuracy of the measurement equipment and environment, by using the same environment or by realizing the same environment, the SNR can be estimated for the target itself or a black body. The SNRs of the spatial and temporal derivatives of the temperature distributions over the ROI can be estimated from the temperature derivatives data of the discrete coordinates (I,J,K) for the finite difference approximation case and of the nodes (I,J,K) of each element for the finite element approximation case.

The respective regularization parameters $\alpha_{1ij}$, $\alpha_{2ij}$, $\alpha_{3ij}$, $\alpha_{4ij}$, $\alpha_{5ij}$, $\beta_{1ij}$, $\beta_{2ij}$, $\beta_{3ij}$, $\beta_{4ij}$, $\beta_{5ij}$, $\chi_{1ij}$, $\chi_{2ij}$, $\chi_{3ij}$, $\chi_{4ij}$, $\chi_{5ij}$, $\delta_{1ij}$, $\delta_{2ij}$, $\delta_{3ij}$, $\delta_{4ij}$, $\delta_{5ij}$, $\epsilon_{1ij}$, $\epsilon_{2ij}$, $\epsilon_{3ij}$, $\epsilon_{5ij}$, $\gamma_{1ij}$, $\gamma_{2ij}$, $\gamma_{3ij}$, $\gamma_{4ij}$, $\gamma_{5ij}$, $\eta_{1ij}$, $\eta_{2ij}$, $\eta_{3ij}$, $\eta_{4ij}$, $\eta_{5ij}$ determining $\lambda_{1ij}$, $\lambda_{2ij}$, $\lambda_{3ij}$, $\lambda_{4ij}$, $\lambda_{5ij}$ can be set spatially varying in the respective composition (integral) regions of the penalty terms (107) to (115) and (125) to (133). Thus, these regularization parameters can be set large at each point of interest such that the local matrix multiplied to the unknown nodal value in the vector U' or V' becomes numerically positive-definite for the respective temperatures Tij. Otherwise, The respective regularization parameters $\alpha_{1ij}$, $\alpha_{2ij}$, $\alpha_{3ij}$, $\alpha_{4ij}$, $\alpha_{5ij}$, $\beta_{1ij}$, $\beta_{2ij}$, $\beta_{3ij}$, $\beta_{4ij}$, $\beta_{5ij}$, $\chi_{1ij}$, $\chi_{2ij}$, $\chi_{3ij}$, $\chi_{4ij}$, $\chi_{5ij}$, $\delta_{1ij}$, $\delta_{2ij}$, $\delta_{3ij}$, $\delta_{4ij}$, $\delta_{5ij}$, $\epsilon_{1ij}$, $\epsilon_{2ij}$, $\epsilon_{3ij}$, $\epsilon_{4ij}$, $\epsilon_{5ij}$, $\gamma_{1ij}$, $\gamma_{2ij}$, $\gamma_{3ij}$, $\gamma_{4ij}$, $\gamma_{5ij}$, $\eta_{1ij}$, $\eta_{2ij}$, $\eta_{3ij}$, $\eta_{4ij}$, $\eta_{5ij}$ determining $\lambda_{1ij}$, $\lambda_{2ij}$, $\lambda_{3ij}$, $\lambda_{4ij}$, $\lambda_{5ij}$ can be controlled at each point of interest according to the accuracies (SNRs) of the spatial and temporal partial derivatives of the temperature data (temporal first order partial derivative of the temperature data, temperature gradient vector data, divergence of the temperature gradient vector data) in the respective composition regions of the penalty terms of (107) to (115) and (125) to (133) for the respective temperature distributions Tij.

Specifically, the regularization parameters multiplied to the unknown nodal distributions $R'_{ij}$, $R'_I$, $R'$, $R'_j$ in the unknown nodal vectors U' or V' can be controlled at each point of interest by the accuracy (SNR) of the temporal first order partial derivative of the temperature data.

Otherwise, the regularization parameters multiplied to the unknown nodal distributions $S'_{ij}$, $S'_I$, $S'$, $S'_j$ in the unknown nodal vectors U' or V' can be controlled at each point of interest proportional by the accuracy (SNR) of the product of the temporal first order partial derivative of the temperature and the given either density or specific heat.

Otherwise, the regularization parameters multiplied to the unknown nodal distributions $L'_{ij}$, $L'_I$, $L'$, $L'_j$, $H_0{'}_{ij}$, $H_0{'}_I$, $H_0{'}$, $H_0{'}_j$, $H_1{'}_{ij}$, $H_1{'}_I$, $H_1{'}$, $H_1{'}_j$, $H_2{'}_{ij}$, $H_2{'}_I$, $H_2{'}$, $H_2{'}_j$ in the unknown nodal vectors U' or V' derived from the functionals Iij(.) [eqs. (49) to (71) and (77) to (88)] in the functionals IIij(U') [eqs. (89) to (97)] can be controlled at each point of interest by the accuracies (SNRs) of the inner product of the temperature gradient vector and the gradient operator applied to the unknown thermal conductivity k, thermal diffusivity $h_0$, ratio of the thermal conductivity and density $h_1$ or ratio of the thermal conductivity and specific heat $h_2$, and the accuracy (SNR) of the divergence of the temperature gradient vector.

Otherwise, the regularization parameters multiplied to the unknown nodal distributions $L'_{ij}$, $L'_I$, $L'$, $L'_j$, $H_0{'}_{ij}$, $H_0{'}_I$, $H_0{'}$, $H_0{'}_j$, $H_1{'}_{ij}$, $H_1{'}_I$, $H_1{'}$, $H_1{'}_j$, $H_2{'}_{ij}$, $H_2{'}_I$, $H_2{'}$, $H_2{'}_j$ in the unknown nodal vectors U' or V' derived from the functionals Iij(.) [eqs. (72) to (75)] in the functionals IIij(U') [eqs. (89) to (97)] can be controlled at each point of interest by the accuracy (SNR) of the temperature gradient vector.

That is, when the SNR is higher, they are set smaller, vice versa.

For instance, the regularization parameters multiplied to the unknown nodal distributions $R'_{ij}$, $R'_I$, $R'$, $R'_j$ in the unknown nodal vectors U' or V' can be set at each point of interest proportional to the reciprocal of the SNR of the power of the temporal first order partial derivative of the temperature data.

Otherwise, the regularization parameters multiplied to the unknown nodal distributions $S'_{ij}$, $S'_I$, $S'$, $S'_j$ in the unknown nodal vectors U' or V' can be set at each point of interest proportional to the reciprocal of the SNR of the power of the the product of the temporal first order partial derivative of the temperature and the given either density or specific heat.

Otherwise, the regularization parameters multiplied to the unknown nodal distributions $L'_{ij}$, $L'_I$, $L'$, $L'_j$, $H_0{'}_{ij}$, $H_0{'}_I$, $H_0{'}$, $H_0{'}_j$, $H_1{'}_{ij}$, $H_1{'}_I$, $H_1{'}$, $H_1{'}_j$, $H_2{'}_{ij}$, $H_2{'}_I$, $H_2{'}$, $H_2{'}_j$ in the unknown nodal vectors U' or V' derived from the functionals Iij(.) [eqs. (49) to (71) and (77) to (88)] in the functionals IIij (U') [eqs. (89) to (97)] can be set at each point of interest proportional to the reciprocal of the SNR of the power of the summation of the inner product of the temperature gradient vector and the gradient operator applied to the unknown thermal conductivity k, thermal diffusivity $h_0$, ratio of the thermal conductivity and density $h_1$ or ratio of the thermal conductivity and specific heat $h_2$, and the divergence of the temperature gradient vector.

Otherwise, the regularization parameters multiplied to the unknown nodal distributions $L'_{ij}$, $L'_I$, $L'$, $L'_j$, $H_0{'}_{ij}$, $H_0{'}_I$, $H_0{'}$, $H_0{'}_j$, $H_1{'}_{ij}$, $H_1{'}_I$, $H_1{'}$, $H_1{'}_j$, $H_2{'}_{ij}$, $H_2{'}_I$, $H_2{'}$, $H_2{'}_j$ in the unknown nodal vectors U' or V' derived from the functionals Iij(.) [eqs. (72) to (75)] in the functionals IIij(U') [eqs. (89) to (97)] can be set at each point proportional to the reciprocal of the SNR of the power of the temperature gradient vector.

Here, the SNRs of the spatial and temporal partial derivative distributions data of the temperature (the temporal first derivative distribution of the temperature or temperature gradient vector distribution) depend on the measured sequential temperature distributions data itself and the spatial and temporal intervals of the data (i.e., the direction of the partial derivative of the temperature and magnitudes of the derivatives). In addition, the SNR also depends on the direction of the aperture. Thus, the SNRs of the partial derivatives differ each other at each point. Accordingly, the regularization parameters $\alpha_{2ij}$, $\alpha_{3ij}$, $\alpha_{4ij}$, $\alpha_{5ij}$, $\beta_{2ij}$, $\beta_{3ij}$, $\beta_{4ij}$, $\beta_{5ij}$, $\chi_{2ij}$, $\chi_{3ij}$, $\chi_{4ij}$, $\chi_{5ij}$, $\delta_{2ij}$, $\delta_{3ij}$, $\delta_{4ij}$, $\delta_{5ij}$, $\epsilon_{2ij}$, $\epsilon_{3ij}$, $\epsilon_{4ij}$, $\epsilon_{5ij}$, $\gamma_{2ij}$, $\gamma_{3ij}$, $\gamma_{4ij}$, $\gamma_{5ij}$, $\eta_{2ij}$, $\eta_{3ij}$, $\eta_{4ij}$, $\eta_{5ij}$ are set for the respective spatial and temporal directions of the penalty terms (107) to (115) and (125) to (133) at each point of interest. That is, respective these regularization parameters can be controlled according to the SNRs of the temperature spatial and temporal derivatives at each point for the respective temperature distributions data Tij such that each parameter is set small for the spatial and temporal direction of the high SNR component and vice versa.

Specifically, the regularization parameters $\beta_{2ij}$ and $\beta_{3ij}$ can be controlled at each point by the accuracies (SNRs) of the respective changes of the first order partial derivative of the temperature in I, J and K directions in the distances $\Delta x$, $\Delta y$ and $\Delta z$. The regularization parameters $\chi_{2ij}$ and $\chi_{3ij}$ can be controlled at each point by the accuracies (SNRs) of the respective changes of the product of the first order partial derivative of the temperature and given specific heat in I, J and K directions in the distances $\Delta x$, $\Delta y$ and $\Delta z$. The regularization parameters $\delta_{2ij}$ and $\delta_{3ij}$ can be controlled at each point by the accuracies (SNRs) of the respective changes of the first order partial derivative of the temperature and given density in I, J and K directions in the distances $\Delta x$, $\Delta y$ and $\Delta z$. Moreover, the regularization parameters $\beta_{4ij}$, $\beta_{5ij}$, $\chi_{4ij}$, $\chi_{5ij}$, $\delta_{4ij}$ and $\delta_{5ij}$ can be controlled at each point by the accuracies (SNRs) of the change of the first order partial derivative of the temperature in j direction in the distance $\Delta t$.

Otherwise, the regularization parameters $\alpha_{2ij}$, $\alpha_{3ij}$, $\epsilon_{2ij}$, $\epsilon_{3ij}$, $\gamma_{2ij}$, $\gamma_{3ij}$, $\eta_{2ij}$ and $\eta_{3ij}$ when the functionals Iij(.) of eqs. (49) to (71) and eqs. (77) to (88) are used, can be controlled at each point by the accuracies (SNRs) of the products of the temperature gradient vector components and the gradient operator components applied to the unknown thermal conductivity k, thermal diffusivity $h_0$, ratio of the thermal conductivity and density $h_1$ or ratio of the thermal conductivity and specific heat $h_2$, and the divergence components of the temperature gradient vector. Otherwise, the regularization parameters can be controlled at each point by the accuracies (SNRs) of the changes of the inner product of the temperature gradient vector and the gradient operator applied to the unknown thermal conductivity k, thermal diffusivity $h_0$, ratio of the thermal conductivity and density $h_1$ or ratio of the thermal conductivity and specific heat $h_2$ and the changes of the divergence of the temperature gradient vector in the directions I, J, and K in the distances $\Delta x$, $\Delta y$ and $\Delta z$. Otherwise, the regularization parameters $\alpha_{2ij}$, $\alpha_{3ij}$, $\epsilon_{2ij}$, $\epsilon_{3ij}$, $\gamma_{2ij}$, $\gamma_{3ij}$, $\eta_{2ij}$ and $\eta_{3ij}$ when the functionals Iij(.) of eqs. (72) to (75) are used, can be controlled at each point by the accuracies (SNRs) of the temperature gradient vector components, or by the changes of the magnitude of the temperature gradient vector in the directions I, J and K in the distances $\Delta x$, $\Delta y$ and $\Delta z$.

Otherwise, the regularization parameters $\alpha_{4ij}$, $\alpha_{5ij}$, $\epsilon_{4ij}$, $\epsilon_{5ij}$, $\gamma_{4ij}$, $\gamma_{5ij}$, $\eta_{4ij}$ and $\eta_{5ij}$, when the functionals Iij(.) of eqs. (49) to (71) and eqs. (77) to (88) are used, can be controlled at each point by the accuracies (SNRs) of the change of the inner product of the temperature gradient vector and the gradient operator applied to the unknown thermal conductivity k, thermal diffusivity $h_0$, ratio of the thermal conductivity and density $h_1$, or ratio of the thermal conductivity and specific heat $h_2$ and the change of the divergence of the temperature gradient vector in j direction in the distance $\Delta t$. Otherwise, the regularization parameters $\alpha_{4ij}$, $\alpha_{5ij}$, $\epsilon_{4ij}$, $\epsilon_{5ij}$, $\gamma_{4ij}$, $\gamma_{5ij}$, $\eta_{4ij}$ and $\eta_{5ij}$, when the functionals Iij(.) of eqs. (72) to (75) are used, can be controlled by the accuracy (SNR) of the change of the magnitude of the temperature gradient vector in j direction in the distance $\Delta t$.

For instance, the regularization parameters can be set at each point proportional to the reciprocals of the SNRs of the powers evaluated in the composition (integral) regions. In such cases, the respective regularization parameters can also be set, for instance, small and large when the data distance is long and short (for instance, such that they becomes proportional to the reciprocal of the squared distance). Thus, these regularization parameters can also be set proportional to the product of the weighted values determined by the respective factors determining the SNRs of the temperature derivatives and the respective components for the respective measured temperature distributions Tij in the respective composition (integral) regions.

Here, the measurement of the SNR (accuracy) of the sequential temperature measurement is performed to evaluate the accuracy of the measurement equipment. The SNR of the power can be estimated from the ratio of the squared mean and variance of the temperatures measured for a flat black body having a constant temperature. Alternatively, to evaluate the accuracy of the measurement equipment and environment, by using the same environment or by realizing the same environment, the SNR can be estimated for the target itself or a black body. The SNRs of the spatial and temporal derivatives of the temperatures over the ROI can be estimated from the temperature derivatives data of the discrete coordinates (I,J,K) for the finite difference approximation case and of the nodes (I,J,K) of each element for the finite element approximation case.

(II) Otherwise, according to the first and second principles, by utilizing the spectra of the unknown thermal property distributions in eqs. (41), (43), (45) and (47), the regularization can also be performed in the frequency direction as well as the temporal and spatial directions [different from (I)].

For instance, when the distributions of the frequency variances of the thermal conductivity $k_i(x,y,z,t)$ and product of the density and specific heat $\rho c_i(x,y,z,t)$ [i.e., spectra and phases] are measurement targets, the sequence of the thermal conductivity distribution $ki(x,y,z,j)$ [expressed as $\sim \Sigma_{I,J,K} \phi_{3k}(I,J,K,x,y,z) ki(I,J,K,j)$ using the prespecified basis function in the discrete spatial domain (x,y,z,I,J,K)] can be expressed as $$k_i(x, y, z, j) = \frac{1}{n+1} \sum_{l=0}^{n} [k_i(x, y, z, l) \exp(j\theta_{ki}(x, y, z, l))]$$

$$[\cos(2\pi l\Delta f j\Delta t) + j\sin(2\pi l\Delta f j\Delta t)]$$

using the spectra $ki(x,y,z,l)$ and phases $\theta_{ki}(x,y,z,l)$ [where, l is frequency], i.e., the real and imaginary components $ki(x,y,z,l)\cos\theta_{ki}(x,y,z,l)$ and $ki(x,y,z,l)\sin\theta_{ki}(x,y,z,l)$ of the spectra, obtained by performing with respect to time direction j the Fast Fourier's Transform, Maximum Entropy Method (MEM), short time spectrum analysis, etc. Here, j (bold) denotes the imaginary unit, i (=1~M) denotes the independent measured sequence of the temperature $T_i(x,y,z,t)$. M is the number of the independent measured sequences of the temperatures ($\geqq 1$), j (=0~n) is the discrete temporal coordinate, and the frequency f is expressed as $f = l\Delta f$ using the frequency resolution $\Delta f$.

Moreover, the sequence of the product of the density and specific heat distribution $\rho c_i(x,y,z,j)$ [expressed as $\sim \Sigma_{I,J,K} \phi_{3\rho c}(I,J,K,x,y,z)\rho c_i(I,J,K,j)$ using the prespecified basis function in the discrete spatial domain (x,y,z,I,J,K)] can be expressed as $$\rho c_i(x, y, z, j) = \frac{1}{n+1} \sum_{l=0}^{n} [\rho c_i(x, y, z, l) \exp(j\theta_{\rho ci}(x, y, z, l))]$$

$$[\cos(2\pi l\Delta f j\Delta t) + j\sin(2\pi l\Delta f j\Delta t)]$$

using the spectra $\rho c_i(x,y,z,l)$ and phases $\theta_{\rho ci}(x,y,z,l)$ [where, l is the frequency], i.e., the real and imaginary components $\rho c_i(x,y,z,l)\cos\theta_{\rho ci}(x,y,z,l)$ and $\rho c_i(x,y,z,l)\sin\theta_{\rho ci}(x,y,z,l)$ of the spectra, obtained by performing with respect to time direction j the Fast Fourier's Transform, Maximum Entropy Method (MEM), short time spectrum analysis, etc.

Thus, the first order partial derivative (41) can be expressed as $$\sum_{l=0}^{n} \left[ \frac{d}{dt} T_i(x, y, z, j) \{\rho c_i(x, y, z, l) \exp(j\theta_{\rho ci}(x, y, z, l))\} \right. \quad (137)$$

$$\{\cos(2\pi l\Delta f j\Delta t) + j\sin(2\pi l\Delta f j\Delta t)\} +$$

$$\left( D_{ix}(x, y, z, j) \frac{\partial}{\partial x} k_i(x, y, z, l) + D_{iy}(x, y, z, j) \frac{\partial}{\partial y} k_i(x, y, z, l) + \right.$$

$$D_{iz}(x, y, z, j) \frac{\partial}{\partial z} k_i(x, y, z, l) +$$

$$\frac{\partial}{\partial x} D_{ix}(x, y, z, j) k_i(x, y, z, l) + \frac{\partial}{\partial y} D_{iy}(x, y, z, j)$$

$$k_i(x, y, z, l) + \frac{\partial}{\partial z} D_{iz}(x, y, z, j) k_i(x, y, z, l) \right)$$

$$\exp(j\theta_{ki}(x, y, z, l) \{\cos(2\pi l\Delta f j\Delta t) + j\sin(2\pi l\Delta f j\Delta t)\}) = 0.$$

Then, for the respective frequency l, the following simultaneous differential equations hold, i.e., $$\frac{d}{dt}T_i(x,y,z,j)\{\rho c_i(x,y,z,l)\cos\theta_{\rho ci}(x,y,z,l)\} + \quad (137')$$

$$\left\{\left(D_{ix}(x,y,z,j)\frac{\partial}{\partial x}k_i(x,y,z,l) + D_{iy}(x,y,z,j)\frac{\partial}{\partial y}k_i(x,y,z,l) + \right.\right.$$

$$D_{iz}(x,y,z,j)\frac{\partial}{\partial z}k_i(x,y,z,l) + \frac{\partial}{\partial x}D_{ix}(x,y,z,j)$$

$$k_i(x,y,z,l) + \frac{\partial}{\partial y}D_{iy}(x,y,z,j)k_i(x,y,z,l) +$$

$$\left.\frac{\partial}{\partial z}D_{iz}(x,y,z,j)k_i(x,y,z,l)\right)\cos\theta_{ki}(x,y,z,l) = 0,$$

$$\frac{d}{dt}T_i(x,y,z,j)\{\rho c_i(x,y,z,l)\sin\theta_{\rho ci}(x,y,z,l)\} + \quad (137'')$$

$$\left\{\left(D_{ix}(x,y,z,j)\frac{\partial}{\partial x}k_i(x,y,z,l) + D_{ix}(x,y,z,j)\frac{\partial}{\partial y}k_i(x,y,z,l) + \right.\right.$$

$$D_{iz}(x,y,z,j)\frac{\partial}{\partial z}k_i(x,y,z,l) + \frac{\partial}{\partial x}D_{ix}(x,y,z,j)$$

$$k_i(x,y,z,l) + \frac{\partial}{\partial y}D_{iy}(x,y,z,j)k_i(x,y,z,l) +$$

$$\left.\frac{\partial}{\partial z}D_{iz}(x,y,z,j)k_i(x,y,z,l)\right)\sin\theta_{ki}(x,y,z,l) = 0,$$

Therefore, the first order partial differential equations (137') and (137") can be finite-element-approximated (based on calculus of variations or Galerkin's method) in the same way as that of (I) [the finite-element approximation is applied to the first order partial differential equations (41) for the respective sequences i (=1~M) at each time j (=0~n)].

In this case, after approximating the sequential, temperature distributions $T_i(x,y,z,t)$, temporal first order partial derivative of the temperature $dT/dt(x,y,z,t)$, temperature gradient vector component distributions $D_{ix}(x,y,z,t)$, $D_{iy}(x,y,z,t)$ and $D_{iz}(x,y,z,t)$, the divergence of the temperature gradient vector using the respective sequential nodal distributions and the respective basis functions, i.e., $T_i(I,J,K,j)$, $dT/dt(I,J,K,j)$, $D_{ix}(I,J,K,j)$, $D_{iy}(I,J,K,j)$ and $D_{iz}(I,J,K,j)$, the low-pass-filtered nodal data of each time j (=0~n) of the respective sequences i (=1~M) are substituted into the algebra equations derived from one of the functionals.

When using the finite-difference approximations, after expressing the respective distributions using the nodal distributions, the nodal distributions data are substituted into the derived finite-difference equations.

Moreover, by substituting the spectra (real and imaginary of frequency l) of the sequences of the respective reference (known) thermal property nodal distributions [i.e., the thermal conductivity, $k_i(I,J,K,l)\cos\theta_{ki}(I,J,K,l)$ and $k_i(I,J,K,l)\sin\theta_{ki}(I,J,K,l)$; the product of the density and specific heat, $\rho c_i(I,J,K,l)\cos\theta_{\rho ci}(I,J,K,l)$ and $\rho c_i(I,J,K,l)\sin\theta_{\rho ci}(I,J,K,l)$] into the algebra equations, the two equations of (76) are derived for the spectra (real and imaginary) of the sequences of the respective thermal property nodal distributions of each frequency l (0~n) of time j (=0~n) of the respective sequences i (=1~M), i.e., the sequential, thermal conductivity distribution $k_i(I,J,K,l)\cos\theta_{ki}(I,J,K,l)$ and $ki(I,J,K,l)\sin\theta_{ki}(I,J,K,l)$; product distribution of the density and specific heat $\rho c_i(I,J,K,l)\cos\theta_{\rho ci}(I,J,K,l)$ and $\rho c_i(I,J,K,l)\sin\theta_{\rho ci}(I,J,K,l)$.

Thus, for all the first order partial differential equations (41), (43), (45) and (47), the algebra equations (76) are similarly derived for the spectra (real and imaginary) of the respective unknown nodal thermal property distributions.

Below, the algebra equations are used and further regularized. As described above, the equations can be normalized using Pij.

(A) The two algebra equations [eqs. (76) and (98)] derived for each frequency l of time j (j=0~n) of the respective sequences i (=1~M) can be respectively solved for the reals and imaginaries of the spectra of the unknown thermal property distributions ($\geq 1$).

(B) The two algebra equations derived for each frequency l of the different time j (j=0~n) of the different sequences i (=1~M) can be simultaneously solved for the respective reals and imaginaries of the spectra of all the unknown thermal property distributions [i.e., normal equations (99) to (106)].

(c) When the two algebra equations derived for each frequency l of the different time j (j=0~n) of the different sequences i (=1~M) are simultaneously solved for the respective reals and imaginaries of the spectra of all the unknown thermal property distributions, to stabilize the estimations, the respective simultaneous equations are regularized using the penalty terms (107) to (115) [i.e., normal equations (116) to (124)]. In this case, the regularization parameters multiplied to the unknown, respective real and imaginary of the spectra of the frequency l thermal property distributions can be set proportional to the reciprocals of the SNRs of the powers at the frequency at the time or during the times in the respective composition (integral) regions of the thermal quantities multiplied to the unknown thermal property distributions in eqs. (41), (43), (45) and (47). For instance, when the density is unknown, as described above, the product of the specific heat and the temporal first order partial derivative dT/dt. When the thermal conductivity is unknown, the temperature gradient vector and the divergence. Furthermore, the regularization parameters can also be set dependent on the time and position.

(D) When the two algebra equations derived for each frequency l of the different time j (j=0~n) of the different sequences i (=1~M) are simultaneously solved for the respective reals and imaginaries of the spectra of all the unknown thermal property distributions, to stabilize the estimations in the time direction, the respective simultaneous equations are regularized using the penalty terms (125) to (133) [i.e., normal equations (134) to (136)]. The regularization parameters multiplied to the unknown, respective real and imaginary of the spectra of the frequency l thermal property distributions can be set proportional to the reciprocals of the SNRs of the powers at the frequency at the time or during the times in the respective composition (integral) regions of the thermal quantities multiplied to the unknown thermal property distributions in eqs. (41), (43), (45) and (47). Furthermore, the regularization parameters can also be set dependent on the time and position.

(E) When the two algebra equations derived for all the frequencies l (0~n) of an arbitrary time j (j=0~n) of arbitrary sequences i (=1~M) are respectively solved for the reals and imaginaries of the spectra of all the unknown thermal property distributions, to stabilize the estimations in the frequency domain, the respective simultaneous equations are regularized using the penalty terms (107) to (115) and (125) to (133) with respect to the spectra [i.e., normal equations (134) to (136)], where, the frequency derivatives are used instead of the temporal derivatives. The regularization parameters multiplied to the unknown, respective real and imaginary of the spectra of the frequency l thermal property distributions can be set proportional to the reciprocals of the SNRs of the powers at the frequency in the respective composition (integral) regions of the thermal quantities multiplied to the unknown thermal property distributions in eqs. (41), (43),

(45) and (47). Furthermore, the regularization parameters can also be set dependent on the time and position.

Moreover, as in (C) and (D), to stabilize the estimations in the spatial and time directions as well, when the two algebra equations derived for all the frequencies 1 (0~n) of the different times j (j=0~n) or the different sequences i (=1~M) are solved for the reals and imaginaries of the spectra of the unknown thermal property distributions ($\geqq$1), the simultaneous equations are regularized using the penalty terms (107) to (115) and (125) to (133) in addition to the above-described penalty terms. The regularization parameters multiplied to the unknown, respective real and imaginary of the spectra of the frequency l thermal property distributions can be set proportional to the reciprocals of the SNRs of the powers at the frequency in the respective composition (integral) regions of the thermal quantities multiplied to the unknown thermal property distributions in eqs. (41), (43), (45) and (47). Furthermore, the regularization parameters can also be set dependent on the time and position.

Thus, by solving the algebra equations (76) of one of (A) to (E), the frequency variances of the respective thermal property distributions can be estimated at the time or during the times.

Furthermore, the sequence of the thermal conductivity nodal distributions can be obtained by performing the inverse Fourier's transform at each position using the spectra obtained at the time or during times. For instance, at j=0~n, the sequence of the thermal conductivity nodal distribution is obtained as $$k_i(I, J, K, j) = \frac{1}{n+1} \sum_{j=0}^{n} [k_i(I, J, K, l)[\exp(j\theta(I, J, K, l))]$$
$$[\cos(2\pi l\Delta f j\Delta t) + j\sin(2\pi l\Delta f j\Delta t)],$$

from which the sequence of the thermal conductivity distribution $k_i(x,y,z,t)$ can be obtained.

As in the case when the ROI is 2D or 1D.

Otherwise, when the processing of (I) is performed, the frequency variances can be estimated by performing the spectrum analysis with respect to the obtained sequential thermal property distributions at each position at the time or during the times. When the frequency variances are original targets, for both (I) and (II), the sinusoidal frequency of the thermal sources/sinks are changed, or the wide-band thermal sources/sinks are used to generate wide-band sequences of the temperature distributions such that the target bandwidth can be dealt with.

Here, when in (II) the spontaneous spectra of the temperatures are measured, the spontaneous frequency is used as the frequency l. When the temperature distribution is sinusoidal change, the frequency is used as the frequency l.

Here, in (II), the spectrum analysis can be similarly applied to the spatial directions not for temporal direction.

These are basic principles related to the present invention. The reference regions and values can also be realized by attaching the various reference materials onto the target ROI. When the temperature data cannot be obtained at some region in the ROI, the region can be excluded from the ROI, after which the values at the time in the region can be obtained by interpolating or extrapolating using the values in the neighborhoods. Similarly, anisotropic thermal properties can be estimated.

Furthermore, the estimated thermal conductivity, density, specific heat and calculated high order data (e.g., frequency variances) are used to evaluate their nonlinear properties by performing the linear approximations for a short time or a small space with respect to the nonlinear phenomena. This thermal property measurement apparatus can be properly specialized to deal with various targets, e.g., thermal materials, electric materials, superconductor, living things including human, structures, etc. For instance, the apparatus can be realized as a microscope. The present invention can be used for evaluations of the physical properties including the influences of the environment conditions such as temperature, load, etc. The apparent thermal properties can also be evaluated, for instance, when the thickness of the target is inhomogeneous. As the result, the evaluated apparent values can also be used to estimate the thickness of the target using the data of thickness versus the apparent values. Furthermore, the present invention can be used for the diagnosis and monitoring [e.g., growth of materials, realization processes of the structures, contactness of the circuits, repairing processes of materials/structures, growth of the lesions of living things, treatment effectiveness of the lesions (inflammation and degeneration etc. due to the medicines, radiations such as high intensity ultrasound, electromagnetic rf/microwaves, laser etc., cryotherapies, surgeries), behaviors of blood, contrast medium such as microbubbles, etc.], evaluations of the functions (e.g., design of circuits, circuits, parts of the circuits, living things, circuits of the nerve under culture, etc.) or nondestructive evaluations, etc.

Next, the second conduct form of the present invention related to the thermal property measurement apparatus is explained. The apparatus of the first conduct form is the basis, where the measurement target is set on the stage. In contrast, this apparatus is used for the targets that cannot be set on the stage because they are too big, or cannot be moved such as structures.

Figure 3:
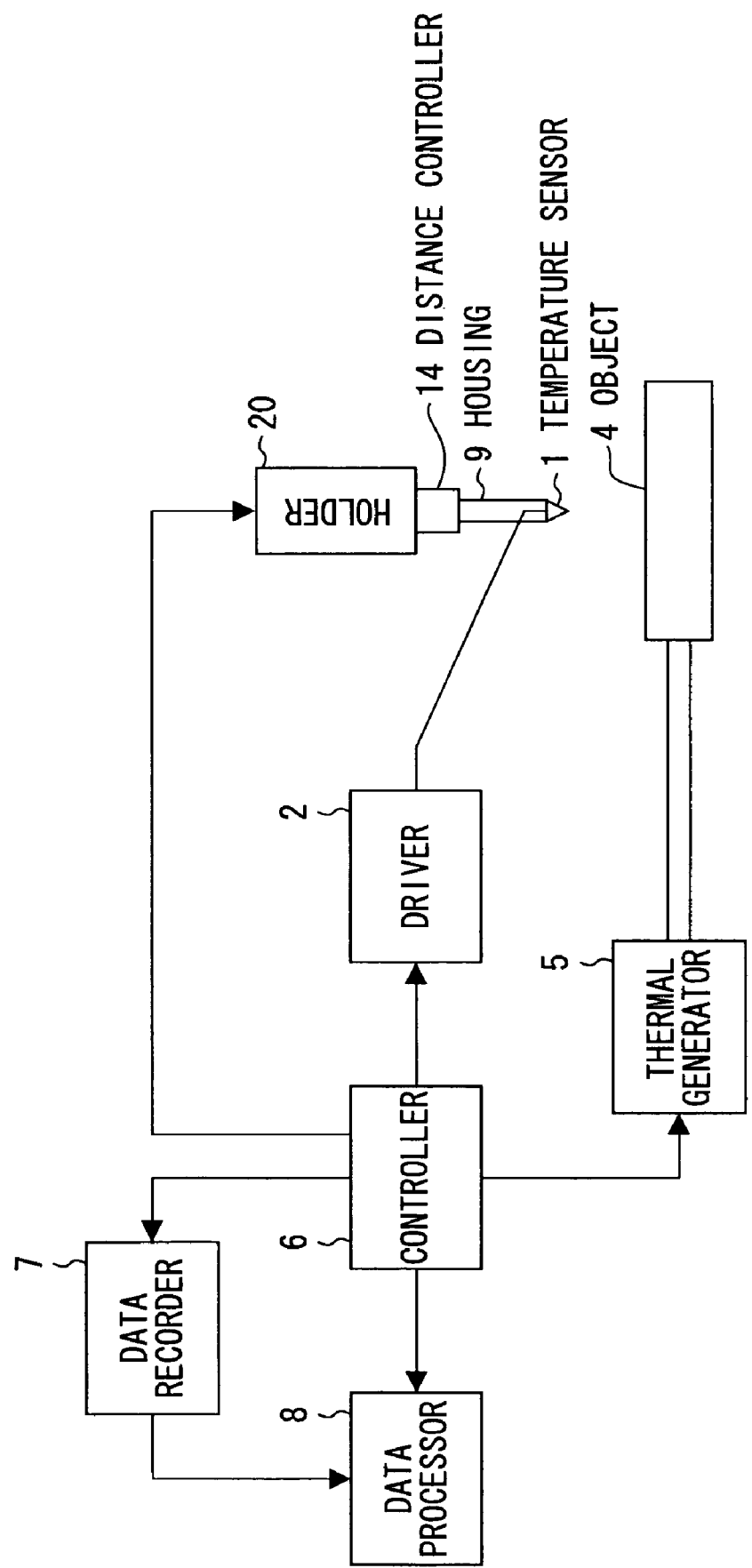
FIG. 3 shows the schematic representation of a global of thermal property measurement apparatus, related to the second conduct form of the present invention.

FIG. 3 shows the schematic representation of a global of thermal property measurement apparatus, related to the second conduct form of the present invention. There exists a holder 20 for setting the temperature sensor 1 towards the target 4 and for changing the lateral positions relative between the temperature sensor and object. Here, the positions of the holder 20 and the distance controller 14 can be in reverse.

Next, the third conduct form of the present invention related to the thermal property measurement apparatus is explained.

Figure 4:
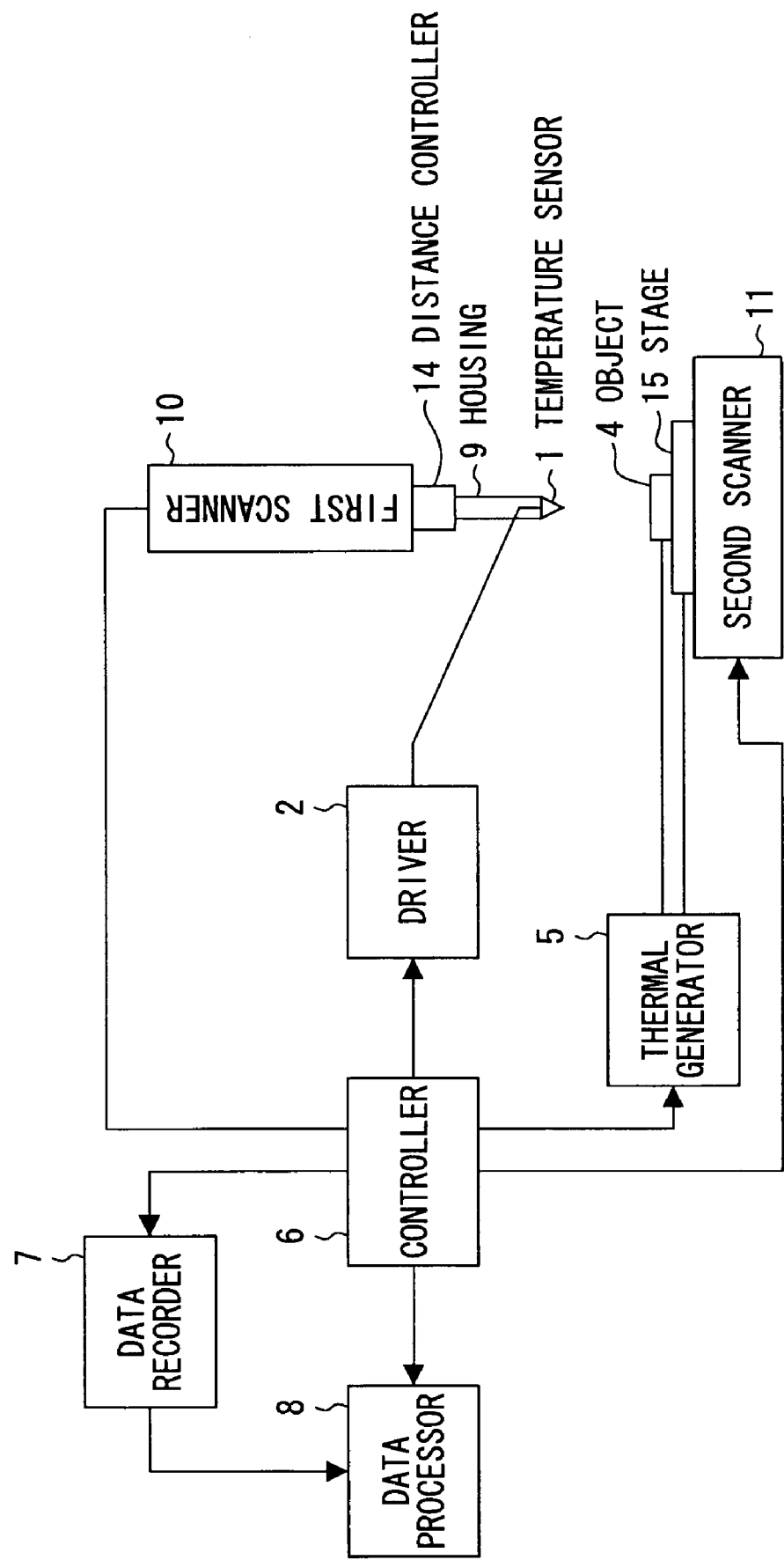
FIG. 4 shows the schematic representation of a global of thermal property measurement apparatus, related to the third conduct form of the present invention.
Figure 5:
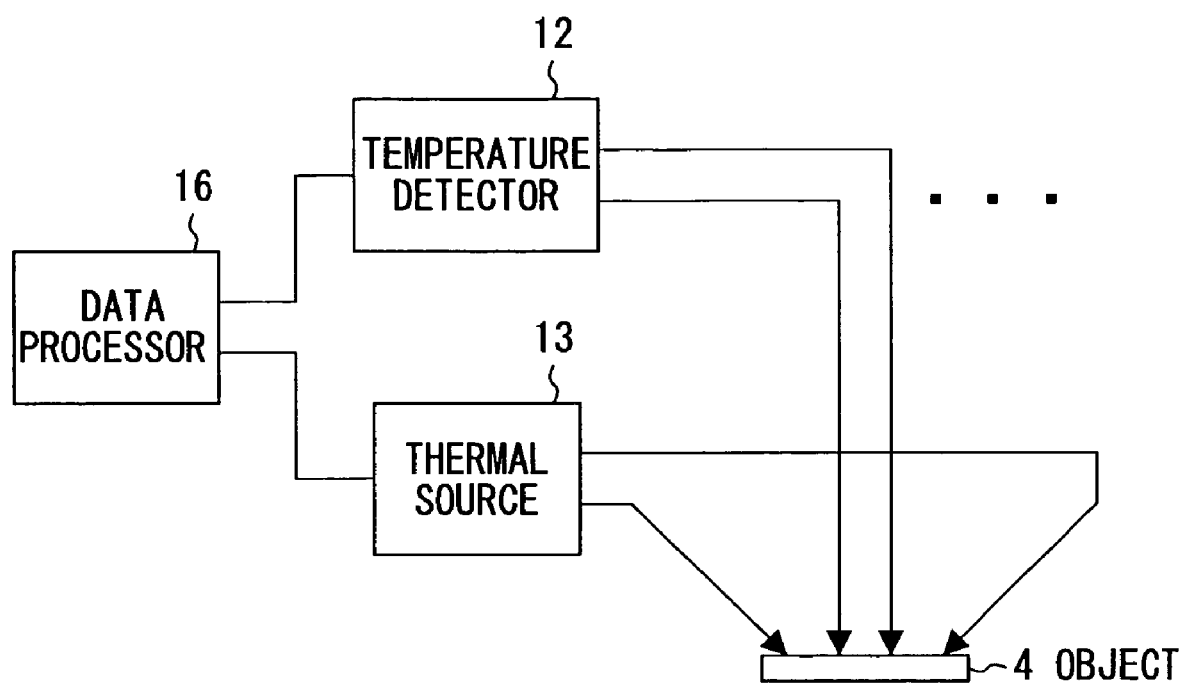
FIG. 5 shows the schematic representation of a previous global of thermal property measurement apparatus.

FIG. 4 shows the schematic representation of a global of thermal property measurement apparatus, related to the third conduct form of the present invention. There exist the first and second scanners 10 and 11. Thereby, the various rapid scans can be performed. In the present conduct form, the distance controller 14 is set at sensor, it can also be set at the target. Moreover, the positions of the scanner 10 and the distance controller 14 can be in reverse.

Here, for the temperature sensors, other light detectors, pyroelectric sensors, thermocouplers, ultrasound sensors, magnetic resonance sensors, impedance sensors can also be used. To deal with various targets such as solids, liquids, gases, mixtures, living things, etc., these sensors or the arrayed sensors can also be used.

Furthermore, as described above, by the determination procedure for determining at each local region or each point in the ROI whether both the thermal conductive and convection phenomena is dealt with or not (i.e., either phenomenon), the heat transfer coefficient h (distribution, sequence) becomes unknown instead of the thermal conductivity (distribution, sequence) at some region or point in the ROI by dealing with the convection phenomena (natural, forced)

instead of the conductive phenomena. For instance, eq. (41) can be expressed as $\rho_i c_i(dTi/dt)=dQi$ using the change (distribution, sequence) of the quantity of heat $dQi$ defined here by $h(T1-T2)$ or $\nabla\{h(T1-T2)\}$, i.e., the product of heat transfer coefficient h and difference of the temperatures. Otherwise, both thermal conductivity and transfer coefficient (distributions, sequences) become unknown when dealing with both the conductive and convection phenomena. For instance, eq. (41) can be expressed as $\rho_i c_i(dTi/dt)=-\nabla \cdot (kiDi)+dQi$. Moreover, the change of the quantity of heat due to the convection can also be determined by motion velocity, density, specific heat etc. in addition to the heat transfer coefficient, these distributions or the sequences can also become unknown, for instance, in the bio-heat transfer equation etc.

Furthermore, when the data of the thermal source/sinks (distributions, sequences) are known at some region or position, the above-described thermal conductive and convection phenomena can also be dealt with. For instance, eq. (41) can be expressed as $\rho_i c_i(dTi/dt)=-\nabla \cdot (kiDi)+Qi$ using the thermal sources/sinks (distributions, sequences).

Furthermore, the heat generations due to the radiation therapies (high intensity ultrasound, electromagnetic rf/micro waves, laser etc.), heat sinks due to the cryotherapies, heat generations/sinks due to medicines, inflammations due to these treatments or surgeries are evaluated by estimating the thermal sources/sinks (distributions, sequences) together with the thermal properties.

Furthermore, after estimating the thermal properties, the thermal sources/sinks (distributions, sequences) can be estimated. By interrupting the treatments, the thermal properties can be estimated without dealing with the thermal sources/sinks. By these, evaluations, the temperature change can be predicted and can be used for the treatment planning.

Using the present invention, the conditions, distributions, volumes, number or their changes of the inhomogeneous regions can also be evaluated (for instance, the growths of the lesions, degenerations due to the various treatments, red cells in blood, cells, contrast medium such as microbubbles, etc.).

Thus, by the present invention, the thermal conductivity or transfer coefficient in the ROI can be estimated from the measured temperature distributions. Particularly, when there already exists temperature distribution in the ROI, without disturbing the temperature field, by measuring the temperature distribution, the thermal conductivity or transfer coefficient can be estimated.

The invention claimed is:

1. A thermal property measurement apparatus comprising:
temperature detecting means for measuring temperature at plural positions in a 3D, 2D or 1D ROI (region of interest) within a target;
storage means for storing temperature data representing the temperature measured over the ROI by the temperature detecting means together with position data representing the plural positions where the temperature is measured and time data representing time when the temperature is measured;
processing means for calculating at least one thermal property distribution selected from among thermal conductivity distribution, thermal capacity distribution, thermal diffusivity distribution, heat transfer coefficient distribution, convection distribution, heat source distribution, heat sink distribution, distribution of ratio of thermal conductivity and density, distribution of ratio of thermal conductivity and specific heat, distribution of ratio of heat transfer coefficient and density, distribution of ratio of heat transfer coefficient and specific heat, density distribution, specific heat distribution, temporal change of one of these distributions, and frequency variance of one of these distributions, by solving regularized linear normal equations about said at least one thermal property distribution obtained from at least one heat transfer equation having coefficients determined on the basis of the temperature data, the position data, and the time data stored in said storage means by using discrete approximation and least-squares minimization together with regularization using at least one penalty term including at least one of a square of said at least one thermal property distribution, a square of a gradient of said at least one thermal property distribution, a square of a Laplacian of said at least one thermal property distribution, and a square of at least one of first and second temporal partial derivatives of said at least one thermal property distribution without using a sensitivity theorem; and
control means for controlling the temperature detecting means, storage means and processing means.

2. The thermal property measurement apparatus according to claim 1, further comprising:
display means for displaying at least one measurement result.

3. The thermal property measurement apparatus according to claim 1, wherein said processing means solves regularized linear normal equations obtained from the at least one heat transfer equation together with at least one of temporally changeable reference data and non-changeable reference data representing at least one of reference thermal conductivity, reference capacity, reference thermal diffusivity, reference heat transfer coefficient, reference convection, reference thermal source, reference thermal sink, reference ratio of thermal conductivity and density, reference ratio of thermal conductivity and specific heat, reference ratio of heat transfer coefficient and density, reference ratio of heat transfer coefficient and specific heat, reference density, and reference specific heat together with the position data and the time data provided in 3D, 2D or 1D reference regions set in the ROI.

4. The thermal property measurement apparatus according to claim 1, wherein the control means controls movement of the temperature detecting means and/or means for moving the target.

5. The thermal property measurement apparatus according to claim 4, wherein the temperature detecting means is a non-contact sensor.

* * * * *